(12) United States Patent
Giraud et al.

(10) Patent No.: US 11,857,771 B2
(45) Date of Patent: Jan. 2, 2024

(54) THREE-POSITION PLUNGERS, FILM COATED PLUNGERS AND RELATED SYRINGE ASSEMBLIES

(71) Applicant: SiO2 Medical Products, Inc., Auburn, AL (US)

(72) Inventors: Jean-Pierre Giraud, Auburn, AL (US); Bernard Sol, Maisons-Alfort (FR); Robert J. Pangborn, Harbor Springs, MI (US); Robert S. Abrams, Albany, NY (US); Joseph W. Rogers, Lafayette Hill, PA (US); Peter J. Sagona, Pottstown, PA (US); Michael J. Mims, Auburn, AL (US)

(73) Assignee: SIO2 MEDICAL PRODUCTS, INC., Auburn, AL (US)

( * ) Notice: Subject to any disclaimer, the term of this patent is extended or adjusted under 35 U.S.C. 154(b) by 387 days.

(21) Appl. No.: 17/107,241

(22) Filed: Nov. 30, 2020

(65) Prior Publication Data

US 2021/0077742 A1    Mar. 18, 2021

Related U.S. Application Data

(62) Division of application No. 15/510,777, filed as application No. PCT/US2015/024558 on Apr. 6, 2015, now Pat. No. 10,850,042.

(Continued)

(51) Int. Cl.
*A61M 5/31*    (2006.01)
*A61M 5/315*   (2006.01)
(Continued)

(52) U.S. Cl.
CPC ....... *A61M 5/31578* (2013.01); *A61L 31/048* (2013.01); *A61L 31/10* (2013.01);
(Continued)

(58) Field of Classification Search
CPC .......... A61M 5/31511; A61M 5/31513; A61M 5/31515; A61M 5/31501; A61M 2005/3151; A61M 2005/31508
See application file for complete search history.

(56) References Cited

U.S. PATENT DOCUMENTS 2,895,773 A   7/1959  McConnaughey
3,669,111 A   6/1972  Dubner
(Continued)

FOREIGN PATENT DOCUMENTS

CA    1324545    11/1993
CN    1152882 A   6/1997
(Continued)

*Primary Examiner* — William R Carpenter
(74) *Attorney, Agent, or Firm* — David B. Gornish; Eckert Seamans Cherin and Mellott LLC

(57) ABSTRACT

A three-position plunger is provided including a sleeve having an opening at a distal end, a pre-load cavity proximal to and in communication with the opening, a first cavity proximal to and in communication with the pre-load cavity, a second cavity proximal to and in communication with the pre-load cavity, and at least one rib. The rib(s) is generally aligned with the first cavity. The plunger further includes an insert configured to be displaced from the pre-load cavity to the first cavity and from the first cavity to the second cavity. The insert is configured to provide support for the compression of the rib(s) when the insert is positioned in the first cavity.

9 Claims, 42 Drawing Sheets

US 11,857,771 B2
Page 2

Related U.S. Application Data

(60) Provisional application No. 62/048,675, filed on Sep. 10, 2014, provisional application No. 62/092,944, filed on Dec. 17, 2014.

(51) Int. Cl.
*A61L 31/04* (2006.01)
*A61L 31/10* (2006.01)
*A61L 31/14* (2006.01)

(52) U.S. Cl.
CPC ......... *A61L 31/14* (2013.01); *A61M 5/31513* (2013.01); *A61M 5/31515* (2013.01); *A61L 2400/10* (2013.01); *A61M 2005/31508* (2013.01); *A61M 2205/0222* (2013.01); *A61M 2205/0238* (2013.01); *A61M 2207/00* (2013.01)

(56) References Cited

U.S. PATENT DOCUMENTS

| | | |
|---|---|---|
| 4,064,879 A | 12/1977 | Leibinsohn |
| 5,314,416 A | 5/1994 | Lewis et al. |
| 5,413,563 A | 5/1995 | Basile et al. |
| 7,985,188 B2 | 7/2011 | Felts et al. |
| 8,172,795 B2 | 5/2012 | Lum et al. |
| 9,192,725 B2 | 11/2015 | Kawamura |
| 9,511,192 B2 | 12/2016 | Kawamura |
| 9,522,237 B2 | 12/2016 | Alheidt et al. |
| 9,592,346 B2 | 3/2017 | Quinn et al. |
| 9,642,969 B2 | 5/2017 | Ivosevic et al. |
| 9,649,444 B2 | 5/2017 | Schiller et al. |
| 9,717,857 B2 | 8/2017 | Lanier |
| 9,827,376 B2 | 11/2017 | Titus et al. |
| 10,159,796 B2 | 12/2018 | Schiff et al. |
| 10,850,042 B2 | 12/2020 | Giraud et al. |
| 2010/0179487 A1 | 7/2010 | Woehr |
| 2011/0224611 A1 | 9/2011 | Lum et al. |
| 2012/0253291 A1 | 10/2012 | Ivosevic et al. |
| 2013/0041241 A1 | 2/2013 | Felts et al. |
| 2013/0085452 A1 | 4/2013 | Schiff et al. |
| 2013/0209766 A1 | 8/2013 | Felts et al. |
| 2013/0291632 A1 | 11/2013 | Felts et al. |
| 2014/0228802 A1 | 8/2014 | Mackey et al. |
| 2017/0296756 A1 | 10/2017 | Giraud et al. |
| 2019/0009035 A1 | 1/2019 | Lum et al. |
| 2021/0077742 A1 | 3/2021 | Giraud et al. |

FOREIGN PATENT DOCUMENTS

| | | |
|---|---|---|
| CN | 101157409 A | 4/2008 |
| CN | 103553976 A | 1/2014 |
| EP | 1849490 A1 | 10/2007 |
| EP | 1703930 B1 | 2/2018 |
| EP | 3785751 A1 | 3/2021 |
| JP | 06-327770 A | 11/1994 |
| JP | 08-182760 A | 7/1996 |
| JP | 2001-025506 A | 1/2001 |
| WO | 03/047668 A1 | 6/2003 |
| WO | 2004044464 A1 | 5/2004 |
| WO | 2013/156524 A1 | 10/2013 |
| WO | 2014/050550 A1 | 4/2014 |
| WO | 2014/085348 A2 | 6/2014 |
| WO | 2016/039816 A1 | 3/2016 |

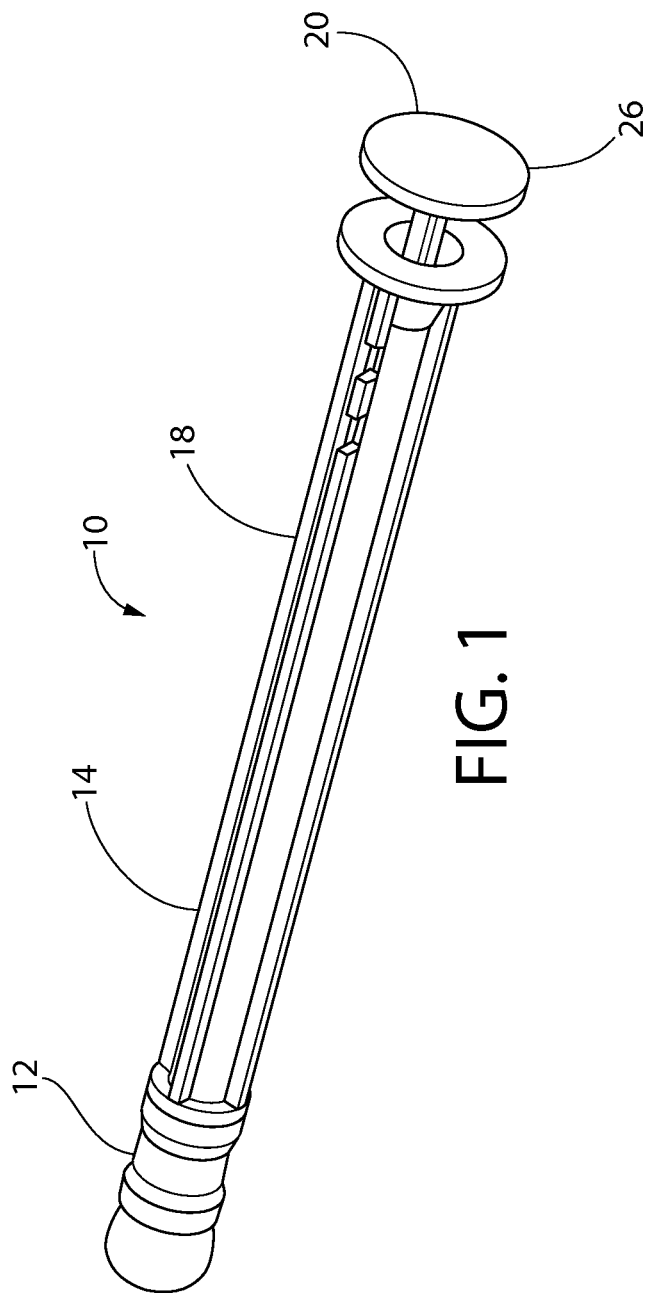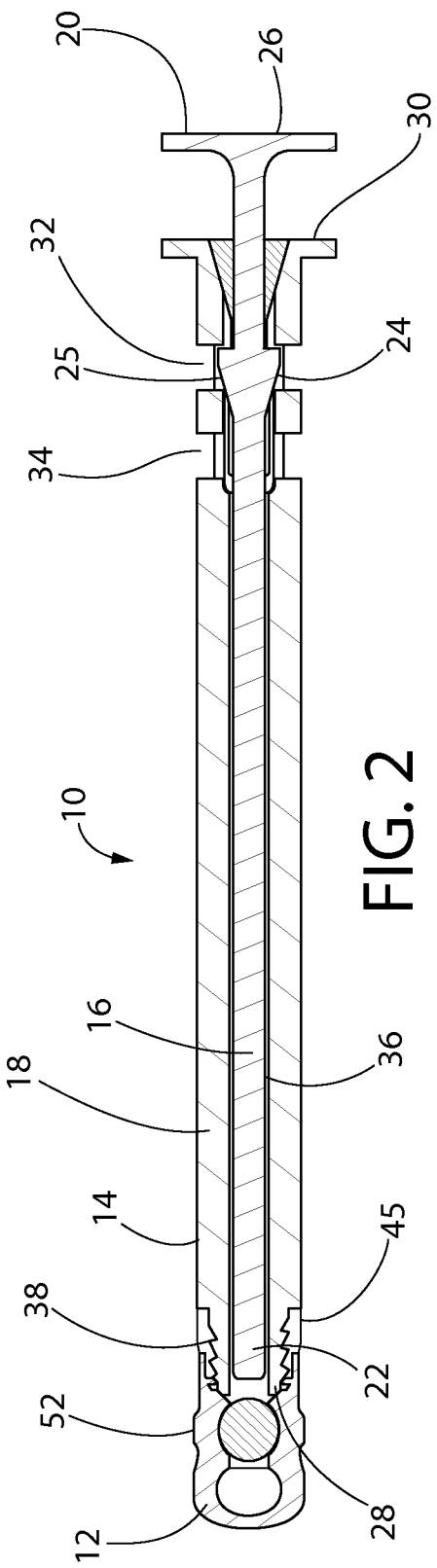

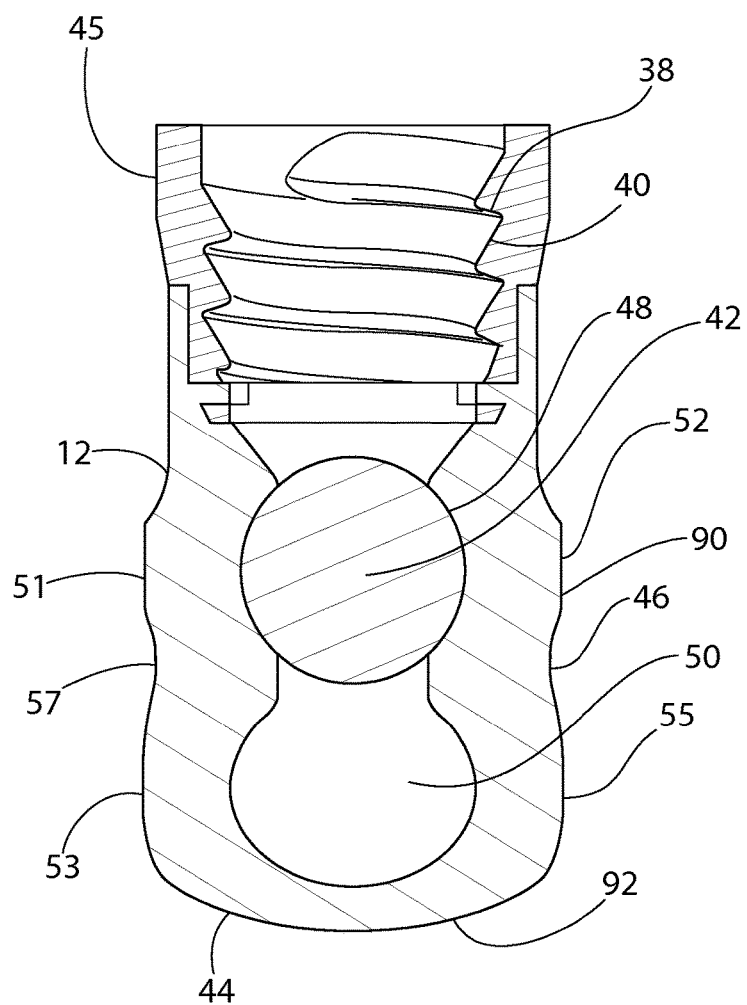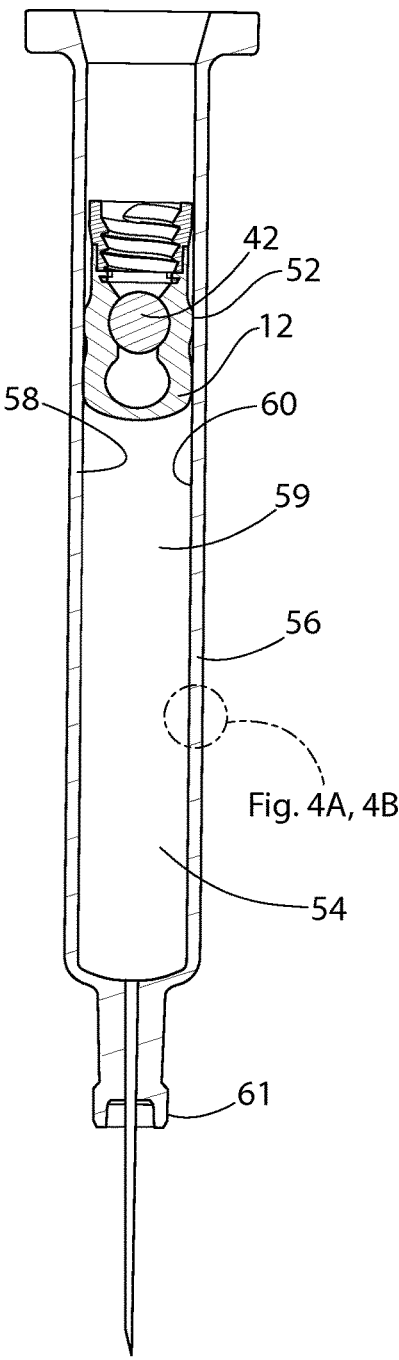
FIG. 3
FIG. 4

THREE-POSITION PLUNGERS, FILM COATED PLUNGERS AND RELATED SYRINGE ASSEMBLIES

CROSS-REFERENCE TO RELATED APPLICATIONS

This application is a Divisional of U.S. application Ser. No. 15/510,777, filed Mar. 13, 2017, which is a U.S. National Phase of International Application No. PCT/US2015/024558 filed Apr. 6, 2015, which claims priority to U.S. Provisional Application Ser. No. 62/048,675, filed Sep. 10, 2014 and 62/092,944, filed Dec. 17, 2014.

FIELD OF INVENTION

The present invention relates generally to plungers and their use in drug delivery devices, such as (pre-filled, filled before use or empty) syringes, cartridges or auto-injectors. More particularly, the present invention relates, among other things, to three-position plungers that provide and maintain container closure integrity in an expanded state or storage mode, during the shelf-life of a pre-filled syringe, and which are reducible to a constricted state or dispensing mode, when in use, to provide for relatively low and smooth plunger force when dispensing syringe contents.

BACKGROUND

The present disclosure predominantly describes use of plungers and plunger assemblies according to the present invention in connection with pre-filled syringes. However, a skilled artisan would readily appreciate that the invention is not limited to pre-filled syringes, but may include other drug delivery devices, such as (pre-filled, filled before use, or empty) syringes, cartridges and auto-injectors.

Pre-filled parenteral containers, such as syringes or cartridges, are commonly prepared and sold so that the syringe does not need to be filled by the patient or caregiver before use. The syringe, and more specifically the barrel of the syringe, may be prefilled with a variety of different injection products, including, for example, saline solution, a dye for injection, or a pharmaceutically active preparation, among other items.

Pre-filled parenteral containers are typically sealed with a rubber plunger, which provides closure integrity over the shelf life of the container's contents. To use the prefilled syringe, the packaging and cap are removed, optionally a hypodermic needle or another delivery conduit is attached to the proximal end of the barrel, the delivery conduit or syringe is moved to a use position (such as by inserting it into a patient's blood vessel or into apparatus to be rinsed with the contents of the syringe), and the plunger is advanced in the barrel to inject contents of the barrel to the point of application.

Seals provided by rubber plungers in the barrel typically involve the rubber of the plunger being pressed against the barrel. Typically the rubber plunger is larger in diameter than the internal diameter of the barrel. Thus, to displace the rubber plunger when the injection product is to be dispensed from the syringe requires overcoming this pressing force of the rubber plunger. Moreover, not only does this pressing force provided by the rubber seal typically need to be overcome when initially moving the plunger, but this force also needs to continue to be overcome as the rubber plunger is displaced along the barrel during the dispensing of the injection product. The need for relatively elevated forces to advance the plunger in the syringe may increase the difficulty at which a user may administer the injection product from the syringe. This is particularly problematic for auto injection systems where the syringe is placed into the auto injection device and the plunger is advanced by a fixed spring. Accordingly, primary considerations concerning the use of a plunger in a pre-filled parenteral container include: (1) container closure integrity ("CCI", defined below); and (2) plunger force (defined below) required to dispense syringe contents.

In practice, CCI and plunger force tend to be competing considerations. In other words, absent other factors, the tighter the fit between the plunger and the interior surface of the container to maintain adequate CCI, the greater the force necessary to advance the plunger in use. In the field of medical syringes, it is important to ensure that the plunger can move at a substantially constant speed and with a substantially constant force when advanced in the barrel. In addition, the force necessary to initiate plunger movement and then continue advancement of the plunger should be low enough to enable comfortable administration by a user.

Plunger force is essentially a function of the coefficients of friction of each of the contacting surfaces (i.e., the plunger surface and interior syringe wall surface) and the normal force exerted by the plunger against the interior wall of the syringe. The greater the respective coefficients of friction and the greater the normal force, the more force required to advance the plunger. Accordingly, efforts to improve plunger force should be directed to reducing friction and lowering normal force between contacting surfaces. However, such efforts should be tempered by the need to maintain adequate CCI, as discussed above.

To reduce friction and thus improve plunger force, lubrication may be applied to the plunger, the interior surface of the container, or both. Liquid or gel-like flowable lubricants, such as free silicone oil (e.g., polydimethylsiloxane or "PDMS"), may provide a desired level of lubrication to optimize plunger force. Optionally, use of free silicone oil to reduce plunger force, especially in small amounts, may in certain embodiments, be within the scope of the invention. However, for some applications, including preferred embodiments of the invention, use of large amounts of flowable lubricant is not desired. For example, a flowable lubricant can mix and interact with the drug product in a syringe, potentially degrading the drug or otherwise affecting its efficacy and/or safety. Such lubricants may in some cases be problematic if they are injected into the patient along with the drug product. In addition, flowable lubricants, when used with pre-filled syringes, may migrate away from the plunger over time, resulting in spots between the plunger and the interior surface of the container with little or no lubrication. This may cause a phenomenon known as "stiction," an industry term for the adhesion between the plunger and the barrel that needs to be overcome to break out the plunger and allow it to begin moving.

As an alternative (or in addition) to flowable lubricants, plungers may be made from materials having lubricious properties or include friction-reducing coatings or laminates on their exterior surfaces. Examples of such plungers include, for example: the i-COATING by TERUMO, which is disclosed in Canadian Patent No. 1,324,545, incorporated by reference herein in its entirety; W. L. Gore extended ETFE film on a rubber plunger; and the CZ plunger by WEST. While these commercially available plungers may complement a lubricated barrel to provide a desired level of plunger force, it has not been found that they provide desirable plunger force absent a lubricious coating or flowable lubricant on the barrel of coated or uncoated plastic parenteral containers.

As an alternative to free liquid lubricants, lubricious coatings may be applied to the interior wall of a container barrel. Lubricity coatings, e.g., according to methods disclosed in U.S. Pat. No. 7,985,188 (incorporated by reference herein in its entirety), are particularly well suited to provide a desired level of lubricity for plungers in parenteral containers. Such lubricity coatings are preferably applied using plasma enhanced chemical vapor deposition ("PECVD") and may have one of the following atomic ratios, $Si_wO_xC_y$, or $Si_wN_xC_y$, where w is 1, x is from about 0.5 to 2.4 and y is from about 0.6 to about 3. Such lubricity coatings may have a thickness between 10 and 500 nm. Advantages of such plasma coated lubricity layers may include lower migratory potential to move into the drug product or patient than liquid, sprayed or micron-coated silicones. It is contemplated that use of such lubricity coatings to reduce plunger force is within the broad scope of the invention. However, for some applications, including preferred applications of the invention, use of such lubricity coatings may not be optimal. For example, due to relatively low cross-link density, the lubricity layer may sometimes interact with the contents of the syringe, resulting in the presence of silicon ions being extracted from the lubricity layer into the syringe. In addition, application of a lubricity coating introduces an additional step in container manufacturing, thus increasing the complexity and cost of the manufacturing process.

Thus, there is a need for optimizing plunger force in a parenteral container while maintaining adequate CCI to prevent drug leakage, protect the drug product and attain sufficient product shelf life. In addition, there is a need to provide adequate lubricity to achieve a desired plunger force while minimizing extractables and interaction with the drug product held by the container. There is a further need to optimize these factors while reducing the manufacturing cost and complexity that may be associated with applying a discrete lubricity coating to a medical barrel.

SUMMARY OF THE INVENTION

Accordingly, in one optional aspect of the invention, there is provided a convertible plunger having an internal portion and a generally cylindrical exterior surface. At least a portion of the exterior surface is maintained in an initial expanded state by a property of the internal portion. The expanded state is reducible to a constricted state by an operation that is applied to the internal portion of the plunger to alter the property. The property may include, but is not limited to, gas pressure, mechanically produced outward radial pressure or outward radial pressure produced by a liquid or gelatinous compression material disposed within the plunger.

Another optional aspect of the invention is a convertible plunger. The convertible plunger includes a generally cylindrical exterior surface configured to be seated against a generally cylindrical interior surface of a barrel wall in a storage mode and to advance along the barrel wall in a dispensing mode. A cavity in the plunger defines an interior surface of the plunger. The interior surface and exterior sealing surface defines between them a generally annular portion of the plunger. A compression material (e.g., a solid article (which may be, e.g, generally spherical in shape), or a charge of gas, liquid or gel) is disposed at least partially in the cavity and configured to apply outward radial pressure on at least a portion of the interior surface in the storage mode to provide a sealing force between the exterior sealing surface and a syringe barrel wall. The plunger may be configured to convert to the dispensing mode by reducing the applied outward radial pressure, thus reducing the sealing force between the exterior surface and a syringe barrel wall.

Another optional aspect of the invention is a plunger assembly that includes a plunger rod and a plunger. The plunger rod includes an exterior shaft and an interior shaft. The exterior shaft has an inner portion that is configured for the slideable insertion of at least a portion of the interior shaft. The interior shaft is configured to be displaced from a first position to a second position relative to the exterior shaft. Further, the plunger is operably connected to the plunger rod and is configured to receive the insertion of at least a portion of the interior shaft.

Another optional aspect of the invention is a dual actuated plunger that includes a sleeve having a first cavity, a second cavity, and at least one rib. The at least one rib is generally aligned with the first cavity. Further, the first cavity is in communication with the second cavity. The term "in communication with" as used in the foregoing sentence means that the structure within the sleeve facilitates passage of an insert between the cavities, e.g., through an opening or passage between the cavities, and/or by providing a thin breakable membrane between the cavities that is broken when the plunger is actuated. The insert is configured to be displaced from the first cavity to the second cavity, such as, for example, by the displacement of the interior shaft to the second position. Additionally, the insert is configured to provide support for the compression of the at least one rib when the insert is positioned in the first cavity. However, according to certain embodiments, the support for the compression of the at least one rib provided by the insert may be reduced and/or removed when the insert is positioned in the second cavity.

Further, another optional aspect of the invention is a dual actuated plunger having an insert, a sleeve, and a connector body. At least a portion of the connector body is positioned within the sleeve between the sleeve and the insert and is configured to provide support for the compression of the sleeve against an inner surface of a sidewall of a barrel. Additionally, according to certain embodiments, the insert is configured to be displaced from a deactivated position to an activated position in the plunger. Further, the sleeve is configured to have a length of the sleeve elongated and outer width of the sleeve reduced when the insert is in the activated position. Such a reduction in width may reduce the compressive force or radial pressure that at least a portion of the sleeve, such as at least one rib on the sleeve, exerts against an adjacent surface such as, for example, the interior surface of a sidewall of a barrel.

Additionally, another optional aspect of the invention is a method for forming a film coated plunger. The method includes forming, from a film of a thermoplastic elastomer, a preform coating. Additionally, the preform coating is pressed against a sidewall and/or base of a mold cavity to generally conform an outer shape of the preformed coating to a shape of the plunger. The method also includes injecting a plunger material into the mold cavity. The injected plunger material may be positioned against an adjacent inner surface of the preform coating to form the film coated plunger.

Another optional aspect of the invention is a film coated plunger configured for insertion into a barrel, the barrel having a product containing area. The film coated plunger includes a plunger that is configured to provide a compressive force against an inner surface of a sidewall of a barrel to form a compressive seal between the plunger and the sidewall of the barrel. The film coated plunger further includes a film coating that is positioned about at least a portion of the plunger. The film coating is configured to reduce a friction between the film coated plunger and the inner surface of the sidewall of the barrel and/or to provide a barrier between the plunger and a product contained in the product containing area of the barrel.

Other aspects of the invention will be apparent from this disclosure and the accompanying drawings.

BRIEF DESCRIPTION OF THE DRAWINGS

FIG. 1 illustrates a perspective view of a plunger assembly.

FIG. 2 illustrates an axial sectional view of a plunger assembly according to an illustrated embodiment.

FIG. 3 illustrates an isolated partial sectional view of the plunger shown in FIG. 2, with the connector body transparent to reveal internal structure.

FIG. 4 illustrates a partial sectional view of the plunger of FIG. 3 positioned within a barrel of a syringe.

Figure 4A:
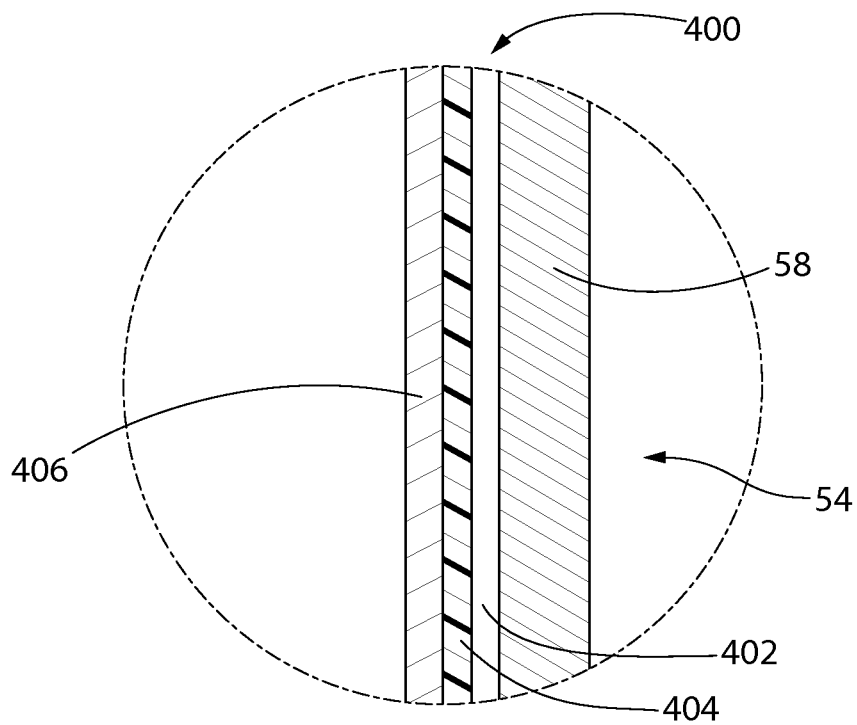
FIG. 4A is an enlarged sectional view of a first alternative embodiment of the inner surface of the syringe of FIG. 4, comprising a trilayer coating set disposed thereon.

The following reference characters are used in the drawing figures:

| | |
|---|---|
| 10, 210 | Plunger assembly |
| 12, 212 | Convertible plunger |
| 12a-12i | Convertible plunger |
| 14, 214 | Plunger rod |
| 16, 216 | Interior shaft |
| 16' | Tip |
| 18, 218 | Exterior shaft |
| 20, 220 | Distal end |
| 22, 222 | Proximal end |
| 24, 224 | Locking tab |
| 25, 225 | Tapered surface |
| 26, 226 | Actuator |
| 28, 228 | First end |
| 30, 230 | Second end |
| 32, 232 | First recess |
| 34, 234 | Second recess |
| 36, 236 | Inner portion |
| 38, 238 | Thread (of exterior shaft 18, 218) |
| 40, 240 | Thread (of plunger 12, 212) |
| 42 | Insert |
| 44 | Sleeve |
| 45 | Connector body |
| 46 | Outer portion |
| 48 | First cavity |
| 48a-g | Cavity |
| 50 | Second cavity |
| 51 | Storage Sealing Section |
| 52 | Rib of Storage Sealing Section |
| 53 | Liquid Sealing Section |
| 54 | Interior area |
| 55 | Rib of Liquid Sealing Section |
| 56 | Barrel |
| 57 | Valley |
| 58 | Sidewall |
| 59 | Product containing area |
| 60 | Inner surface |
| 61 | Proximal end (of barrel 56) |
| 62 | Insert |
| 63 | Connector body |
| 64 | Sleeve |
| 65 | First section (of connector body 63) |
| 66 | Cavity |
| 67 | Second section (of connector body 63) |
| 68 | Shaft |
| 69 | Third section (of connector body 63) |
| 70 | Outer surface (of insert 62) |
| 72 | Recesses (of insert 62) |
| 74 | Protrusions (of insert 62) |
| 76 | Inner surface (of sleeve 64) |
| 77 | Recesses (of connector body 63) |
| 78 | Protrusions (of sleeve 64) |
| 79 | Protrusions (of connector body 63) |
| 80 | Recesses (of sleeve 64) |
| 82 | Bottom portion (of outer surface 70) |
| 84 | Lower portion (of inner surface 76) |
| 86 | Exterior surface |
| 88 | Film coating |
| 90 | Sidewall (of plunger 12) |
| 92 | Nose cone (of plunger 12) |
| 94 | Film |
| 96 | Forming die |
| 98 | Forming plug |
| 100 | Base wall (of forming plug 98) |
| 102 | Bottom portion (of forming die 96) |
| 104 | Sidewall (of forming die 96) |
| 106 | Coating preform |
| 107 | Mold |
| 108 | Mold cavity |
| 110 | Sidewall (of mold cavity 108) |
| 112 | Bottom wall (of mold cavity 108) |
| 113 | Mold core |
| 114 | Trim tool |
| 152 | Rib |
| 194 | Cap |
| 300 | Spherical mesh insert |
| 302 | Cylindrical insert |
| 303 | Central portion |
| 304 | Protrusion |
| 304a | Cavity |
| 304b | Protrusion |
| 305 | Opening |
| 305a, b | Opening |
| 306 | Insert |
| 307 | Wings |
| 308 | Porous material |
| 309 | Stopper |
| 310 | Sealed inner cavity |
| 310a | Compression material |
| 311 | Tip |
| 312 | Membrane |
| 314 | Juts |
| 316 | Valve |
| 318 | Sliding shaft |
| 400 | Coating set |
| 402 | Tie coating or layer |
| 404 | Barrier coating or layer |
| 406 | pH Protective coating or layer |
| 500 | Sample A |
| 502 | Sample B |
| 504 | Sample C |
| 510 | Set A |
| 512 | Set B |
| 514 | Set C |
| 516 | Bare COP syringe results |
| 518 | Trilayer syringe results |
| 520 | Bare glass syringe results |
| 522 | Glass syringe with PDMS results |
| 612 | Three-position plunger |
| 614 | Plunger rod |
| 616 | Interior shaft |
| 618 | Exterior shaft |
| 630 | Round collar |
| 642 | Insert |
| 642a | Insert shaft |
| 642b | Insert flange |
| 643 | Opening |
| 644 | Sleeve |
| 647 | Pre-load cavity |
| 648 | First cavity |
| 650 | Second cavity |
| 712, 812, 912 | Convertible plunger |
| 738, 838, 938 | Thread (of exterior shaft 18, 218) |
| 740, 840, 940 | Thread (of plunger 712, 812, 912) |
| 742, 842, 942 | Insert |
| 744, 844, 944 | Sleeve |
| 745, 845, 945 | Connector body |
| 746, 846, 946 | Outer portion |
| 748, 848, 948 | First cavity |
| 750, 850, 950 | Second cavity |
| 751, 851, 951 | Storage Sealing Section |
| 752, 852, 952 | Rib(s) of Storage Sealing Section |
| 753, 853, 953 | Liquid Sealing Section |
| 755, 855, 955 | Rib of Liquid Sealing Section |
| 988 | Film coating |
| 790, 890, 990 | Sidewall (of plunger 712, 812, 912) |
| 792, 892, 992 | Nose cone |
| 1012 | Convertible plunger or stretchable plunger |
| 1038 | Thread (of exterior shaft 18, 218) |
| 1040 | Thread (of plunger 1012) |
| 1044 | Sleeve |
| 1051 | Storage Sealing Section |
| 1052 | Rib(s) of Storage Sealing Section |
| 1053 | Liquid Sealing Section |

| | | |
|---|---|---|
| 1094 | Cap | |
| 1095 | Stem | |
| 1097 | Stem cover | |

DETAILED DESCRIPTION OF THE PREFERRED EMBODIMENTS

The present invention will now be described more fully with reference to the accompanying drawings, in which several embodiments are shown. This invention may, however, be embodied in many different forms and should not be construed as limited to the embodiments set forth here. Rather, these embodiments are examples of the invention, which has the full scope indicated by the language of the claims. Like numbers refer to like elements throughout.

Definitions

In the context of the present invention, the following definitions and abbreviations are used:

For purposes of the present invention, an "organosilicon precursor" is a compound having at least one of the linkages:

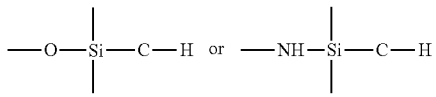

which is a tetravalent silicon atom connected to an oxygen or nitrogen atom and an organic carbon atom (an organic carbon atom being a carbon atom bonded to at least one hydrogen atom). A volatile organosilicon precursor, defined as such a precursor that can be supplied as a vapor in a PECVD apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, and a combination of any two or more of these precursors.

Values of w, x, y, and z are applicable to the empirical composition $Si_wO_xC_yH_z$ throughout this specification. The values of w, x, y, and z used throughout this specification should be understood as ratios or an empirical formula (for example for a coating or layer), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$. Also, although $SiO_xC_yH_z$ is described as equivalent to $SiO_xC_y$, it is not necessary to show the presence of hydrogen in any proportion to show the presence of $SiO_xC_y$.

The term "barrel" refers to a medical barrel, as may be used, e.g., as part of a medical device for containing and dispensing liquid product, such as a syringe.

The term "plunger" when used with reference to any embodiment of the present invention (as opposed to with reference to conventional plungers in the art) refers to a convertible plunger according to the present invention.

"Frictional resistance" can be static frictional resistance and/or kinetic frictional resistance.

The "plunger sliding force" (synonym to "glide force," "maintenance force", or $F_m$, also used in this description) in the context of the present invention is the force required to maintain movement of a plunger tip in a syringe barrel, for example during aspiration or dispense. It can advantageously be determined using the ISO 7886-1:1993 test known in the art. A synonym for "plunger sliding force" often used in the art is "plunger force" or "pushing force".

"Container closure integrity" or "CCI" refers to the ability of a container closure system, e.g., a plunger disposed in a prefilled syringe barrel, to provide protection and maintain efficacy and sterility during the shelf life of a sterile product contained in the container.

The "plunger breakout force" (synonym to "breakout force", "break loose force", "initiation force", $F_i$, also used in this description) in the context of the present invention is the initial force required to move the plunger tip in a syringe, for example in a prefilled syringe.

Both "plunger sliding force" and "plunger breakout force" and methods for their measurement are described in more detail in subsequent parts of this description. These two forces can be expressed in N, lbs or kg and all three units are used herein. These units correlate as follows: 1N=0.102 kg=0.2248 lbs (pounds).

"Slidably" means that the plunger tip, closure, or other removable part is permitted to slide in a syringe barrel or other vessel.

The term "syringe" is broadly defined to include cartridges, injection "pens," and other types of barrels or reservoirs adapted to be assembled with one or more other components to provide a functional syringe. "Syringe" is also broadly defined to include related articles such as auto-injectors, which provide a mechanism for dispensing the contents.

The term "outward radial pressure" refers to pressure applied or exerted in a direction outward from (or away from) the plunger's central axis.

The terms "film" and "film coating" may be used interchangeably in this specification.

Convertible Plungers and Film-Coated Plungers

FIGS. 1-2 illustrate a two-position plunger assembly 10 according to an embodiment of the present invention. The plunger assembly 10 may have a variety of different shapes and sizes. For example, according to an illustrated embodiment, the plunger assembly 10 may be approximately 79 millimeters long. The plunger assembly 10 includes a convertible plunger 12 and a plunger rod 14. The plunger rod 14 may include an interior shaft 16 and an exterior shaft 18. The interior shaft 16 includes a distal end 20, a proximal end 22, and a locking tab 24. According to certain embodiments, the distal end 20 of the interior shaft 16 may be configured to form an actuator 26 that, during use of the plunger assembly 10, is to be pressed upon by a user, such as, for example, by the thumb of the user. The exterior shaft 18 may include a first end 28, a second end 30, a first recess 32, a second recess 34, and an inner portion 36. According to certain embodiments, the first end 28 may be configured for a threaded engagement with the convertible plunger 12. For example, as shown, the first end 28 may include an external thread 38 that is configured to mate with an internal thread 40 of the convertible plunger 12.

At least a portion of the interior shaft 16 is configured for slideable displacement along the inner portion 36 of the exterior shaft 18. Additionally, the locking tab 24 may protrude from at least a portion of the interior shaft 16. In the illustrated embodiment, the locking tab 24 has a tapered surface 25 that may assist in controlling the direction and timing of the displacement of the interior shaft 16 along the inner portion 36 of the exterior shaft 18. For example, at least FIG. 2 illustrates the interior shaft 16 in a first position relative to the exterior shaft 18, with the locking tab 24 protruding into at least a portion of the first recess 32 of the exterior shaft 18. The orientation of the tapered surface 25 of the locking tab 32 allows, when sufficient force is exerted upon the actuator 26, for the locking tab 32 to be at least temporarily compressed or deformed in size so that the locking tab 24 may at least temporarily enter into the inner portion 26 as the locking tab 25 is moved from the first recess 32 to the second recess 34. However, in the absence of sufficient force, the locking tab 32 may remain in the first recess 32, thereby maintaining the interior shaft 16 in the first position.

Figure 5:
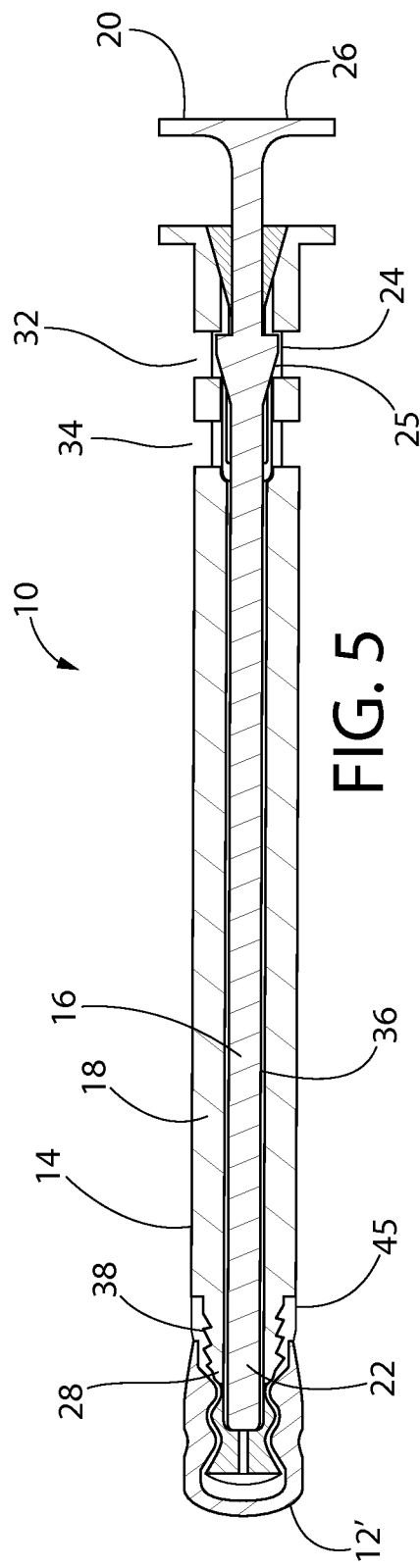
FIG. 5 illustrates an axial sectional view of a plunger assembly according to an illustrated embodiment.

The distance that the locking tab 24 is to travel from the first recess 32 to the second recess 34, and thus the distance the interior shaft 16 is displaced relative to the exterior shaft 18 when moving from the first position to the second position may vary for different plunger assemblies. For example, according to certain embodiments, the interior shaft 16 may be displaced approximately 3 to 5 millimeters. Additionally, as shown in FIGS. 2 and 5, according to certain embodiments, the proximal end 22 of the interior shaft 16 may or may not be housed in the interior portion 36 of the exterior shaft 18 when the interior shaft 16 is in the first position.

Further, the orientation and size of the tapered surface 25 of the locking tab 24 may provide the locking tab 24 with sufficient width to prevent the locking tab 24 from being pulled into the inner portion 36 in the general direction of the second end 30 of the exterior shaft 18. Accordingly, when the locking tab 24 is in the second recess 34, and thus the interior shaft 16 is in the second position, the orientation and size of the tapered surface 25 of the locking tab 24 may provide the locking tab 24 with sufficient width to resist the locking tab 24 from being pulled back into the first recess 32.

As shown in at least FIGS. 2-4, the convertible plunger 12 is configured to be received in an interior area 54 of a barrel 56 (e.g., of a syringe). The interior area 54 may be generally defined by a sidewall 58 of the barrel 56, the sidewall 58 having an inner surface 60. Additionally, the interior area 54 may include a product containing area 59 between the convertible plunger 12 and the proximal end 61 of the barrel 56.

According to certain embodiments, as best shown in FIG. 3, the convertible plunger 12 includes an insert 42, a sleeve 44, and a connector body 45. The connector body 45 may be operably connected to the sleeve 44, such as, for example, through the use of over molding, a plastic weld, an adhesive, and/or a mechanical fastener, such as a screw, bolt, pin, or clamp, among other connections. As previously discussed, the connector body 45 may be configured to be connected to the exterior shaft 18, such as, for example, by the threaded engagement of the internal thread 40 of the connector body 45 and the external thread 38 of the exterior shaft 18. Additionally, according to certain embodiments, the connector body 45 may be molded from a relatively stiff and/or rigid material, such as, for example, polyethylene or polypropylene, among other materials.

The sleeve 44 may be configured to provide a first cavity 48 and a second cavity 50. Additionally, the first and second cavities 48, 50 are in communication with each other and are configured to receive the movable insertion of the insert 42. The terms "first cavity" and "second cavity" may refer to physically distinct compartments (e.g., having an interruption, transition region, membrane or geometrical change between them, such as shown in FIG. 3) or alternatively a single compartment that is adapted to facilitate retaining an insert in a first position within the compartment (i.e., "first cavity") and then a second position within the same compartment (i.e., "second cavity"), with no interruption, transition region, membrane or geometrical change between the first cavity and second cavity.

The outer portion 46 of the sleeve 44 comprises a nose cone 92 (generally facing the syringe contents), and a sidewall 90 (generally facing the sidewall 58 of the barrel 56). The term "nose cone" 92 refers to the syringe contents-facing surface of the convertible plunger 12, and may be of any suitable geometry (e.g., rounded, cone-shaped, flat, etc.). The sidewall 90 of the sleeve 44 includes a storage sealing section 51 comprising at least one rib 52 that is preferably generally adjacent to and/or aligned with at least a portion of the first cavity 48. For example, as shown by at least FIG. 3, a single rib 52 of the storage sealing section 51 is generally adjacent to and/or aligned with the first cavity 48. However, the number of ribs 52 of the storage sealing section 51 aligned with and/or adjacent to the first cavity 48 may vary. Further, according to certain embodiments, a rib 52 of the storage sealing section 51 may not be positioned adjacent to and/or aligned with the second cavity 50. The sleeve 44 may be constructed from a thermoset rubber (e.g., butyl rubber) having good gas barrier properties, or a thermoplastic elastomer, among other materials. The purpose of the storage sealing section 51 is to provide CCI and optionally a barrier to one or more gases (e.g., oxygen) when the convertible plunger 12 is in a "storage mode," e.g., to seal the contents of a pre-filled syringe when in storage, prior to use. The gas barrier should effectively prevent ingress of gas(es) that may degrade the product contained within the syringe during the product's desired shelf life. The gas barrier should also effectively prevent egress of gas(es) that preferably remain within the product containing area 59 of the syringe. The particular gas(es) for which the storage sealing section 51 optionally provides a barrier when the plunger is in storage mode may vary depending on the product contained within the syringe. Optionally (in any embodiment), the gas barrier is an oxygen barrier. When the convertible plunger 12 is converted from storage mode to dispensing mode, the seal initially provided by the storage sealing section 51 is either reduced or removed entirely (i.e., such that the storage sealing section 51 no longer physically contacts the sidewall 58 of the barrel 56).

The insert 42 may also be constructed from a variety of different products, including products that allow the insert to have a lower, similar, or higher rigidity than/to the sleeve 44. Preferably, in any embodiment, the insert has a higher rigidity than the sleeve. Additionally, the insert 42 may have a variety of shapes and be generally configured to occupy at least one of the first and second cavities 48, 50. According to the embodiment illustrated in FIGS. 2-4, the insert 42 has a generally spherical shape. Alternative insert embodiments and shapes are disclosed below.

The sleeve 44, and particularly the rib 52 of the storage sealing section 51, and the insert 42 are configured to provide a force that compresses the rib 52 against the sidewall 58 of a barrel 56, as shown in FIG. 4. Such compression of the rib 52 of the storage sealing section against the sidewall 58 provides a seal, such as a compression seal in a "storage mode", between the convertible plunger 12 and the sidewall 58 that protects the sterility and/or integrity of injection product contained in the barrel 56. A typical compression may be, e.g., less than 10% of the overall width or diameter of the rib 52 and/or sleeve 44 when the convertible plunger 12 is compressed to form a seal in the barrel 56, optionally less than 9%, optionally less than 8%, optionally less than 7%, optionally less than 6%, optionally less than 5%, optionally less than 4%, optionally less than 3%, optionally less than 2%, optionally from 3% to 7%, optionally, from 3% to 6%, optionally from 4% to 6%, optionally from 4.5% to 5.5%, optionally from 4.5% to 5.5%, optionally about 4.8%. The compression is dependent on not only the geometric tolerances of the plunger and syringe barrel but also the material properties of the plunger (e.g., durometer of the rubber). Optionally, additional ribs 52 of the storage sealing section 51 may be included, which may increase the integrity of the seal and/or form separate seals between the plunger 12 and the sidewall 58 of the barrel 56. Embodiments having such additional ribs are illustrated in FIGS. 36-38A and described in detail below.

According to certain embodiments, the sleeve 44 and insert 42 are sized such that, when the plunger 12 is in the barrel 56 and the insert 42 is in the first cavity 48, the insert 42 prevents or minimizes a reduction in the size of the first cavity 48. Such minimizing or prevention of a reduction in size of the first cavity 48 may minimize the extent the size of the rib 52 of the storage sealing section 51, which is generally adjacent and/or aligned to/with the first cavity 48, may be reduced by engagement of the rib 52 with the sidewall 58 of the barrel 56. According to such embodiment, the rib 52 may be sized such that, with the support of the insert 44 in the first cavity 48, the rib 52 is large enough to be compressed between the sleeve 44 and the sidewall 58 to form the compression seal for storage mode of the plunger 12. Further, according to certain embodiments, the insert 42 may be configured to limit the compression of the rib 52 and/or sleeve 44 such that the rib 52 and/or sleeve 44 is compressed less than 20% of the overall width of the sleeve 44 when the plunger 12 is being used to form a seal during storage mode in the barrel 56. Optionally, the rib 52 and/or sleeve 44 are compressed less than 10% of the overall width or diameter of the rib 52 and/or sleeve 44 when the plunger 12 is compressed to form a seal in the barrel 56, optionally less than 9%, optionally less than 8%, optionally less than 7%, optionally less than 6%, optionally less than 5%, optionally less than 4%, optionally less than 3%, optionally less than 2%, optionally from 3% to 7%, optionally, from 3% to 6%, optionally from 4% to 6%, optionally from 4.5% to 5.5%, optionally from 4.5% to 5.5%, optionally about 4.8%.

Alternatively, according to other embodiments, the insert 42 may be sized to expand the size of the first cavity 48 and rib 52 of the storage sealing section 51 so as to provide sufficient support to push or force the rib 52 against the sidewall 58 to form the compression seal during storage mode of the plunger 12.

The plunger 12 may be positioned in the barrel 56 before or after the plunger 12 is connected to the exterior shaft 18. When injection product in the syringe barrel, such as in the product containing area 59 of the barrel 56, is to be dispensed from the barrel 56, a user may depress the actuator 26 to displace the interior shaft 16 from the first position to the second position, as previously discussed. In the embodiment shown in FIGS. 1-4, as the interior shaft 16 is displaced to the second position, the proximal end 22 of the interior shaft 16 may exit the first end 28 of the exterior shaft 18 and enter into the plunger 12. As the locking tab 24 is moved to the second recess 34, the interior shaft 16 may push the insert 42 from the first cavity 48 to the second cavity 50.

With the insert 42 in the second cavity 50, the support and/or force that the insert 42 had been providing/exerting upon the rib 52 of the storage sealing section 51 is reduced and/or removed. Thus, under such circumstances, the force previously exerted by the rib 52 against the sidewall 58 of the barrel 56 is also at least reduced, or preferably removed (i.e., with no contact between the rib 52 of the sealing section 51 and the sidewall 58 of the barrel 56 when the plunger 12 is in a "dispensing mode."). Additionally, according to certain embodiments, a rib 52 may not be generally adjacent to and/or aligned with the second cavity 50 of the sleeve 44 so that the presence of the insert 42 in the second cavity 50 is not supporting or pushing a different rib 52 against the sidewall 58. Thus, with the force that had been exerted by the rib 52 against the sidewall 58 being removed or reduced by the displacement of the insert 42 to the second cavity 50, the force needed to displace the plunger 12 along the barrel 56 is less than the force would have been had the insert 42 remained in the first cavity 48. Thus, the force that had been exerted against the sidewall 58 by the plunger 12 is adjusted, and more specifically reduced, when the plunger 12 is to be displaced for dispensing of the injection product. Moreover, the extent of the force reduction is such that the injection product may be pushed completely forward out of the syringe against the back pressure caused by the viscosity of the injection product and/or the needle gauge. With the insert 42 in the second cavity 50 and the interior shaft 16 in the second position, the plunger assembly 10 may be displaced to reduce the size of the product containing area, and thereby dispense the injection product from the barrel 56.

Additionally, according to certain embodiments, the plunger 12 may optionally be configured such that when the first cavity 48 is not occupied by the insert 42, the rib 52 nonetheless maintains contact with the sidewall 58 of the barrel 56. Moreover, under such conditions, the rib 52 may be configured to provide a wiper surface to assist in the removal of injection product from the barrel 56 as the plunger assembly 10 is displaced during administration/dispensing of the injection product.

Optionally, the outer portion 46 of the sleeve 44 may include a liquid sealing section 53, preferably on the sidewall 90 of the sleeve 44, optionally adjacent to, distal to or otherwise near to the nose cone 92. The liquid sealing section 53 comprises at least one rib 55 of the liquid sealing section 53. The purpose of the liquid sealing section 53 is to provide a liquid tight seal both when the plunger 12 is in a storage mode as explained above, and when the plunger is transitioned into a "dispensing mode," i.e., when the storage sealing section 51 reduces or ceases compressive force against the barrel wall 58 so as to facilitate advancement of the plunger to dispense the contents of the syringe. Optionally, the liquid sealing section 53 may also provide CCI. Preferably, there is a valley 57 separating the storage sealing section 51 from the liquid sealing section 53.

Figure 36:
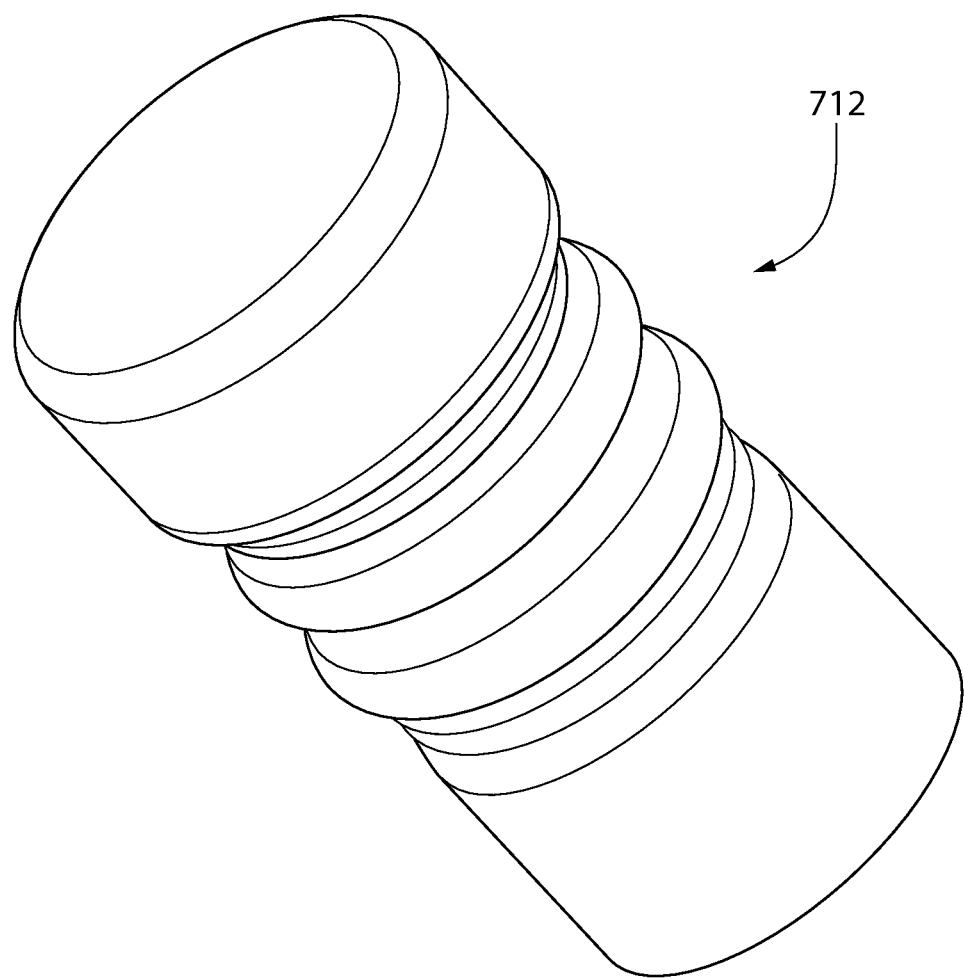
FIG. 36 illustrates a perspective view of an alternative plunger having a two-rib sealing section.
Figure 37:
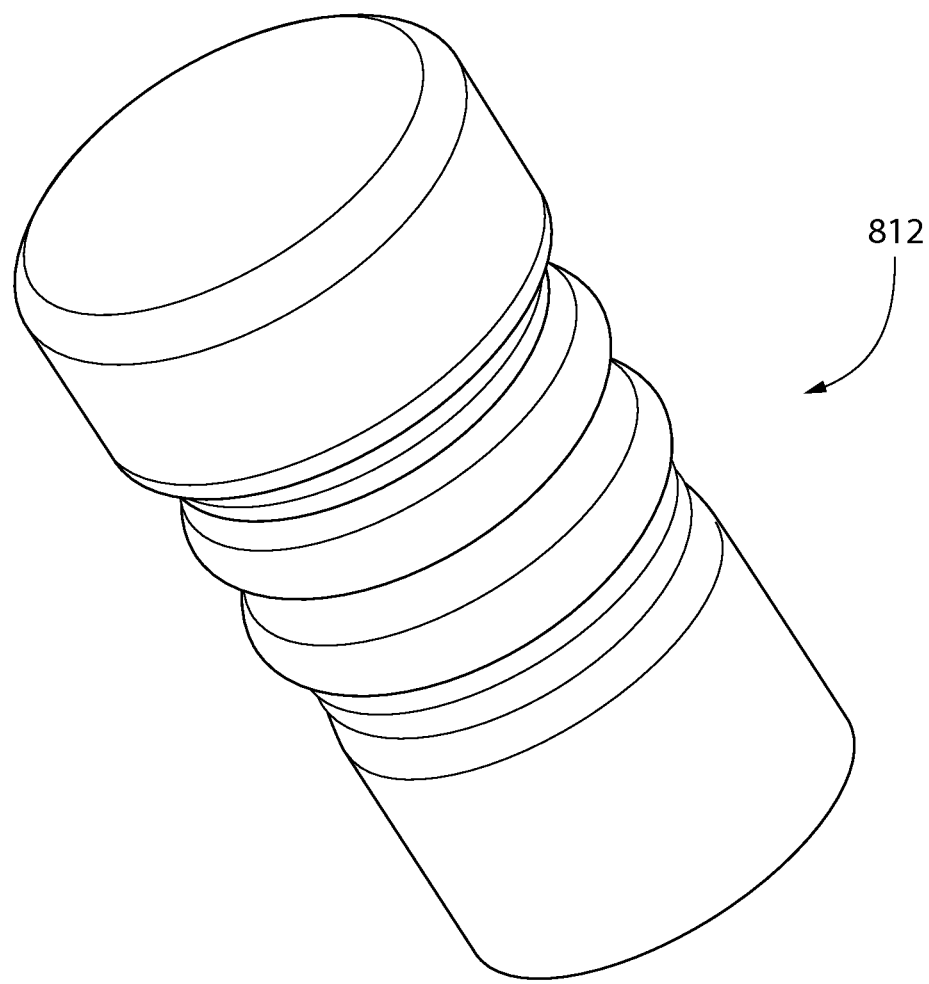
FIG. 37 illustrates a perspective view of an alternative plunger having a two-rib sealing section.
Figure 37A:
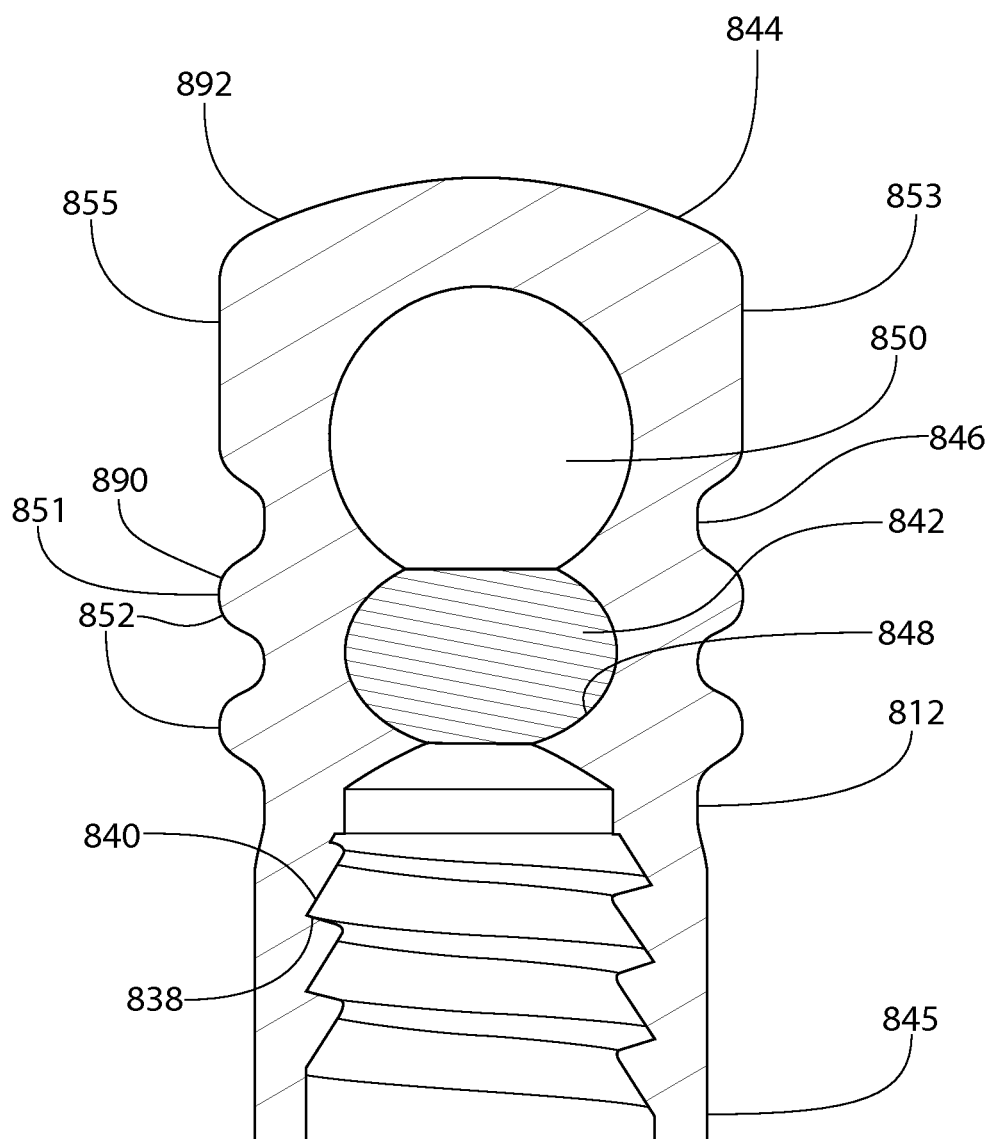
FIG. 37A illustrates an axial sectional view of the plunger shown in FIG. 37.

FIGS. 36-38A show three alternative optional embodiments of convertible plungers 712, 812, 912, according to aspects of the present invention, wherein each of the plungers 712, 812, 912 comprise more than one rib 752, 852, 952 of a respective plunger's storage sealing section 751, 851, 951. As shown in FIGS. 36-37A, for example, the plungers 712, 812 each include two ribs 752, 852 in their respective storage sealing sections 751, 851. In an optional alternative of a convertible plunger 912 shown in FIGS. 38 and 38A, the storage sealing section 951 of the plunger 912 includes three ribs 952.

In certain respects, the plungers 712, 812, 912 include some structural components substantially similar to the plunger 12 of FIGS. 1-4 and in certain respects operate in a substantially similar manner to the plunger 12. For example, a plunger's connector body 745, 845, 945 may be configured to be connected to an exterior shaft of a plunger rod, such as, for example, by the threaded engagement of an internal thread 740, 840, 940 of the connector body 745, 845, 945 and the external thread 738, 838, 938 of a respective exterior shaft. Much of the discussion above concerning the structure and function of the plunger 12 of FIGS. 1-4 is equally applicable to the plungers 712, 812, 912 and thus will not be repeated here in full. The following is a non-limiting summary of some structural features of the plungers 712, 812, 912.

The plunger 712, 812, 912 includes an insert 742, 842, 942, a sleeve 744, 844, 944 and a connector body 745, 845, 945. The connector body 745, 845, 945 may be operably connected to the sleeve 744, 844, 944 in any such manner described herein with respect to the plunger 12 of FIGS. 1-4. Likewise, the connector body 745, 845, 945 may be connected to a plunger rod in any such manner described herein with respect to the plunger 12 of FIGS. 1-4.

The sleeve 744, 844, 944 may be configured to provide a first cavity 748, 848, 948 and a second cavity 750, 850, 950, which are in communication with each other and are configured to receive the movable insertion of the insert 742, 842, 942. The outer portion 746, 846, 946 of the sleeve 744, 844, 944 comprises a nose cone 792, 892, 992 and a sidewall 790, 890, 990. The sidewall 790, 890, 990 of the sleeve 744, 844, 944 includes a storage sealing section 751, 851, 951 comprising ribs 752, 852, 952 that are preferably generally adjacent to and/or aligned with at least a portion of the first cavity 748, 848, 948. As with the plunger 12 of FIGS. 1-4, the storage sealing section 751, 851, 951 of a respective plunger 712, 812, 912 is configured (when in storage mode) to provide CCI and optionally a barrier to one or more gases. When the convertible plunger 712, 812, 912 is converted from storage mode to dispensing mode, the seal initially provided by the storage sealing section 751, 851, 951 is either reduced or removed entirely (i.e., such that the storage sealing section 751, 851, 951 no longer physically contacts the sidewall of a syringe barrel in which the plunger 712, 812, 912 is disposed).

Optionally, the outer portion 746, 846, 946 of the sleeve 744, 844, 944 may include a liquid sealing section 753, 853, 953 preferably on the sidewall 790, 890, 990 of the sleeve 744, 844, 944 optionally adjacent to, distal to or otherwise near to the nose cone 792, 892, 992. The liquid sealing section 753, 853, 953 comprises at least one rib 755, 855, 955 of the liquid sealing section 753, 853, 953. The purpose of the liquid sealing section 753, 853, 953 is to provide a liquid tight seal both when the plunger 712, 812, 912 is in storage mode and when the plunger is transitioned into dispensing mode. Optionally, the liquid sealing section 753, 853, 953 may also provide CCI. Preferably, there is a valley separating the storage sealing section 751, 851, 951 from the liquid sealing section 753, 853, 953.

Figure 38:
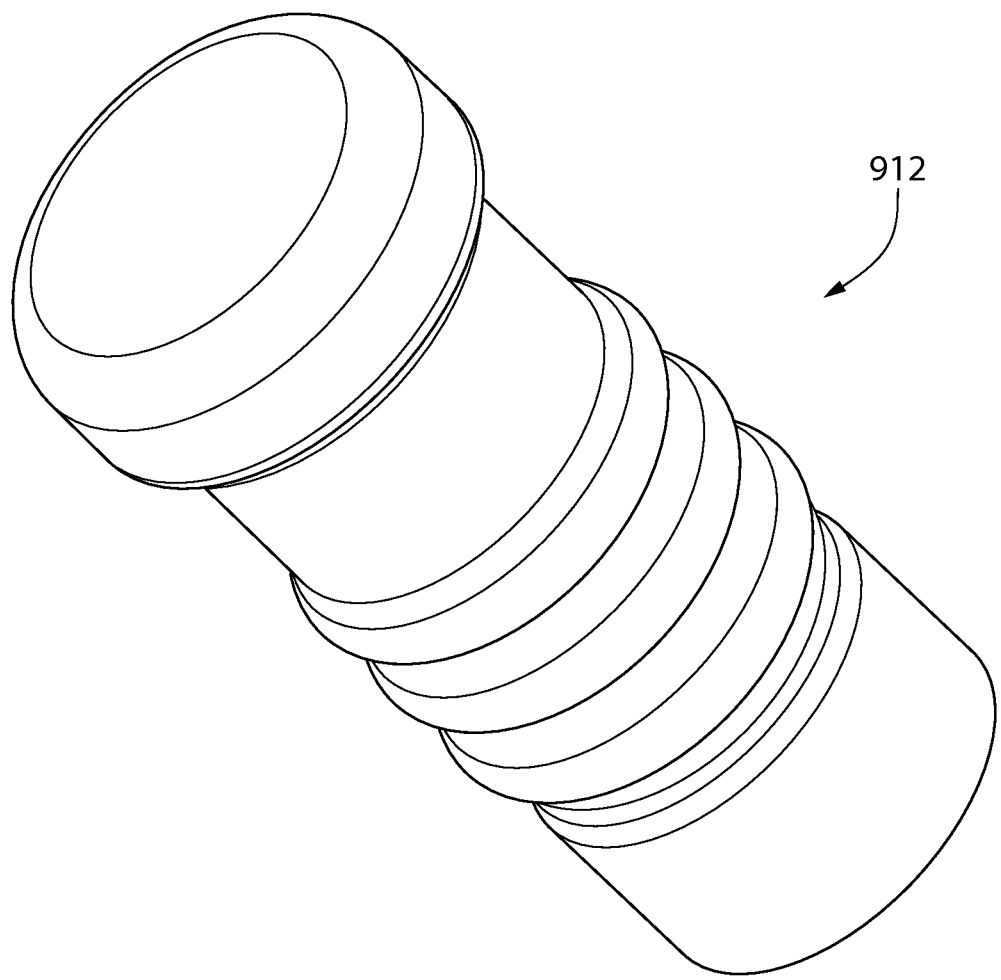
FIG. 38 illustrates a perspective view of an alternative plunger having a three-rib sealing section.
Figure 38A:
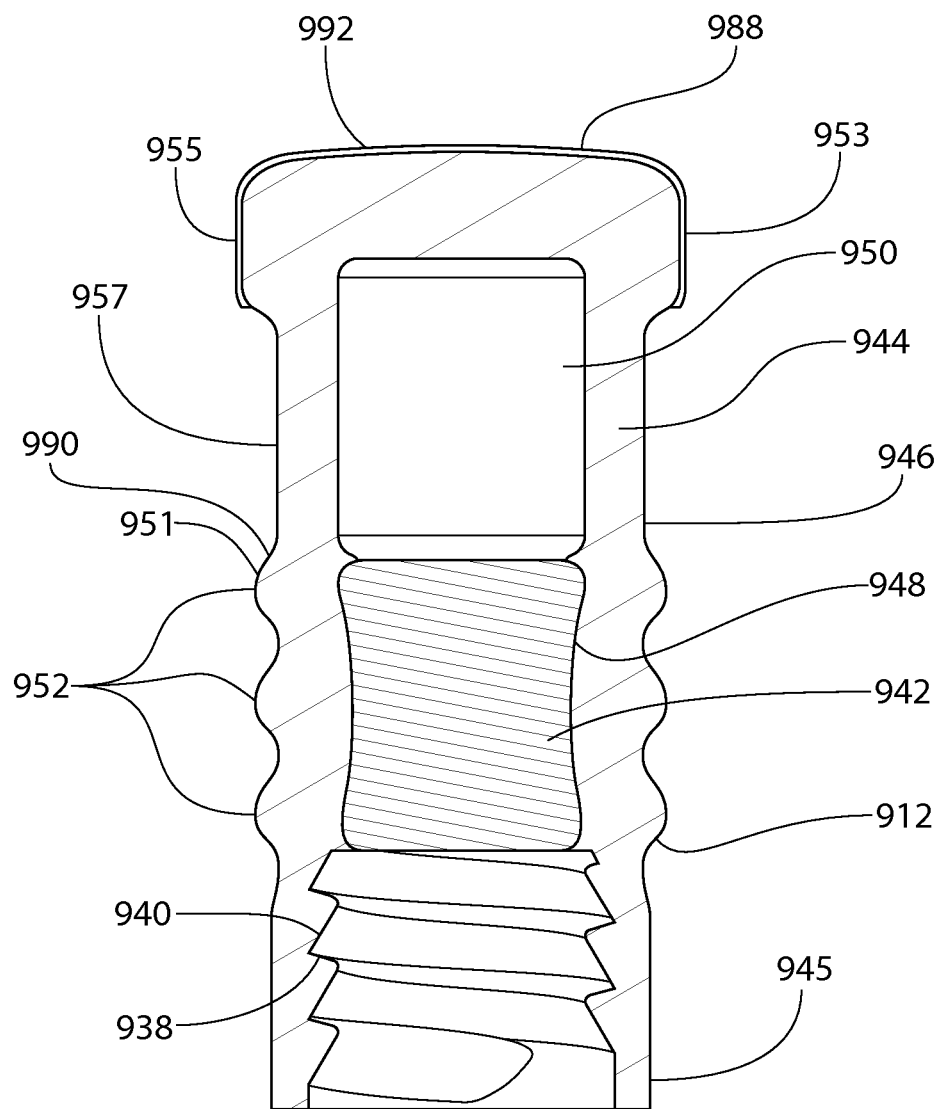
FIG. 38A illustrates a sectional view of an alternative plunger shown in FIG. 38.

Optionally, a film coating or cap is applied to a portion of the plunger sleeve 744, 844, 944. While any plunger embodiment of the present invention (e.g., 712, 812, 912) may include such a film or cap, the plunger 912 of FIGS. 38 and 38A as illustrated includes a film coating 988 mounted over the nose cone 992 and a portion of the sidewall 990 of the film coated plunger 912. Preferably, as shown, the film coating 988 covers the entire nose cone 992. The film coating 988 also optionally covers the rib 955 of the liquid sealing section 953 and optionally a small section of the valley adjacent to the rib 955. Optionally, as shown in FIG. 38A, the valley of the plunger 912 comprises a descending slope extending distally from the liquid sealing section 953, the descending slope leading to a floor, the floor leading to an ascending slope toward the storage sealing section 951. As illustrated, the film coating 988 terminates towards the beginning of the descending slope of the valley. Optionally, the film coating 988 terminates before the storage sealing section, optionally before the ascending slope, optionally before the floor. In any event, there is preferably no film coating 988 covering any of the ribs 952 of the storage sealing section 951. The film coating 988 may be made, e.g., from any materials disclosed elsewhere in this specification with regard to the film coating 88 or film 94 (see, e.g., FIGS. 8-10 and 26).

Figure 36A:
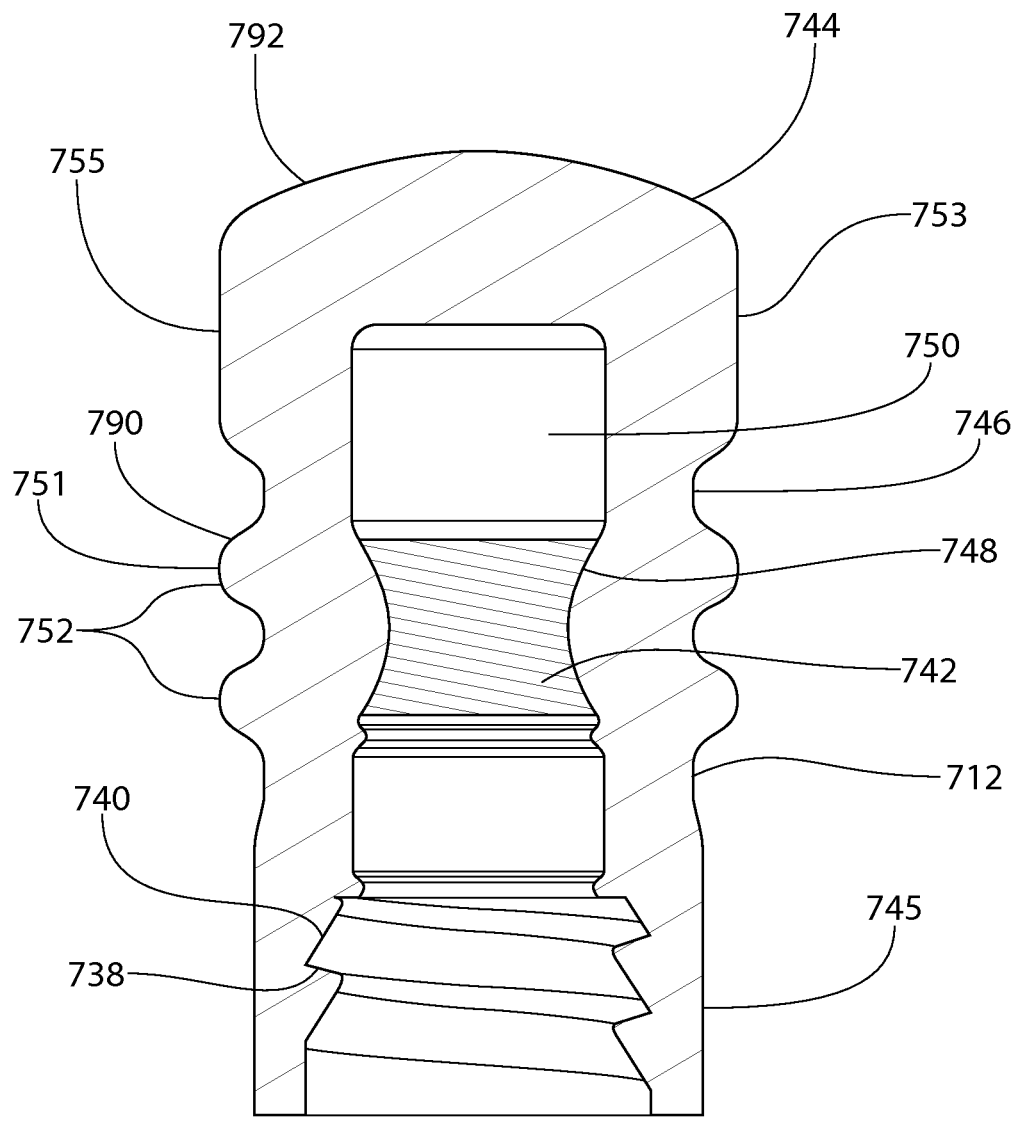
FIG. 36A illustrates an axial sectional view of the plunger shown in FIG. 36.

As discussed throughout this specification, an optional feature of convertible plungers according to the present invention is an insert which may be configured to provide outward radial pressure on a rib(s) of the liquid sealing section when the plunger is in storage mode. Such inserts may come in a variety of materials, shapes and configurations. For example, the insert 842 of plunger 812 is generally spherical. When the insert 842 is not in the cavity 848, the cavity 848 optionally has a reduced volume which is expanded (as shown in FIG. 37A) by radial pressure the insert 842 applies on the sleeve 844 when the insert 842 is retained therein. The inserts 742 and 942 of plungers 712 and 912 are generally cylindrical with a slight concavity around the periphery of the sidewall of a respective insert. The central axes of the generally cylindrical inserts 742 and 942 are optionally positioned parallel to or preferably in alignment with the central axis of a respective plunger 712, 912. Optionally, the inner walls of the first cavity include a slightly convex cylindrical outline (see FIGS. 36A and 38A) that provides complementary mating geometry to the slightly concave (around its periphery) sidewall of the insert 742, 942. Such mating geometry may help the insert 742, 942 to find its "home" position within the first cavity during assembly of the plunger 742, 942 and thereafter retain the insert 742, 942 in that position until the plunger 712, 912 is transitioned from storage mode to dispensing mode.

It is contemplated that the shape, material and positioning of an insert may be configured to provide a desired level of radial pressure distribution (e.g., even, concentrated in one or more places, in one or more directions, etc.).

While a single sealing rib (e.g., 52) on a convertible plunger is within the scope of the present invention, it is contemplated that two sealing ribs (e.g., 752, 852) or three sealing ribs (e.g., 952) would better ensure the integrity of the seal.

As discussed above, the embodiment of the plunger assembly 10 shown in FIGS. 1-4 comprises a sleeve 44 having two cavities in communication with each other—a first cavity 48 and a second cavity 50. As shown in FIGS. 1-4, the initial position of the insert 42 is in the first cavity 48, which compresses the rib 52 of the storage sealing section 51 against the sidewall 58 of the barrel. This positioning of the insert 42 configures the plunger 12 in storage sealing mode, as discussed above. During assembly of the syringe, depending on the method used, it may be difficult to insert the plunger 12 into the barrel 56 while the plunger 12 is in storage mode configuration. This is due to the compressive seal the plunger 12 provides while in storage mode.

Figure 31:
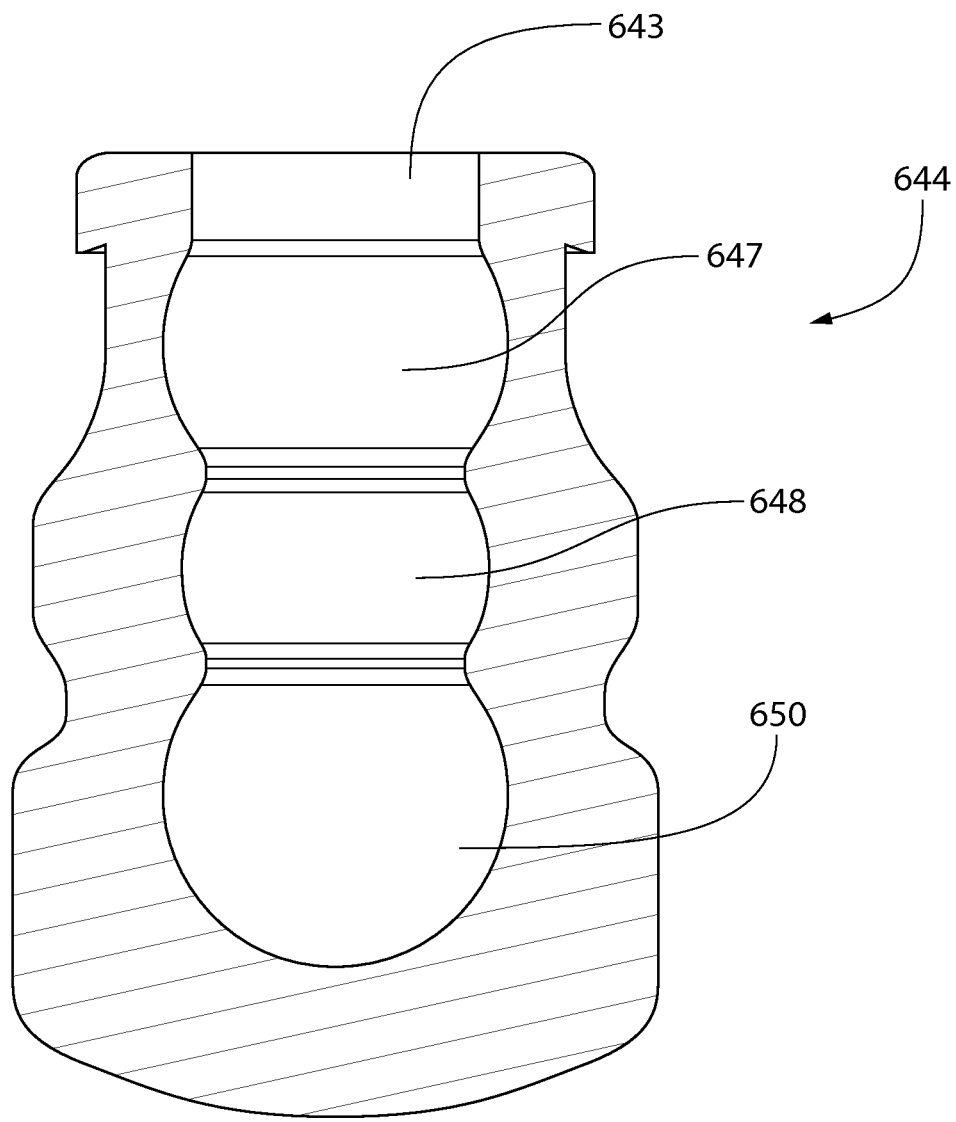
FIG. 31 illustrates a sectional view of an exemplary embodiment of plunger sleeve of a three-position plunger.

Accordingly, in another aspect, the invention is directed to convertible plunger assemblies configured to facilitate insertion of a plunger into a barrel, e.g., during assembly of a pre-filled syringe. Referring now to FIGS. 31-35, there is shown an alternative convertible plunger, in this case a three-position plunger 612. As shown in FIG. 31, the three position plunger comprises a sleeve 644 optionally configured to provide an opening 643 at a distal end thereof, a pre-load cavity 647 proximal to the opening, a first cavity 648 proximal to the pre-load cavity 647 and a second cavity 650 proximal to the first cavity 648. As shown, the pre-load cavity 647 is in communication with the first cavity 648, which in turn, is in communication with the second cavity 650. Aside from the presence of the pre-load cavity 647, the plunger sleeve 644 may be otherwise substantially identical to the sleeve 44 of the plunger 12 shown in FIGS. 1-4.

Figure 32:
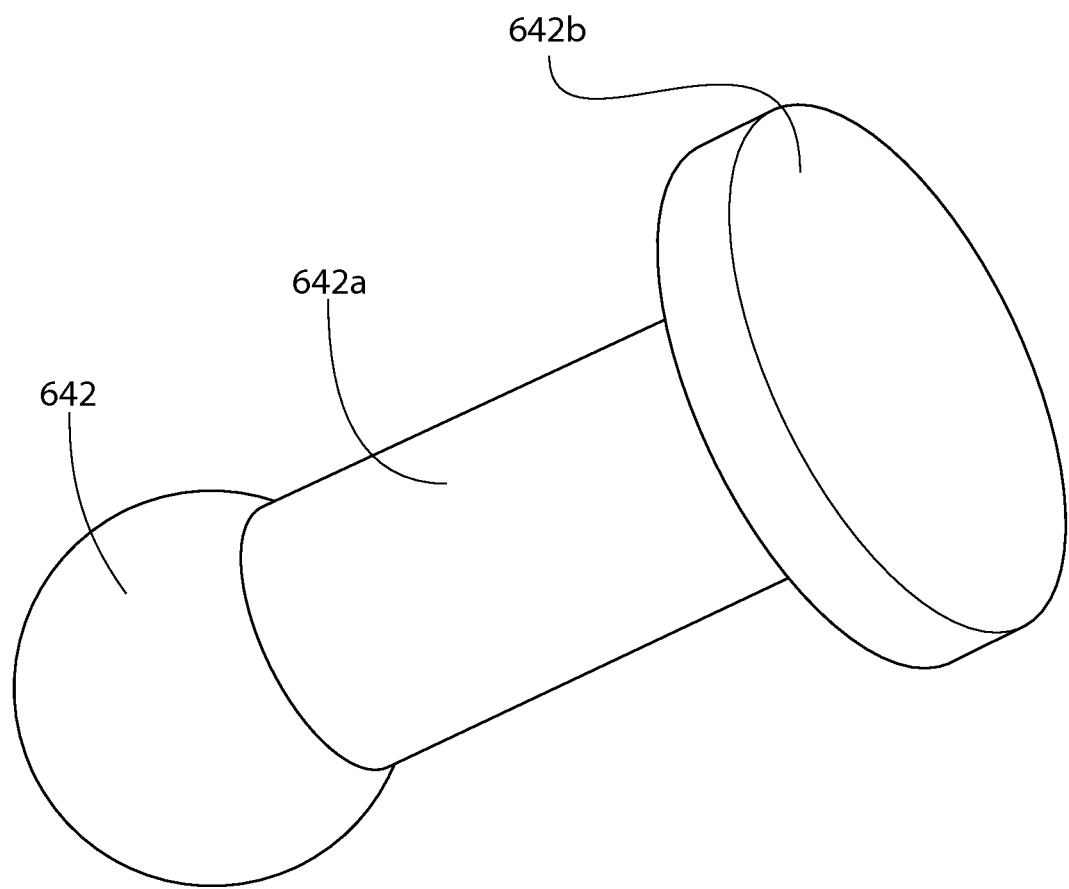
FIG. 32 illustrates a perspective view of an exemplary embodiment of an insert configured for use with the three-position plunger sleeve of FIG. 31.

The cavities 647, 648, 650 are configured to receive the movable insertion of an insert. An isolated view of the insert 642 which may be used with the three-position plunger 612, is shown in FIG. 32. The insert 642 resembles the gripping portion of a ball knob. The insert 642 may be generally partially spherical in shape—"partially" because the insert 642 is secured to or integral with an insert shaft 642a, which interrupts the otherwise spherical geometry of the insert 642. The insert shaft 642a is secured to or integral with an insert flange 642b. Optionally, the insert flange 642b does not need to be a different diameter than the insert shaft 642a. The insert flange 642b may optionally protrude from the sleeve 644 when the insert 642 is disposed in the pre-load cavity 647 and the first cavity 648. This feature would enable one to visually observe the position of the insert to confirm its position in the sleeve 644. By looking at the syringe or measuring the position of the insert flange 642b, one may readily determine whether the insert 642 is disposed in the pre-load cavity 647 or the first cavity 648, as a way of doing a quality check or confirmation.

Figure 33:
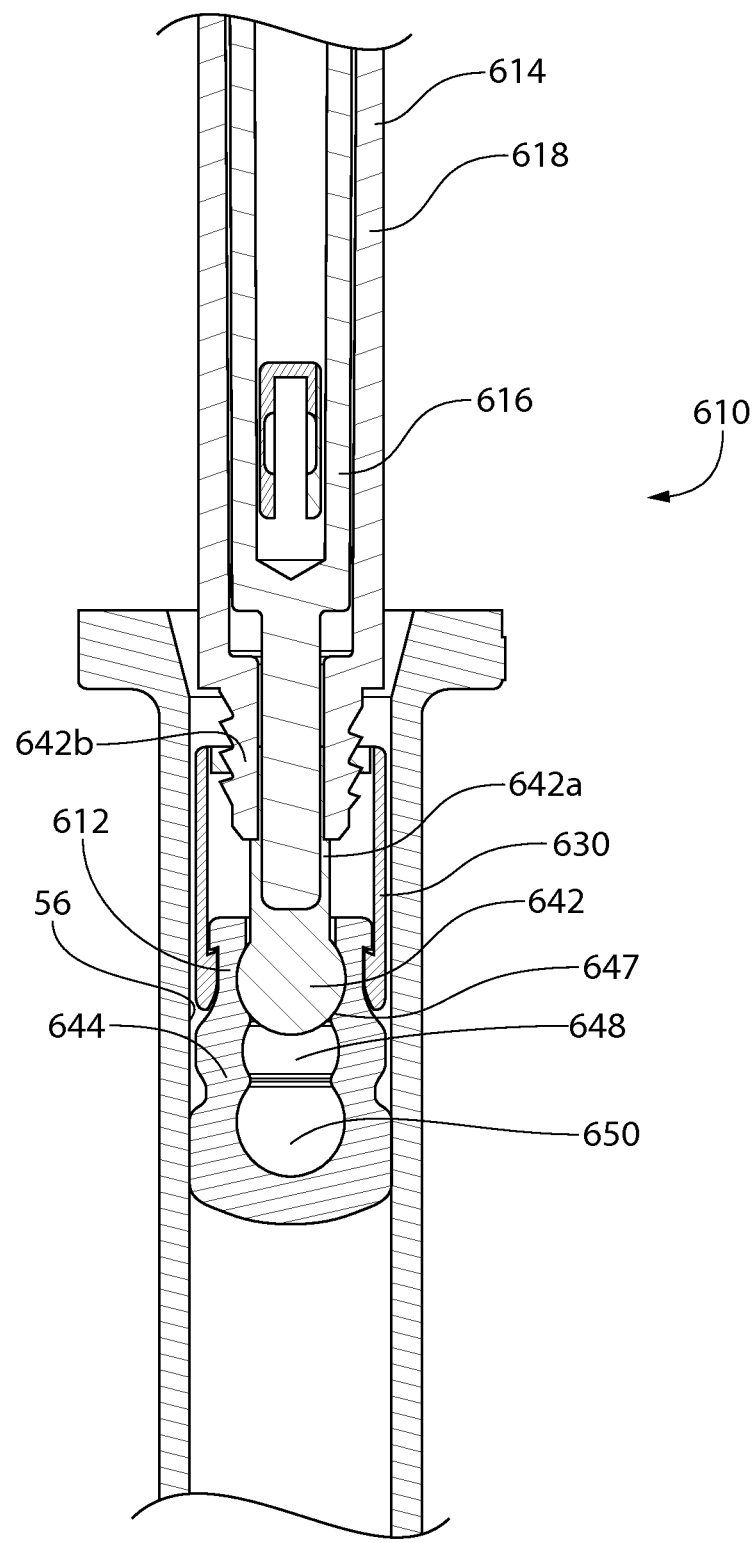
FIG. 33 illustrates a partial sectional view of a syringe comprising a plunger assembly using the plunger sleeve of FIG. 31 and insert of FIG. 32, with the plunger in pre-load mode.

Referring to FIG. 33, there is shown a partial cross-sectional view of a barrel 56 having a three-position plunger assembly 610 inserted therein. The plunger assembly 610 includes a three position plunger 612 and plunger rod 614. The plunger rod 614, which comprises an interior shaft 616 and exterior shaft 618, connects to the plunger 612 and operates substantially as described above with respect to the plunger assembly 10 of FIGS. 1-4. In brief, the internal shaft 616 is movable in a proximal direction relative to the external shaft 618 to press against the insert flange 642b and thereby drive the insert 642 from its initial position, i.e., within the pre-load cavity 647, to the first cavity 648 and finally to the second cavity 650.

The three-position plunger 612 further comprises a round collar 630 secured thereto. The round collar 630 is preferably formed from plastic or another material having a greater rigidity than the plunger material. Optionally, the pre-load cavity is generally aligned with at least a portion of the round collar 630. Optionally, the round collar is in the form of a collapsible c-ring. The round collar 630 protects the plunger, reduces the amount of exposed rubber of the plunger, provides guidance for smooth travel of the plunger 612, and provides a rigid surface for the plunger rod 614 to press against when actuating the plunger 612.

Figure 34:
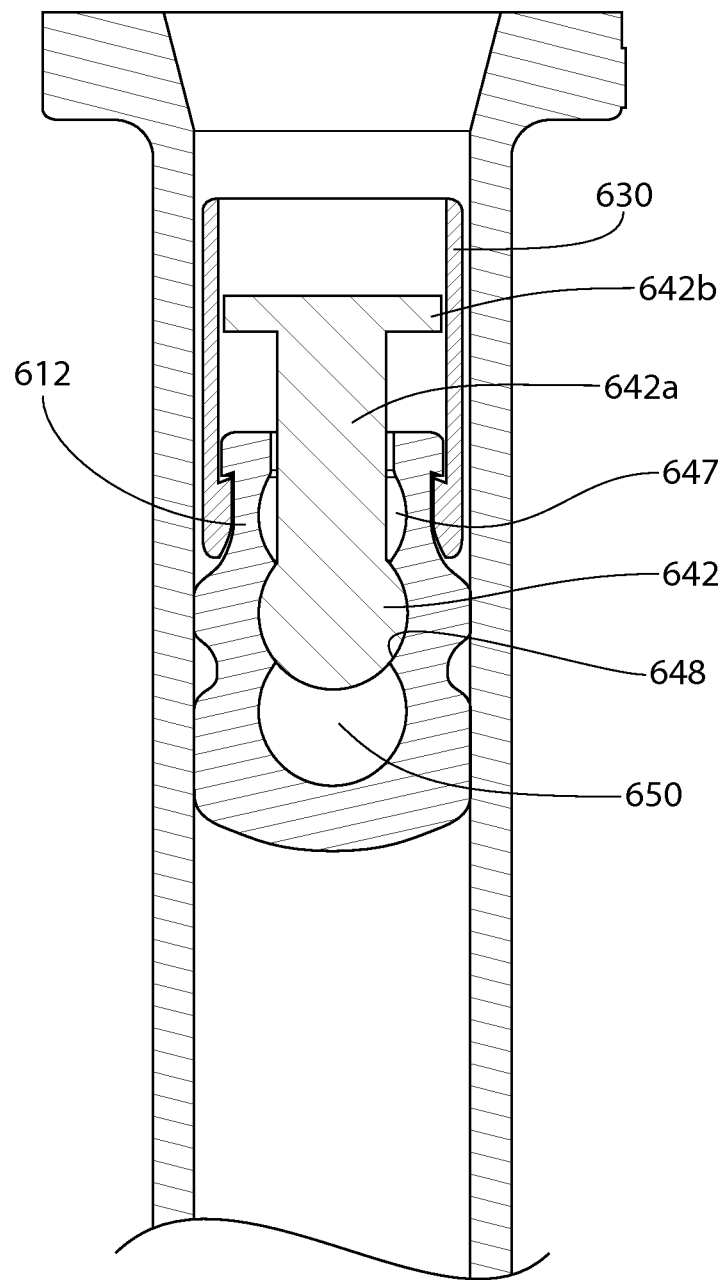
FIG. 34 illustrates a partial sectional view of the syringe of FIG. 33 with the plunger in storage mode.
Figure 35:
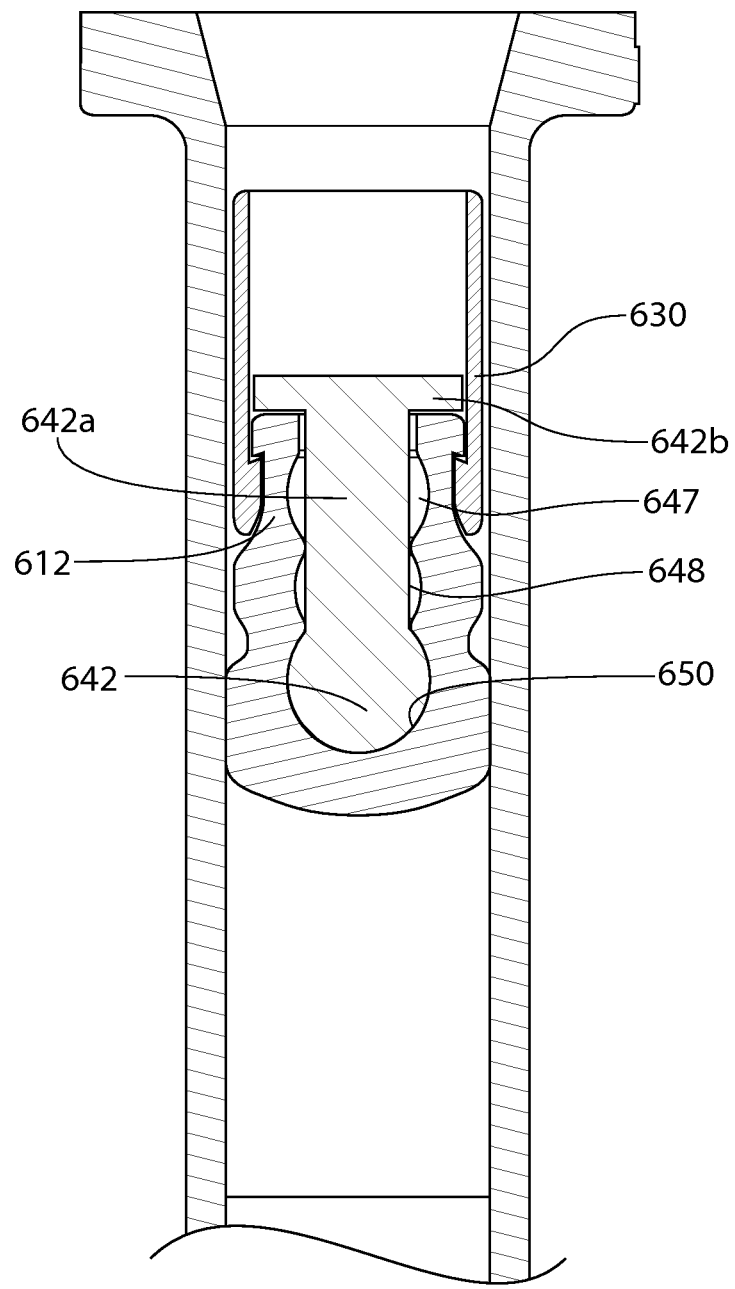
FIG. 35 illustrates a partial sectional view of the syringe of FIG. 34 with the plunger in dispensing mode.

In use, a syringe may be assembled by providing the plunger 612, with the insert 642 pre-inserted into the pre-load cavity 647 of the three-position plunger 612. The external profile of the plunger and/or compressive force or radial pressure the plunger exerts against the barrel 56 is unaffected by disposal of the insert 642 in the pre-load cavity 647. Accordingly, the plunger 612 may be inserted into the barrel 56 with relative ease. Once the plunger 612 is sufficiently inserted into the barrel 56 with the insert disposed in the pre-load cavity 647 (i.e., in "pre-load mode"), the insert 642 may be advanced into the first cavity 648 by applying downward pressure on the insert 642. Once the insert 642 is disposed in the first cavity 648, the plunger 612 is then in storage mode. The plunger will then remain in storage mode until it is time to use the syringe. As described above, transition from the first cavity to the second cavity converts the plunger from a use mode configuration to a dispensing mode configuration. For clarity, FIG. 34 shows the insert 642 disposed in the first cavity 648 and FIG. 35 shows the insert 642 disposed in the second cavity 650. Optionally, the insert provides a visual indicator showing externally in which cavity the insert 642 is disposed at a given time, as explained above. This indication can be confirmed by observations or vision inspection to verify that the insert is properly positioned, i.e., either in pre-load mode or storage mode.

Optionally, the plunger rod 614 can be added to the filled syringe at a later time. All of the functions of the plunger 612 and insert 642 are self-contained. The plunger rod 614 or other means may optionally be used to axially displace the insert 642.

Optionally, a two-position plunger configuration may be employed wherein the second cavity functions both as a pre-load cavity for retaining an insert in preload mode and as a second cavity for retaining the insert in dispensing mode, as disclosed above. For such an embodiment, the insert may be reversibly axially displaceable between second and first cavities more than one time. In this way, the insert may be pre-inserted into the pre-load cavity such that the external profile of the plunger and/or compressive force or radial pressure the plunger exerts against a syringe barrel is unaffected by disposal of the insert in the pre-load cavity. Accordingly, the plunger may be inserted into the barrel with relative ease. Once the plunger is sufficiently inserted into the barrel with the insert disposed in the pre-load cavity in pre-load mode, the insert may be retracted axially into the first cavity by applying upward or pulling pressure on the insert. Once the insert is disposed in the first cavity, the plunger is then in storage mode. The plunger will then remain in storage mode until it is time to use the syringe. To transition the plunger into dispensing mode, downward pressure is applied to the insert to displace it into the second cavity. In this particular embodiment, the presence of the insert in the second cavity places the plunger in both insertion mode and dispensing mode (which mode depends on the action at a given moment that the plunger is intended to facilitate, i.e., insertion or dispensing).

Figure 6:
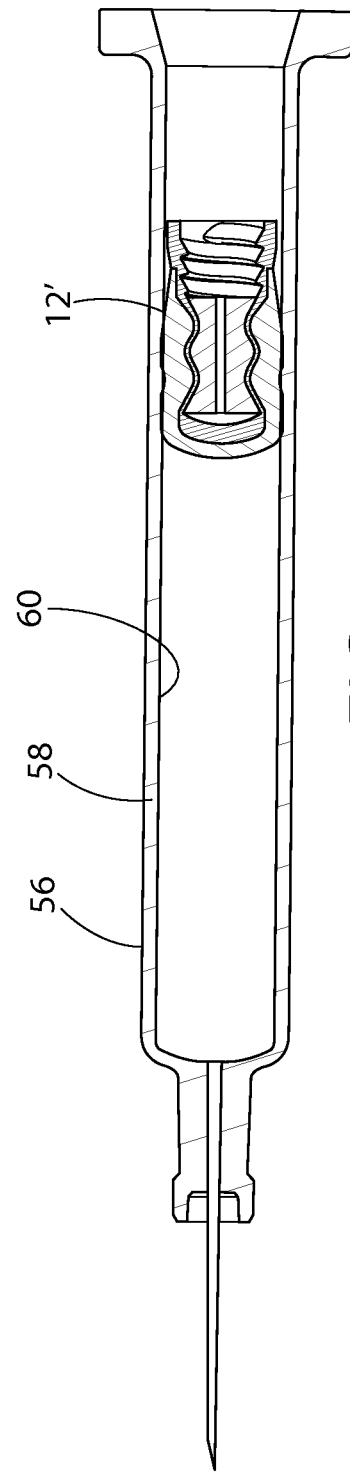
FIG. 6 illustrates a partial sectional view of the plunger shown in FIG. 5 positioned within a barrel of a syringe.
Figure 7:
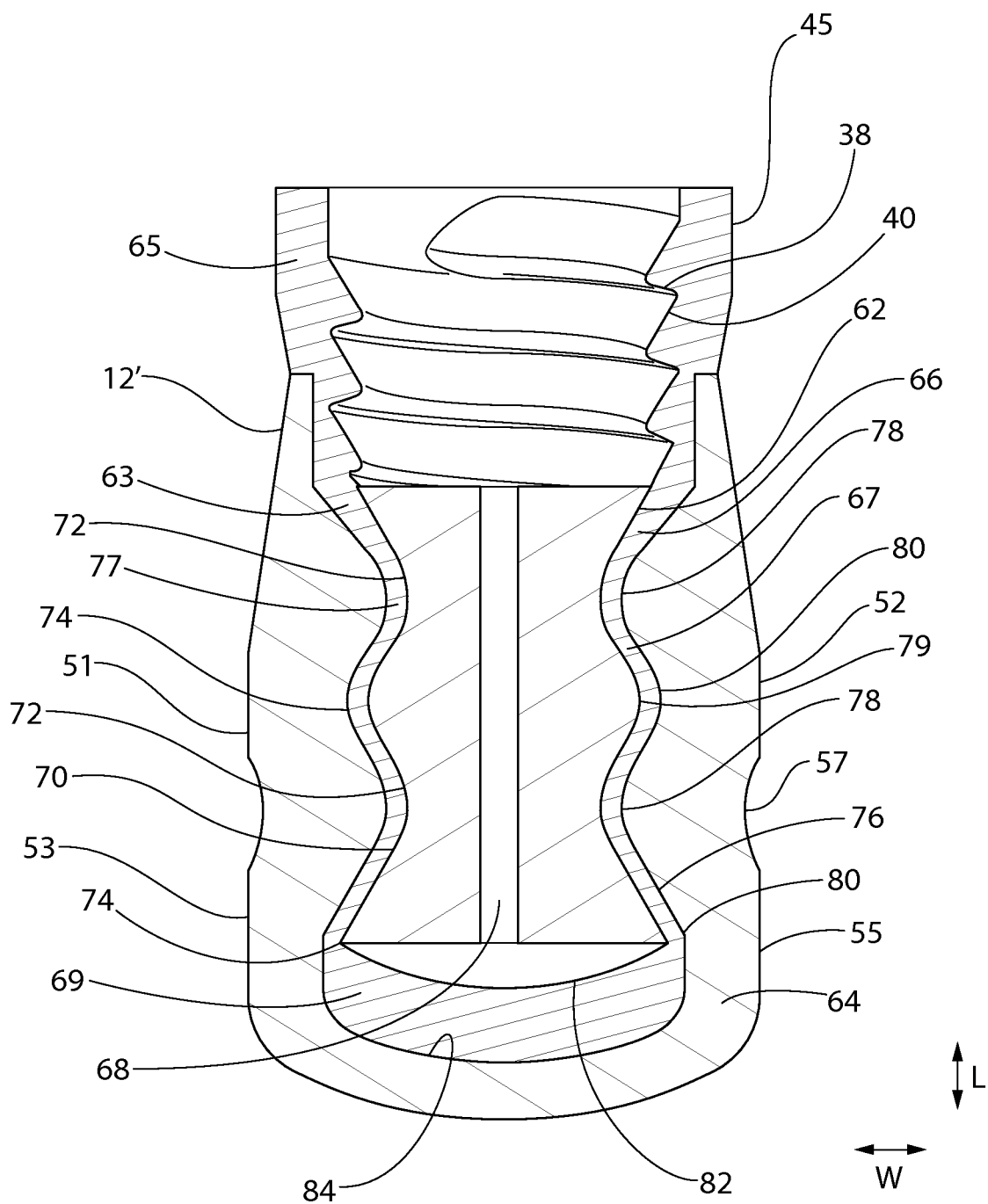
FIG. 7 illustrates an isolated partial sectional view of the plunger shown in FIGS. 5 and 6.

FIGS. 5-7 illustrate an alternative embodiment of the plunger assembly 10, and in particular, an alternative plunger 12'. The plunger 12' includes an insert 62, a connector body 63, and a sleeve 64. As shown in FIG. 5, according to certain embodiments, the sleeve 64 includes a cavity 66 configured to receive placement of the proximal end 22 of the interior shaft 16. The insert 62 may also include a relatively rigid shaft 68 that assists in the displacement of the insert 62 and/or deformation of the plunger 12', as discussed below.

According to certain embodiments, the connector body 63 may be molded from a relatively stiff and/or rigid material, such as, for example, polyethylene or polypropylene. Additionally, the connector body 63 may have a first section 65, a second section 67, and a third section 69. The first section 65 of the connector body 63 is configured for a connectable engagement with the exterior shaft 18. For example, as shown by at least FIG. 7, the first section 65 may include an internal thread 40 that mates with an external thread 38 of the exterior shaft 18.

According to certain embodiments, the second section 67 of the connector body 63 may provide an internal structure in the plunger 12' that minimizes and/or prevents a reduction in the size, such as the width (as indicated by "W" in FIG. 7) of the sleeve 64 when the plunger 12' is inserted into the barrel 56. According to such an embodiment, the sleeve 64 may be sized such that, when the plunger 12' is positioned in the barrel 56, the sleeve 64 is compressed, with the support of the second section 67, between the sidewall 58 of the barrel 56 and the second section 67 of the connector body 63. Such compression of the sleeve 64 may result in the formation of a seal, such as, for example, a compression seal, between the plunger 12' and the barrel 56 that may be used to maintain the sterility and/or integrity of an injection product stored in the barrel 56. In addition to the second section 67 of the connector body 63, according to certain embodiments, the insert 62 may also be configured to provide support to the sleeve 64 and/or connector body 63 when the plunger 12' is inserted into a barrel 56.

Further, according to certain embodiments, one or more ribs 52 of a storage sealing section 51 may extend from the sleeve 64 and be compressed against the sidewall 58 of the barrel 56 to provide CCI during when the plunger is in a "storage mode," e.g., to seal the contents of a pre-filled syringe when in storage, prior to use. The plunger 12' may further include a liquid sealing section 53 comprising at least one rib 55 of the liquid sealing section 53. The purpose of the liquid sealing section 53 is to provide a liquid tight seal both when the plunger 12 is in a storage mode as explained above, and when the plunger is transitioned into a "dispensing mode," i.e., when the storage sealing section 51 reduces or ceases compressive force or radial pressure against the barrel wall 58 so as to facilitate advancement of the plunger to dispense of the contents of the syringe. Preferably, there is a valley 57 separating the storage sealing section 51 from the liquid sealing section 53.

Alternatively, according to optional embodiments, each rib 52, 55 may form a separate seal when compressed against the sidewall 58 of the barrel 56. For example, in the embodiment illustrated in FIGS. 5-7, the sleeve 64 includes two ribs 52, 55 that may be used to form a seal(s) between the sidewall 58 of the barrel 56 and the sleeve 64. Further, according to certain embodiments, the second section 67 and/or insert 42 may be configured to limit the compression of the rib 52 and/or sleeve 64 such that the rib 52 and/or sleeve 64 are not compressed more than 20% of the overall width or diameter of the rib 52 and/or sleeve 64 when the plunger 12' is compressed to form a seal in the barrel 56. Optionally, the rib 52 and/or sleeve 64 are compressed less than 10% of the overall width or diameter of the rib 52 and/or sleeve 64 when the plunger 12' is compressed to form a seal in the barrel 56, optionally less than 9%, optionally less than 8%, optionally less than 7%, optionally less than 6%, optionally less than 5%, optionally less than 4%, optionally less than 3%, optionally less than 2%, optionally from 3% to 7%, optionally, from 3% to 6%, optionally from 4% to 6%, optionally from 4.5% to 5.5%, optionally from 4.5% to 5.5%, optionally about 4.8%.

The third section 69 of the connector body 63 may provide a surface upon which the insert 62 may exert a force against to elongate the length (as indicated by the "L" direction in FIG. 7), and thereby reduce the width ("W") of, the plunger 12' when injection product is to be dispensed from the barrel 56, as discussed below.

According to certain embodiments, the outer surface 70 of the insert 62, the second section of the connector body 53, and the inner surface 76 of the sleeve 64 may have a plurality of recesses 72, 77, 80 and protrusions 74, 78, 79 as shown in FIG. 7. Moreover, shape provided by the recesses 72 and protrusions 74 of the insert 62 may be generally be followed by the recesses 77 and protrusions 79 of the connector body 63, which are generally followed by the recesses 80 and protrusions 78 of the sleeve 64. Such recesses 72, 77, 80 and protrusions 74, 78, 79 may assist in maintaining the insert 62 in a sealing position in the barrel 56. Moreover, as shown for example in FIG. 7, the recesses 72, 77, 80 and protrusions 74, 78, 79 may provide obstacles that prevent the premature displacement of the insert 62. Such an accordion shaped configuration may also assist in the elongation of the plunger 12', and in particular the second section 67 of the connector body 53 and the sleeve 64 when the plunger 12' is to be displaced in the barrel 56 from a deactivated position, as shown in FIG. 7, to an activated position that elongates the length of the sleeve 64.

More specifically, when the injection product is to be dispensed from the barrel 56, the interior shaft 16 may be displaced from the first position, as shown in FIG. 5, to a second position, as previously discussed. As the interior shaft 16 is displaced toward the second position, the proximal end 22 of the interior shaft 16 exerts a pushing force upon an insert 62, such as, for example, upon the shaft 68 of the insert 62. As the interior shaft 16 exerts a force upon the insert 62, the insert 62 is displaced within the sleeve 64 generally in the direction of the proximal end 61 of the barrel 56, and thus at least a portion of the outer surface 70 of the insert 62 pushes against the third section 69 of the connector body 63. As the insert 62 is displaced and presses upon the third section 69, the second section 67 of the connector body 63 is elongated, thereby changing the prior accordion shape of the second section 67 to a generally straighter or flatter configuration. Additionally, the sleeve 64 is also elongated by this displacement of the insert 62 in the sleeve 64, resulting in the width (as indicated by the "W" direction in FIG. 7) of the sleeve 64 and thus convertible plunger 12' being reduced. The reduction in the width of the sleeve 64/convertible plunger 12' results in a reduction in the compressive force that had been used to form the seal between the convertible plunger 12' and the sidewall 58 of the barrel 56. In other words, slight axial stretching of the sleeve 64 (optionally achieved by displacing the insert 62 from a deactivated position to an activated position) in turn reduces the width of the sleeve 64 and convertible plunger 12', thus resulting in reduction in the compressive force that had been used to form the seal between the convertible plunger 12' and the sidewall 58 of the barrel 56.

Thus, with the width of the sleeve 64/convertible plunger 12' reduced, the force necessary to displace the convertible plunger 12' in the barrel 56 may also be reduced. Further, as previously discussed, as the interior shaft 16 may be locked in the second position by the locking tab 24, the sleeve 64 may maintain the elongated shape while the injection product is dispensed from the barrel 56.

Figure 39:
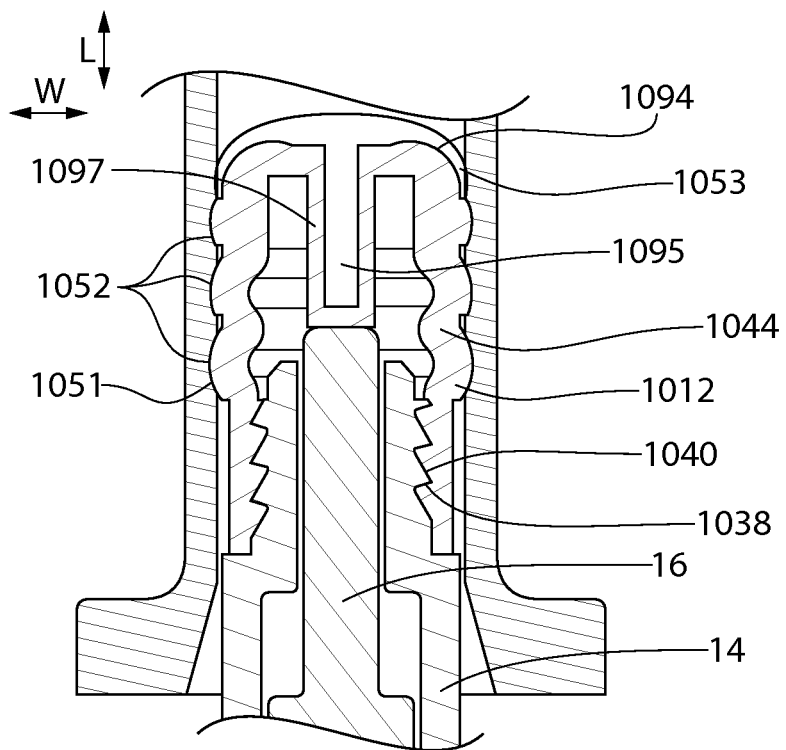
FIG. 39 illustrates a partial sectional view of a plunger in storage mode positioned within a barrel of a syringe.
Figure 39A:
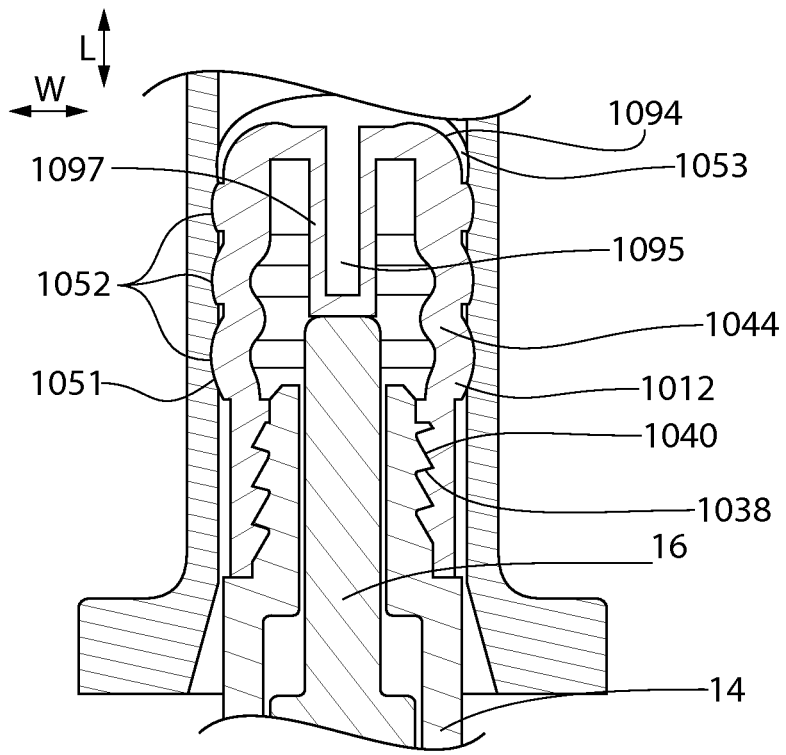
FIG. 39A illustrates the plunger of FIG. 39 in dispensing mode positioned within a barrel of a syringe.

An alternative embodiment of a convertible plunger 1012, in this case a stretchable plunger, is illustrated in FIGS. 39 and 39A. The stretchable plunger 1012 may be connected to an exterior shaft of a plunger rod 14, for example, by the threaded engagement of an internal thread 1040 on a connector body and the external thread 1038 of the exterior shaft.

The plunger 1012 includes a sleeve 1044 which may be constructed from any of the same materials of other sleeves (e.g., 44) disclosed in this specification. The outer portion of the sleeve 1044 comprises a sidewall and nose cone as with other sleeves disclosed in this specification. The sidewall of the sleeve 1044 includes a storage sealing section 1051 comprising three ribs 1052 (although more or fewer ribs may be used). As with the plunger 12 of FIGS. 1-4, the storage sealing section 1051 is configured (when in storage mode) to provide CCI and optionally a barrier to one or more gases. When the stretchable plunger 1012 is converted from storage mode to dispensing mode, the seal initially provided by the storage sealing section 1051 is either reduced or removed entirely.

Optionally, the outer portion of the sleeve 1044 may include a liquid sealing section 1053 preferably on the sidewall of the sleeve 1044 optionally adjacent to, distal to or otherwise near to the nose cone. The purpose of the liquid sealing section 1053 is to provide a liquid tight seal both when the plunger 1012 is in a storage mode and when the plunger is transitioned into dispensing mode. Optionally, the liquid sealing section 1053 may also provide CCI. The plunger 1012 further comprises a cap 1094 covering the nose cone and some or all of the liquid sealing section 1053. The cap 1094 is preferably made from an injection moldable thermoplastic material e.g., a cyclic olefin polymer (COP), cyclic olefin copolymer (COC) or polycarbonate. Optionally, the cap 1094 is an injection moldable part that is assembled onto the sleeve 1044. The cap 1094 may include an elongated stem 1095 extending into the sleeve 1044. Optionally, the sleeve 1044 includes a stem cover 1097 which receives and retains (e.g., through interference fit, adhesive, and/or other means) the stem 1095, thereby securely retaining the cap 1094 on the sleeve 1044.

A user's application of downward pressure onto the interior shaft 16 of the plunger rod 14 in turn transfers that pressure onto the stem cover 1097, the stem 1095 and the cap 1094. Since the cap 1094 is secured to the sleeve 1044, the initial movement of the interior shaft 16 does not at first displace the plunger 1012 down the barrel; rather such initial movement causes the cap 1094 to pull on and thus slightly stretch the sleeve 1044 in direction L. In so doing, the width W of the plunger 1012 is reduced slightly, thus reducing the plunger 1012 from an expanded state to a constricted state, or from storage mode to dispensing mode.

Optionally, the cap is coated with a barrier coating or layer to provide a gas barrier between contents of a syringe and the ambient environment. Optionally, at least one organo-siloxane coating or layer may be applied on top of the barrier coating or layer to protect the barrier layer from being degraded by syringe contents having a pH broadly within the range of 5 to 9. Optionally, a tri-layer coating set may be applied to the cap. These coatings, layers and coating sets are preferably applied via chemical vapor deposition, more preferably plasma enhanced chemical vapor deposition, and are described in detail elsewhere in this specification.

Figure 13:
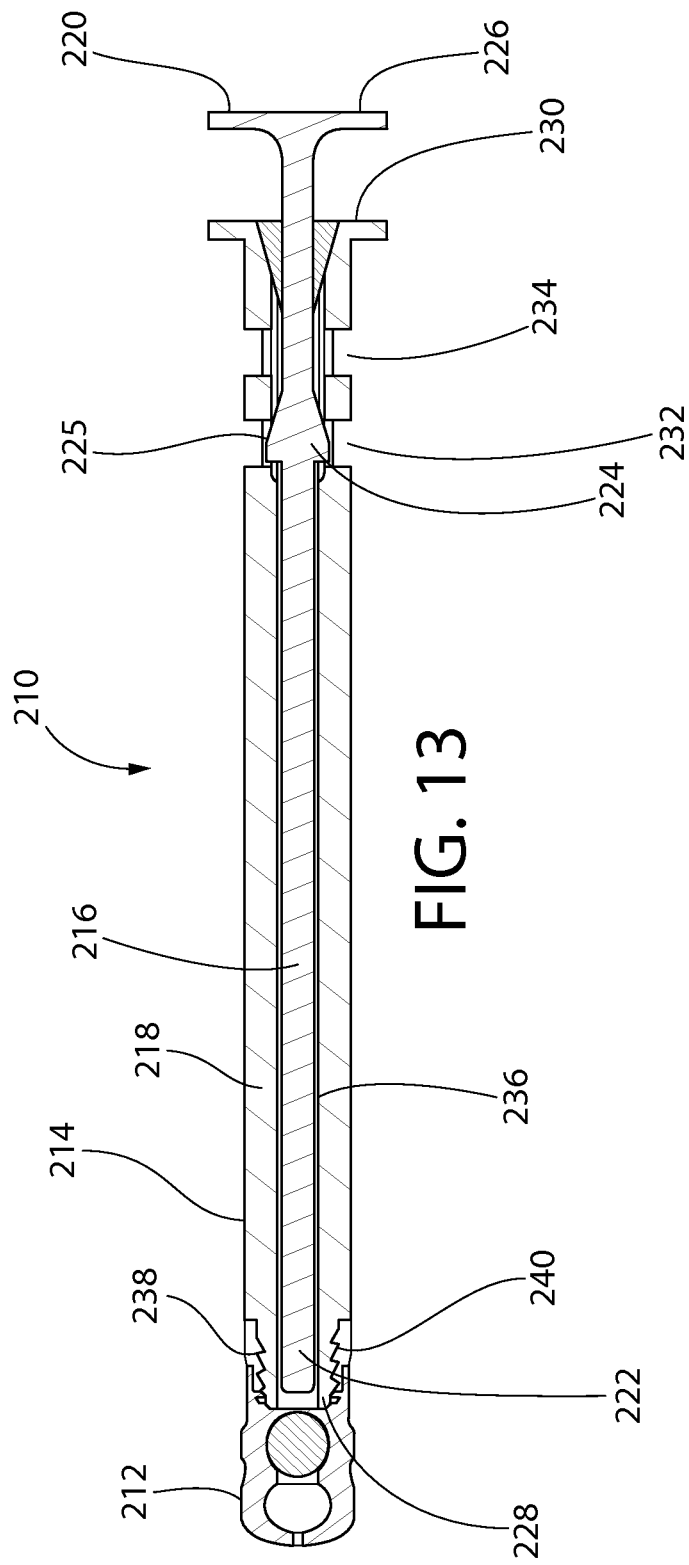
FIG. 13 illustrates an axial sectional view of a plunger assembly according to an illustrated embodiment.

Alternatively, two-position plunger assemblies may be desired for some applications wherein the interior shaft is displaced in a direction away from the plunger, rather than towards the plunger, from a first position to a second position relative to the exterior shaft. Such a configuration may be desired where it is preferable not to apply downward pressure on the plunger until it is time to advance the plunger into the barrel to dispense the syringe's contents. For example, FIG. 13 shows a two-position plunger assembly 210 that functions in essentially the same way as the assembly 10 shown in FIG. 2, except that the assembly 210 permits a user to move from a first position to a second position by displacing the interior shaft 216 away from the plunger 212, rather than towards the plunger 212. The convertible plunger 12 of the assembly 210 of FIG. 13, as shown, includes a first cavity and second cavity with a spherical insert disposed in the first cavity (e.g., as the convertible plunger 12 of FIG. 3). It should be understood that the plunger embodiment shown is for illustrative purposes only, and that various plunger configurations, including configurations discussed below, may optionally be used as part of the plunger assembly 210 of FIG. 13.

The plunger assembly 210 includes a plunger 212 and a plunger rod 214. The plunger rod 214 may include an interior shaft 216 and an exterior shaft 218. The interior shaft 216 includes a distal end 220, a proximal end 222, and a locking tab 224. According to certain embodiments, the distal end 220 of the interior shaft 216 may be configured to form an actuator 226 that, during use of the plunger assembly 210, is to be pressed upon by a user, such as, for example, by the thumb of the user. The exterior shaft 218 may include a first end 228, a second end 230, a first recess 232, a second recess 234, and an inner portion 236. According to certain embodiments, the first end 228 may be configured for a threaded engagement with the plunger 212. For example, as shown, the first end 228 may include an external thread 238 that is configured to mate with an internal thread 240 of the plunger 212.

FIG. 13 illustrates the interior shaft 216 in a first position relative to the exterior shaft 218, with the locking tab 224 protruding into at least a portion of the first recess 232 of the exterior shaft 218. The orientation of the tapered surface 225 of the locking tab 232 allows, when sufficient force is exerted upon the actuator 226, for the locking tab 232 to be at least temporarily compressed or deformed in size so that the locking tab 224 may at least temporarily enter into the inner portion 226 as the locking tab 225 is moved from the first recess 232 to the second recess 234. However, in the absence of sufficient force, the locking tab 232 may remain in the first recess 232, thereby maintaining the interior shaft 216 in the first position.

The orientation and size of the tapered surface 225 of the locking tab 224 may provide the locking tab 224 with sufficient width to prevent the locking tab 224 from being pushed into the inner portion 236 in the general direction of the first end 228 of the exterior shaft 218. Accordingly, when the locking tab 224 is in the second recess 234, and thus the interior shaft 216 is in the second position, the orientation and size of the tapered surface 225 of the locking tab 224 may provide the locking tab 224 with sufficient width to resist the locking tab 224 from being pushed back into the first recess 232. As such, pressing upon the actuator 226 would cause the entire plunger assembly 210 to move together as a single unit, e.g., within a pre-filled syringe barrel to dispense contents held therein.

In one aspect, the invention is directed broadly to convertible plungers and assemblies incorporating the same. Convertible plungers according to the present invention are adapted to provide sufficient compressive force against the sidewall of a pre-filled syringe or cartridge barrel to effectively seal and preserve the shelf-life of the contents of the barrel during storage. When a convertible plunger provides container closure integrity (CCI) adequate to effectively seal and preserve the shelf-life of the contents of the barrel during storage, the plunger (or at least a portion of its exterior surface) may alternatively be characterized as being in an expanded state or storage mode. The expanded state or storage mode may be a product of, for example, an expanded outer diameter or profile of at least a portion of the syringe barrel-contacting surface of the plunger and/or the normal force that the plunger exerts on the inner wall of the syringe barrel in which it is disposed. The convertible plunger (or at least a portion of its exterior surface) is reducible to what may be alternatively be characterized as a constricted state or a dispensing mode, wherein the compressive force against the sidewall of the barrel is reduced, allowing a user to more easily advance the plunger in the barrel and thus dispense the contents of the syringe or cartridge. The constricted state or dispensing mode may be a product of, for example, a reduced outer diameter (relative to that of the expanded state) of at least a portion of the syringe barrel-contacting surface of the plunger and/or reduced normal force against the inner wall of the syringe barrel exerted by the plunger. Other examples of what constitutes an expanded state versus constricted state are discussed below.

Accordingly, in one aspect, the invention is a convertible plunger comprising an internal portion and a generally cylindrical exterior surface. As used herein, a "generally cylindrical" exterior plunger surface may include minor interruptions or variations in geometry (e.g., due to ribs, valleys, etc.) to the otherwise cylindrical shape of the plunger. For example, a generally cylindrical exterior surface of the plunger may include one or more annular ribs. At least a portion of the exterior surface is maintained in an initial expanded state by a property of the internal portion. The expanded state is reducible to a constricted state by an operation that is applied to the internal portion of the plunger to alter the property. The plunger may be reduced from the expanded state to the constricted state utilizing a variety of methods, which may include two-position configurations, e.g., as described above, or not. As used herein, "expanded state" and "constricted state" may refer to comparative dimensional measurements (e.g., expanded state being wider than constricted state) and/or comparative resistance to inward compression of the plunger (the "expanded state" being more resistant to inward compression and the "constricted state" being less resistant to inward compression) and/or comparative outward radial pressure exerted by at least a portion of the plunger's exterior surface (the plunger's exterior surface in the "expanded state" exerting more outward radial pressure and in the "constricted state" exerting less outward radial pressure).

For example, the property that maintains at least a portion of the exterior surface of the plunger in the expanded state may include, e.g., gas pressure, mechanically produced outward radial pressure or outward radial pressure produced by a liquid or gelatinous compression material disposed within one or more cavities within the plunger. Where the property is gas pressure, the property may be altered by releasing at least some of the pressure from the cavity or cavities. Where the property is mechanically produced outward radial pressure, such as that produced by a solid compression material, the property may be altered by, e.g., collapsing, crushing, deforming, breaking, or otherwise altering the structure of the solid compression material in whole or in part, or displacing the solid compression material, so as to reduce the outward radial pressure. Where the property is outward radial pressure produced by a liquid or gelatinous material, the property may be altered by removing at least some of the material from the cavity.

Optionally, the convertible plunger may be a component of a plunger assembly, for example, any of the plunger assemblies described above. The assembly comprises a plunger rod having an exterior shaft and an interior shaft. The exterior shaft has an inner portion configured for the slideable insertion of at least a portion of the interior shaft and the interior shaft is configured to be displaced from a first position to a second position relative to the exterior shaft. The assembly further comprises the convertible plunger operably connected to the plunger rod, the convertible plunger configured to receive the insertion of at least a portion of the interior shaft. Depending on the application, the interior shaft may be displaceable from a first position to a second position in a direction towards the plunger (e.g., using the assemblies shown in FIG. 2 or 5), or in a direction away from the plunger (e.g., using the assembly shown in FIG. 13).

Figure 14:
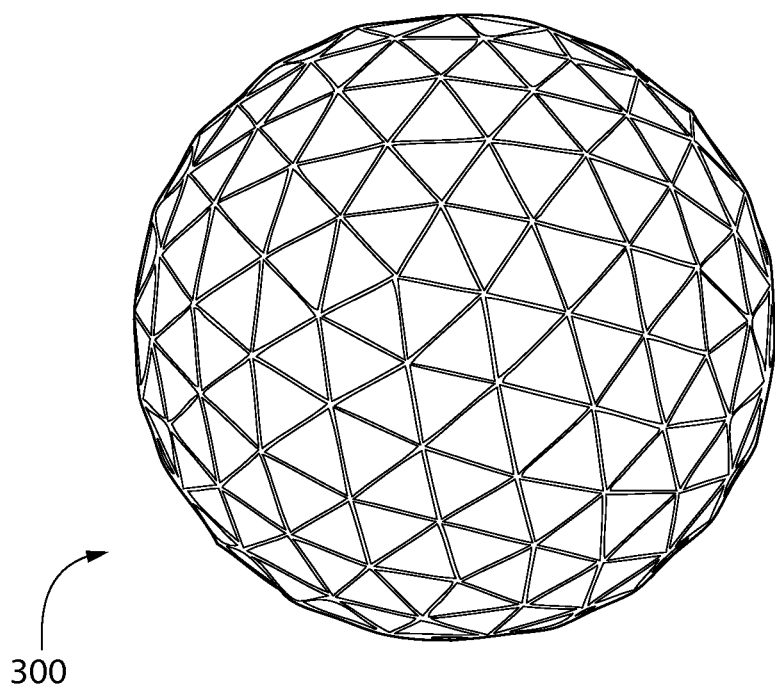
FIG. 14 illustrates a perspective view of a substantially spherical mesh insert.
Figure 15:
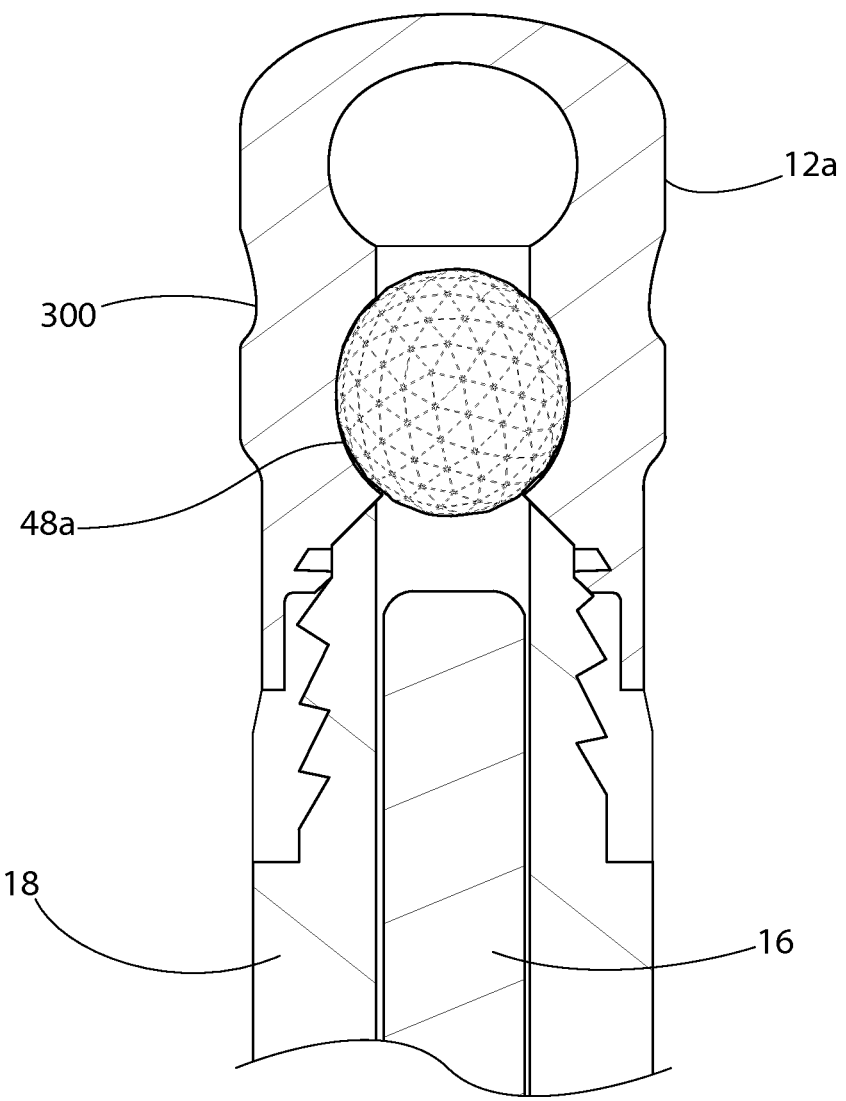
FIG. 15 illustrates an isolated sectional view of an alternative plunger assembly configured similarly to the assembly shown in FIG. 2, with the connector body transparent to reveal internal structure, the plunger having disposed within it the substantially spherical mesh insert shown in FIG. 14.

Referring to FIG. 14, there is shown a substantially spherical mesh insert 300. As shown in FIG. 15, the spherical mesh insert 300 may be disposed within a cavity 48a of a convertible plunger 12a. The mesh insert is configured to provide mechanically produced outward radial pressure to maintain the exterior surface of the plunger 12a in an initial expanded state. When the plunger 12a is a component in a plunger assembly such as the assembly 10 shown in FIG. 2, displacement of the interior shaft 16 relative to the exterior shaft 18 towards the plunger 12a causes the interior shaft 16 to contact and press into the spherical mesh insert 300. When sufficient pressure is applied against the spherical mesh insert 300, its structural integrity is compromised, causing it to collapse or deform. This reduces outward radial pressure in the plunger 12a, thereby reducing at least a portion of the exterior surface of the plunger 12a to a constricted state. Once the exterior surface of the plunger 12a is in a constricted state, the plunger rod 214, as e.g. a component of a prefilled syringe, is ready to be actuated to dispense the contents of the syringe. The spherical mesh insert 300 may be made, e.g., from metal or plastic. A skilled artisan would readily recognize that the invention may be implemented using solid materials other than mesh inserts, for example other collapsible or breakable materials and configurations.

Figure 16:
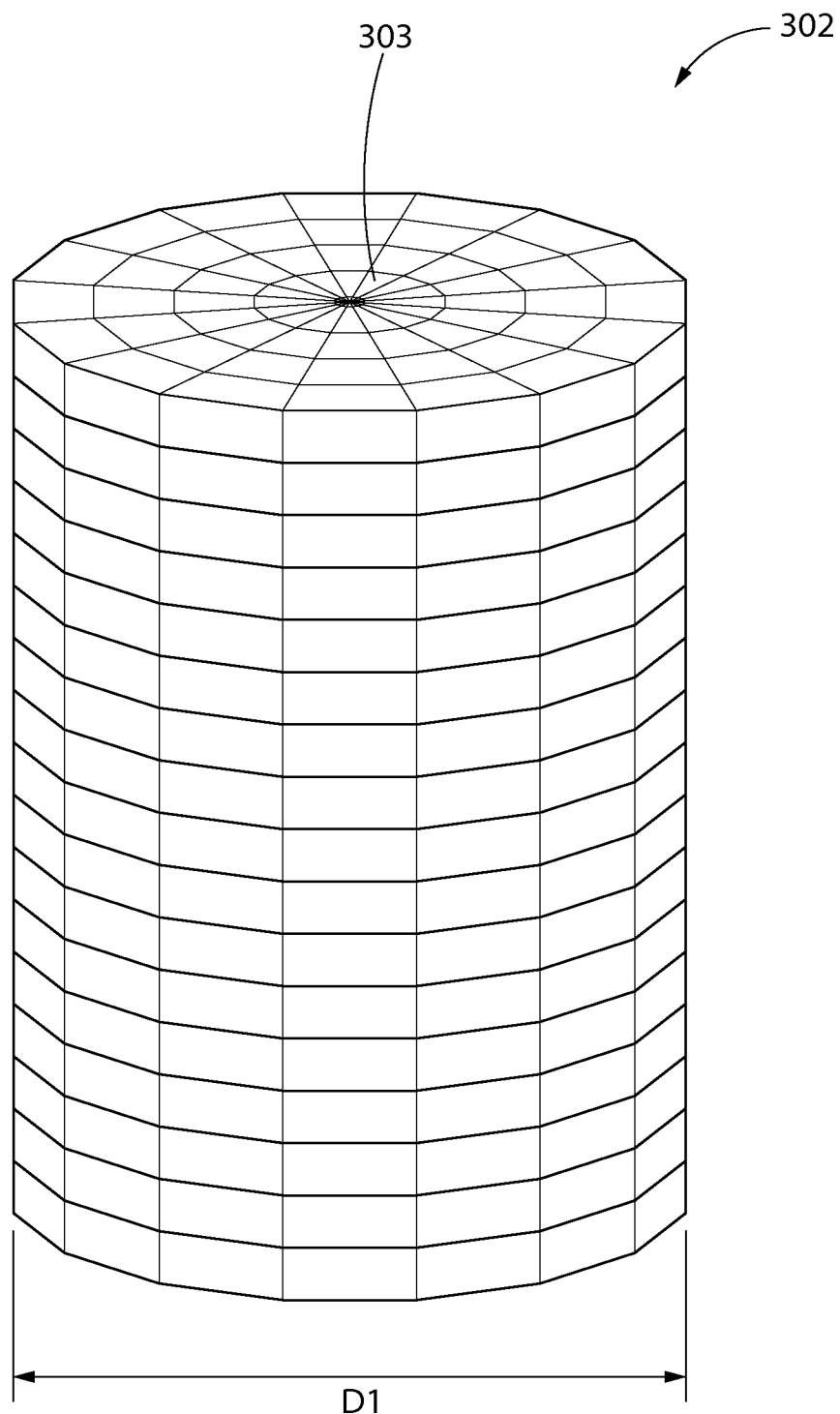
FIG. 16 illustrates a perspective view of a substantially cylindrical insert.
Figure 16A:
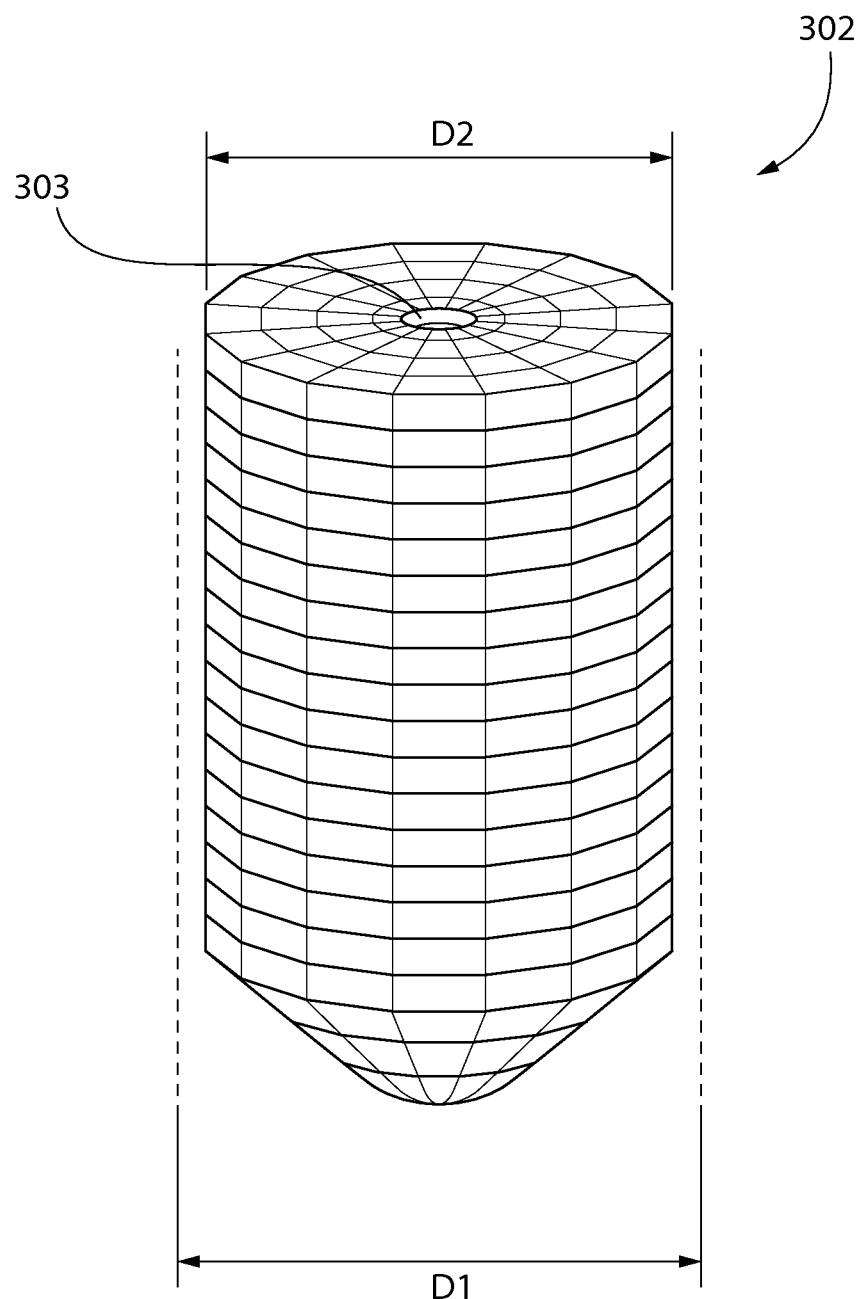
FIG. 16A illustrates a perspective view of the substantially cylindrical insert of FIG. 16 after it has been inwardly collapsed.

For example, referring to FIG. 16, there is shown a substantially cylindrical insert 302. The cylindrical insert 302 may be in the form of a collapsible mesh, for example. Alternatively, the cylindrical insert 302 may be a solid or substantially solid compression material, e.g., a polymer, which is mechanically less resistant to axially applied pressure than to inward radial pressure. While a substantially cylindrical geometry is preferred for this type of insert, it is contemplated that other geometries which are inwardly collapsible or deformable, upon application of axial pressure, may be utilized as well. The cylindrical insert 302 includes a central portion 303. When sufficient pressure is applied to the central portion 303, the insert 302 collapses inward (towards the central axis). Prior to the inward collapse of the insert 302, the insert 302 has a first diameter D1. After the inward collapse of the insert 302, the insert 302 is reduced to a constricted second diameter D2, as shown in FIG. 16A.

Figure 17:
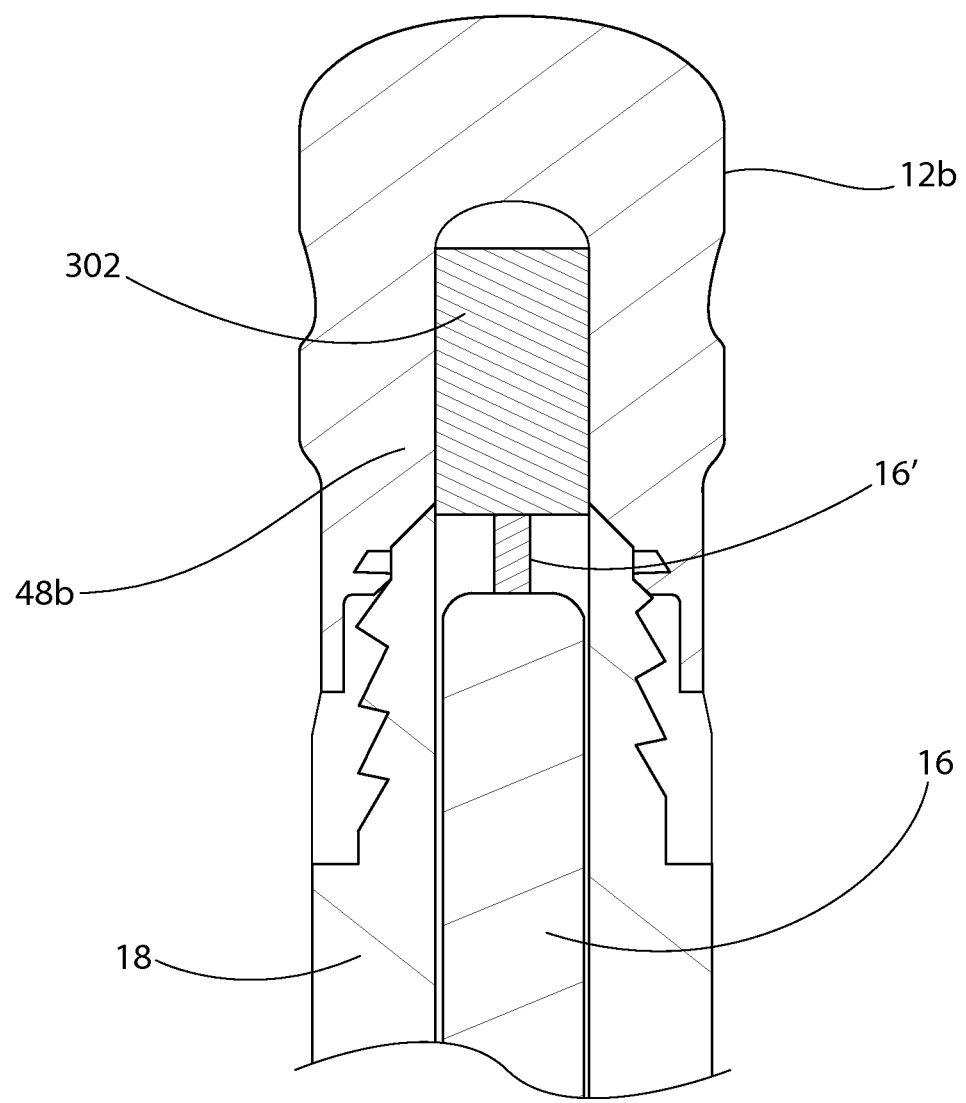
FIG. 17 illustrates an isolated sectional view of an alternative plunger assembly configured similarly to the assembly shown in FIG. 2, with the connector body transparent to reveal internal structure, the plunger having disposed within it the substantially cylindrical insert shown in FIG. 16.

Referring to FIG. 17, the cylindrical insert 302 may be disposed within a cavity 48b of a convertible plunger 12b. The insert 302 is configured to provide mechanically produced outward radial pressure to maintain the exterior surface of the plunger 12b in an initial expanded state. When the plunger 12b is a component in a plunger assembly such as the assembly 10 shown in FIG. 2, displacement of the interior shaft 16 relative to the exterior shaft 18 towards the plunger 12b causes a narrow tip 16' on the interior shaft 16 to contact and press into the central portion 303 of the insert 302. When sufficient pressure is applied against the central portion 303, the structural integrity of the insert 302 is compromised, causing it to collapse or deform inward. This reduces outward radial pressure in the plunger 12b, causing at least a portion of the exterior surface of the plunger 12b to be reduced to a constricted state. Once the exterior surface of the plunger 12b is in a constricted state, the plunger rod 14, as e.g. a component of a prefilled syringe, is ready to be actuated to dispense the contents of the syringe.

Figure 18:
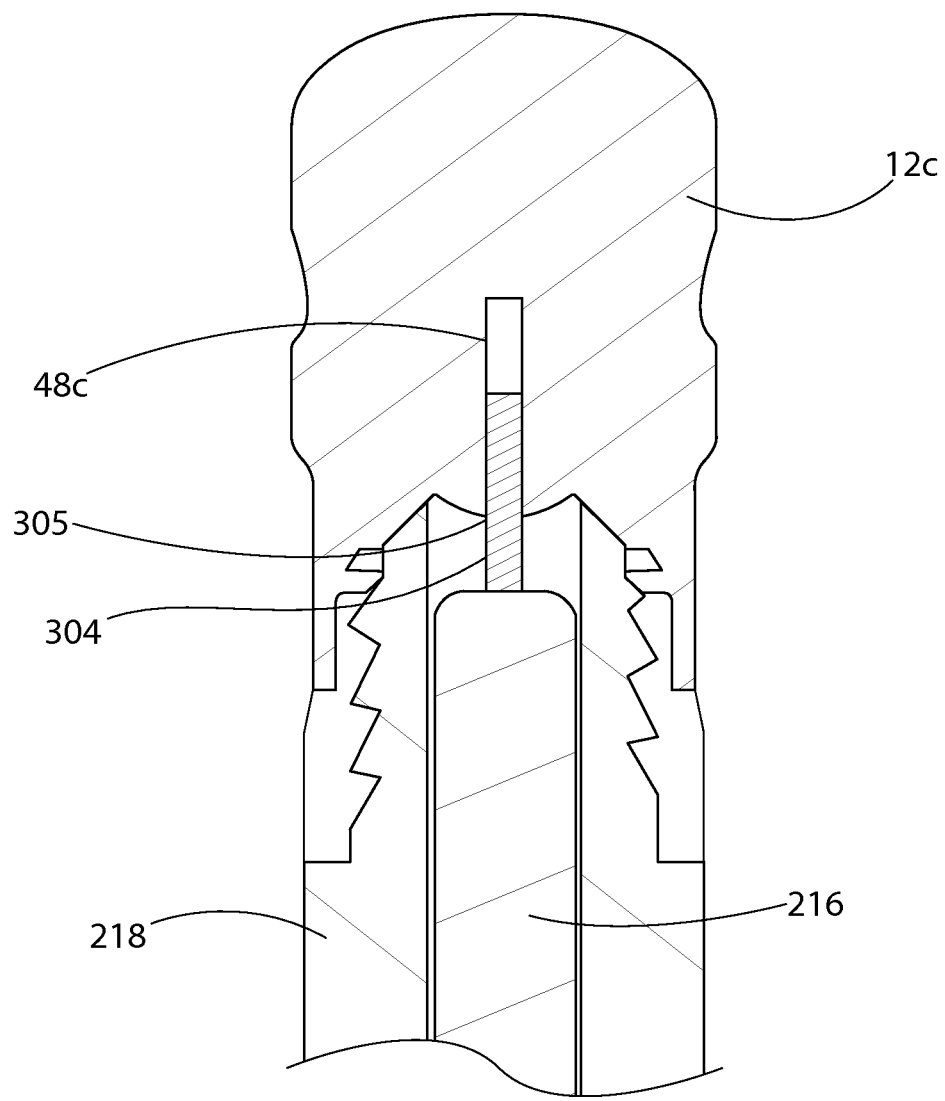
FIG. 18 illustrates an isolated sectional view of an alternative plunger assembly configured similarly to the assembly shown in FIG. 13.

Referring to FIG. 18, there is shown an alternative embodiment of a plunger assembly utilizing the basic configuration of the assembly 210 shown in FIG. 13. This embodiment may include a plunger 12c secured to the exterior shaft 218 and an interior shaft 216 axially displaceable relative to the exterior shaft 218. The plunger 12c has a thin, substantially cylindrical cavity 48c along the central axis of the plunger 12c, with an opening 305 at the top of the plunger 12c. Extending axially from the proximal end 222 of the interior shaft 216 is a thin, substantially cylindrical protrusion 304 having complementary or mating geometry with the cavity 48c in the plunger 12c. At least a portion of the exterior surface of the plunger 12c is maintained in an initial expanded state when the cavity 48c is mated with or occupied by the protrusion 304. In other words, the protrusion 304 provides mechanically produced outward radial pressure to maintain the exterior surface of the plunger 12c in an expanded state.

The protrusion 304 is removable from the cavity 48c by displacing the interior shaft 216 in a direction away from the plunger 12c to retract the protrusion 304 out of the opening 305 until the protrusion 304 no longer occupies the cavity 48c, and thus no longer provides the mechanically produced outward radial pressure within the plunger 12c. In this position, the empty cavity 48c does not resist inward compression as well as it did when it was occupied by the protrusion 304 and thus the exterior surface of the plunger 12c is reduced to a constricted state. Optionally, the protrusion 304 and/or the cavity 48c are lubricated, e.g., with silicone oil or a lubricious film coating, such as those described below, to facilitate easy removal of the protrusion 304 from the cavity 48c. Once the exterior surface of the plunger 12c is in a constricted state, the plunger rod 214, as e.g. a component of a prefilled syringe, is ready to be actuated to dispense the contents of the syringe.

Figure 19:
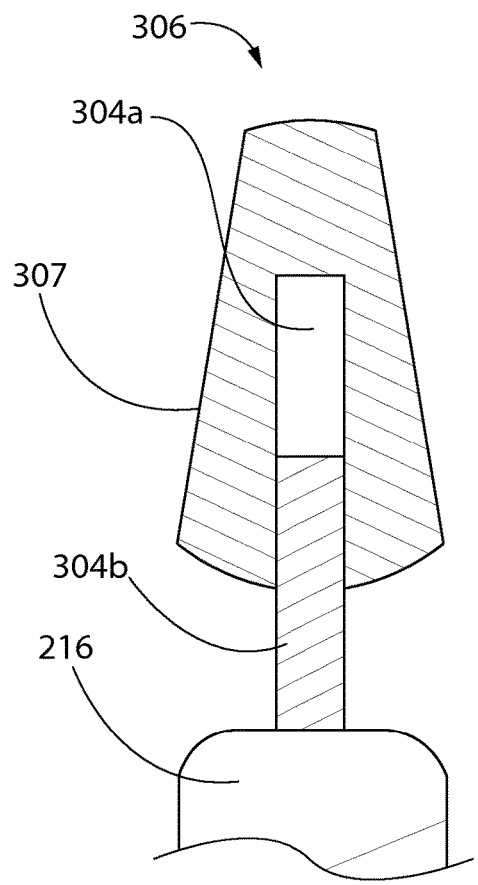
FIG. 19 illustrates an isolated sectional view of a tapered insert having partially inserted therein a protrusion axially extending from an interior shaft of a plunger rod.

Referring to FIG. 19, there is shown an anchoring device, or tapered insert 306 configured much like a plaster anchor. Plaster anchors are hollow, typically tapered tubular members that are adapted to expand upon receipt of a screw or another narrow protrusion. A plaster anchor may revert, at least in part, to its initial unexpanded state upon removal of the screw or other narrow protrusion. Likewise, the insert 306, which may comprise one or more axially tapered wings 307 about its periphery and a narrow axial cavity 304a, is in an expanded state when a protrusion 304b is inserted in the cavity 304a. The insert 306 is reduced to a less expanded state upon removal of the protrusion 304b from the cavity 304a. Although the embodiment of the insert 306 as shown is tapered, non-tapered configurations, e.g., with substantially parallel wings or sides, are within the scope of the invention.

Figure 20:
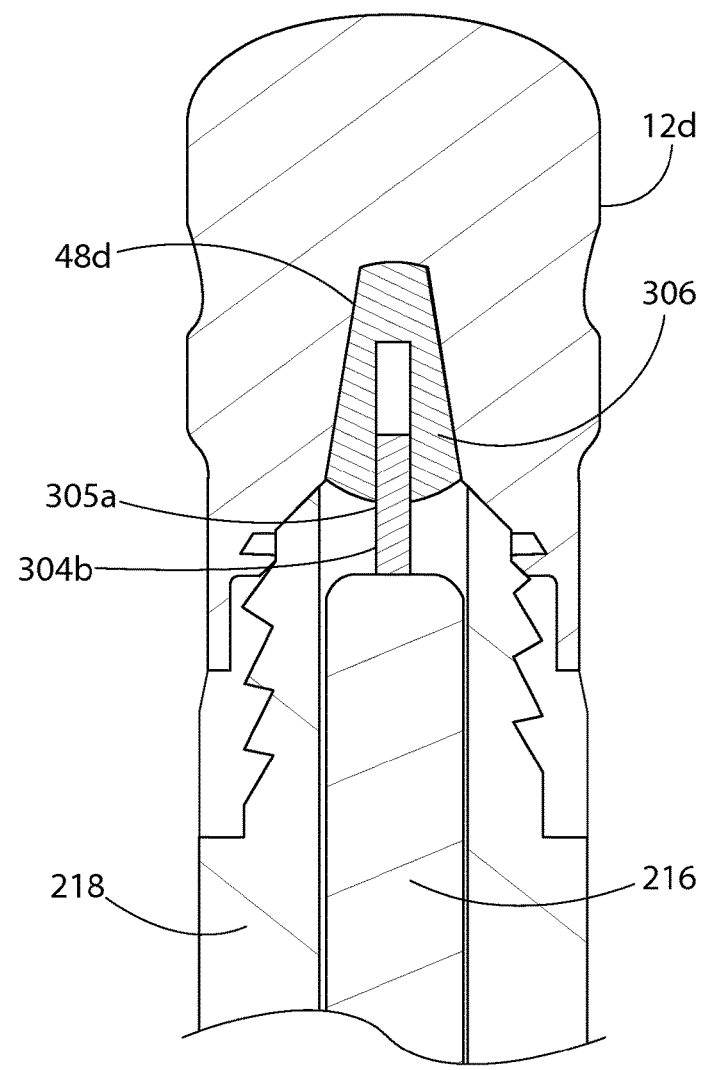
FIG. 20 illustrates an isolated sectional view of an alternative plunger assembly configured similarly to the assembly shown in FIG. 13, the plunger having disposed within it the tapered insert shown in FIG. 19.

Referring to FIG. 20, there is shown an alternative embodiment of a plunger assembly utilizing the basic configuration of the assembly 210 shown in FIG. 13. This embodiment may include a plunger 12d secured to the exterior shaft 218 and an interior shaft 216 axially displaceable relative to the exterior shaft 218. The plunger 12d optionally has a substantially tapered cavity 48d along the central axis of the plunger 12d, with an opening 305a at the top of the plunger 12d. The insert 306 is disposed within the cavity 48d, and may be integral with the plunger 12d (e.g., molded within the plunger) or a separate component inserted within the plunger cavity 48d. Extending axially from the proximal end 222 of the interior shaft 216 is the thin, substantially cylindrical protrusion 304b having complementary or mating geometry with the cavity 304a in the insert 306. At least a portion of the exterior surface of the plunger 12d is maintained in an initial expanded state when the cavity 304a is mated with or occupied by the protrusion 304b. In other words, the protrusion 304b expands the wings 307 of the insert so as to provide mechanically produced outward radial pressure to maintain the exterior surface of the plunger 12d in an expanded state. The protrusion 304b is removable from the cavity 304a by displacing the interior shaft 216 in a direction away from the plunger 12d to retract the protrusion 304b out of the opening 305a until the protrusion 304b no longer occupies the cavity 304a. Once the protrusion 304b has been removed from the cavity 304a, the wings 307 slightly retract inward towards the insert's central axis, thereby reducing outward radial pressure within the plunger 12d, thus permitting the exterior surface of the plunger 12d to be reduced to a constricted state. Once the exterior surface of the plunger 12d is in a constricted state, the plunger rod 214, as e.g. a component of a prefilled syringe, is ready to be actuated to dispense the contents of the syringe.

The protrusion 304b may optionally be removed from the cavity 304a by pulling the interior shaft 216 from a first position to a second position, substantially as described above with respect to the assembly 210 shown in FIG. 13. Alternatively, the internal shaft 216 may be rotatable in relation to the external shaft 218, or vice versa. With such a configuration, the protrusion 304b may be threaded and mated with complementary threads within the cavity 304a. To remove the insert 304b from the cavity 304a, a user may rotate the internal shaft 216 relative to the external shaft 218 (or vice versa), thereby displacing the internal shaft 216 from a first position (wherein the insert 304b occupies the cavity 304a) to a second position (wherein the insert 304b is removed from the cavity 304b).

Figure 21:
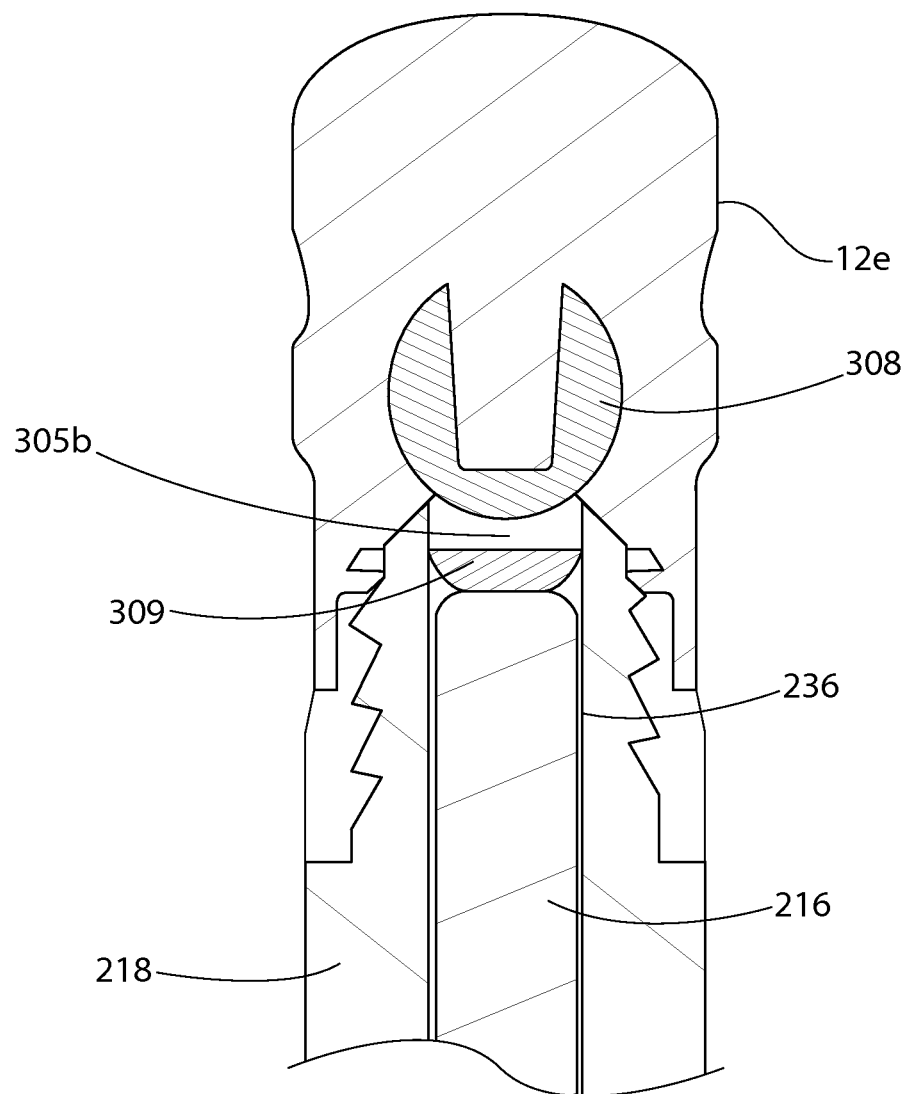
FIG. 21 illustrates an isolated sectional view of an alternative plunger assembly configured similarly to the assembly shown in FIG. 13.

Referring now to FIG. 21, there is shown an alternative embodiment of a plunger assembly utilizing the basic configuration of the assembly 210 shown in FIG. 13. This embodiment may include a plunger 12e secured to the exterior shaft 218 and an interior shaft 216 axially displaceable relative to the exterior shaft 218. Part of the internal portion of the plunger 12e comprises a porous material 308, such as a foam rubber. Alternatively, part of the internal portion of the plunger 12e comprises empty space. The plunger 12e further includes one or more openings 305b in the top thereof, providing a conduit to the porous material 308 (or empty space, as the case may be). The proximal end of the interior shaft 216 includes a stopper 309, optionally made from a rubber or a polymer. The stopper 309 provides an air-tight seal between the one or more openings 305b and the inner portion 236 of the exterior shaft 218. Accordingly, when the interior shaft 216 is displaced away from the plunger 12e, e.g., from a first position to a second position, the stopper effectively sucks air from the porous material 308 (or empty space) creating therein at least a partial vacuum. This in turn causes the porous material 308 (or empty space) to collapse, thus reducing at least part of the exterior surface of the plunger 12e from an expanded state to a constricted state. Once the exterior surface of the plunger 12e is in a constricted state, the plunger rod 214, as e.g. a component of a prefilled syringe, is ready to be actuated to dispense the contents of the syringe.

Figure 22:
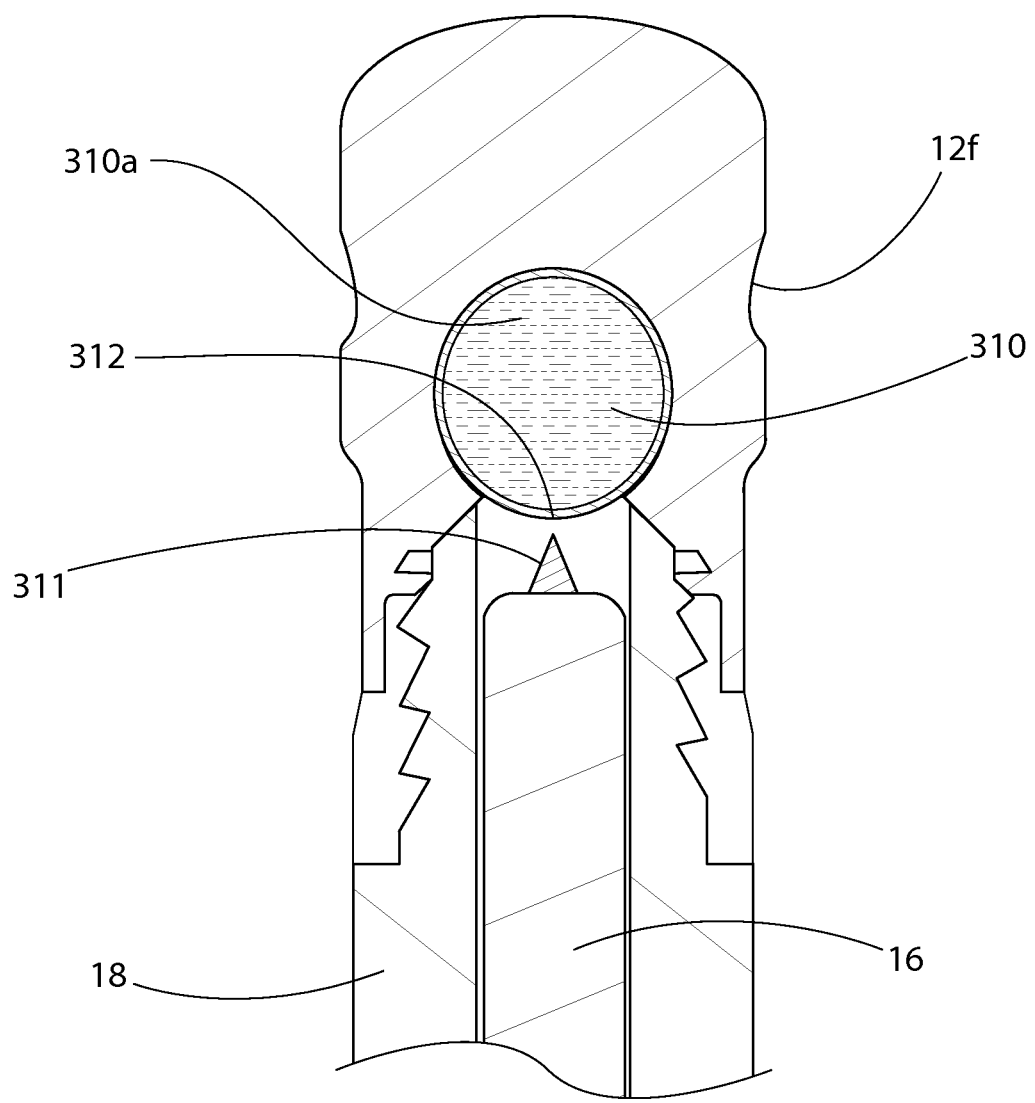
FIG. 22 illustrates an isolated sectional view of an alternative plunger assembly configured similarly to the assembly shown in FIG. 13.

Referring now to FIG. 22, there is shown a convertible plunger 12f having a sealed inner cavity 310 and/or a sealed insert comprising a gaseous, gelatinous or liquid compression material 310a. The sealed inner cavity 310 and/or sealed insert comprises an inner surface or membrane 312 which effectively seals the compression material 310a within the insert. The compression material 310a is configured to provide outward radial pressure to maintain at least a portion of the exterior surface of the plunger 12f in an initial expanded state. When the plunger 12f is a component in a plunger assembly such as the assembly 10 shown in FIG. 2, the proximal end of the interior shaft 16 includes a substantially sharp tip 311 extending axially therefrom. Displacement of the interior shaft 16 relative to the exterior shaft 18 towards the plunger 12f causes the tip 311 to contact and press into the top of the plunger 12f. When sufficient pressure is applied against the top of the plunger 12f, the tip 311 causes the membrane 312 to be punctured, thus enabling the egress of at least some of the compression material 310a from the cavity 310. This reduces outward radial pressure in the plunger 12f, thereby reducing at least a portion of the exterior surface of the plunger 12f to a constricted state. Once the exterior surface of the plunger 12f is in a constricted state, the plunger rod 14, as e.g. a component of a prefilled syringe, is ready to be actuated to dispense the contents of the syringe.

Figure 23:
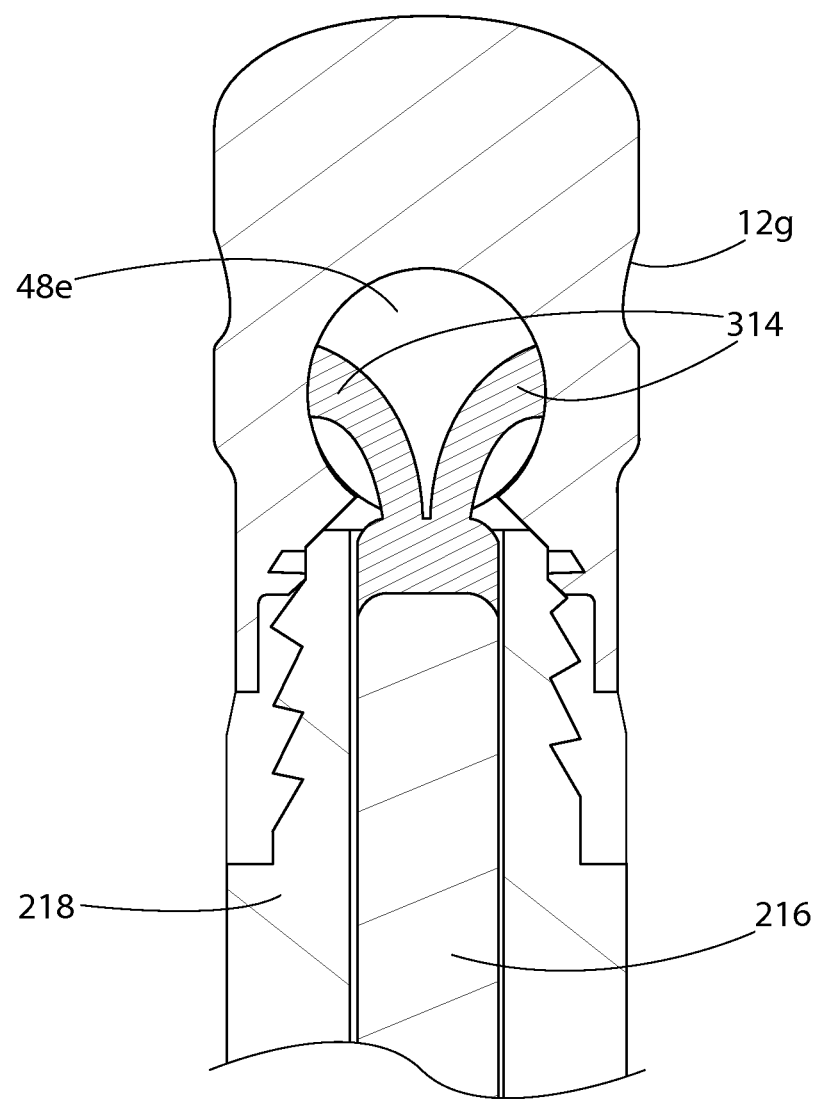
FIG. 23 illustrates an isolated sectional view of an alternative plunger assembly configured similarly to the assembly shown in FIG. 13, the convertible plunger's exterior surface being in an expanded state.
Figure 23A:
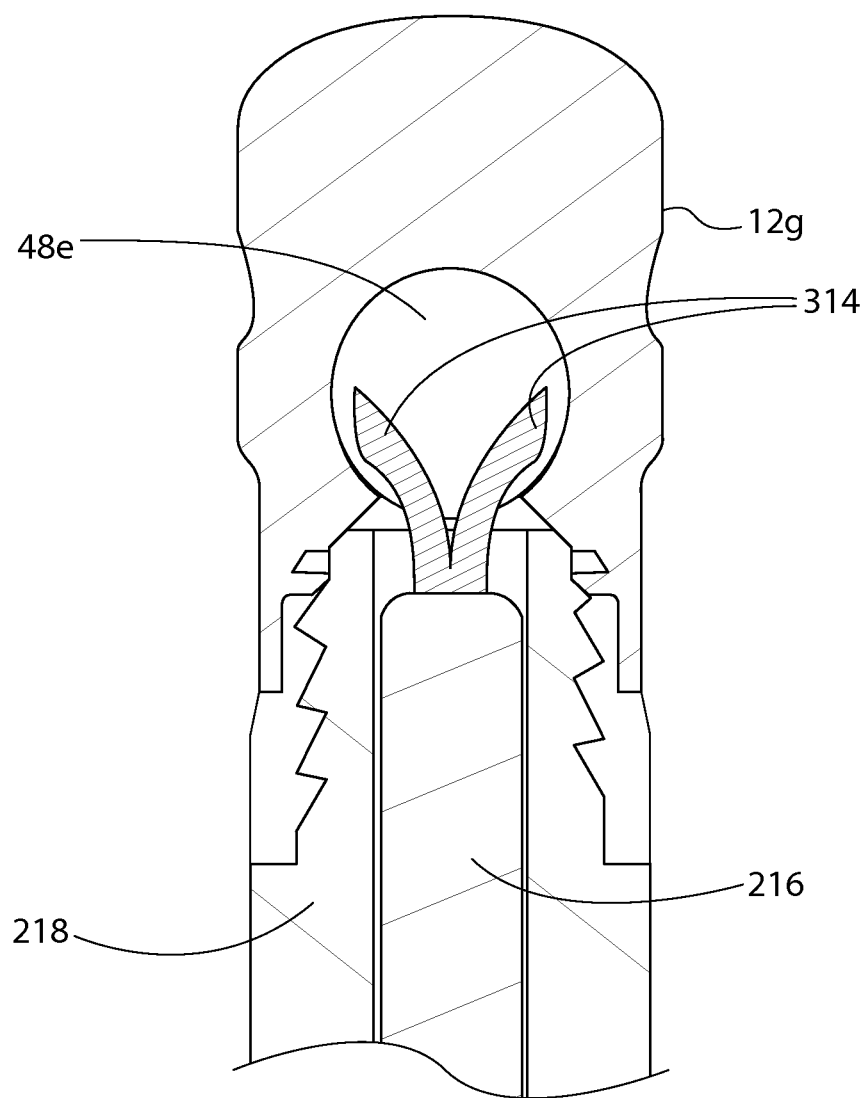
FIG. 23A is the same embodiment and view illustrated in FIG. 23, except that the convertible plunger's exterior surface is in a constricted state.

Referring to FIG. 23, there is shown an alternative embodiment of a plunger assembly utilizing, e.g., the basic configuration of the assembly 210 shown in FIG. 13. This embodiment may include a convertible plunger 12g secured to the exterior shaft 218 and an interior shaft 216 axially displaceable relative to the exterior shaft 218. The plunger 12g has a cavity 48e within the internal portion thereof. Extending from the end of the proximal end of the interior shaft 216 and into the cavity 48e are at least two opposing juts 314. Optionally three to eight (or even more) juts 314 may be used. When the interior shaft 216 is in a first position, the juts 314 press into the interior surface of the cavity 48e, thereby providing mechanically produced outward radial pressure to maintain the exterior surface of the plunger 12g in an expanded state. As shown in FIG. 23A, when the interior shaft 216 is displaced in a direction away from the plunger 12g and into a second position relative to the exterior shaft 218, the juts 314 retract inwardly towards the central axis of the interior shaft 216. In so doing, the juts 314 no longer contact the interior surface of the cavity 48e and thus no longer provide the mechanically produced outward radial pressure within the plunger 12c. In this position, the juts 314 do not support the cavity 408e in resisting inward compression and thus the exterior surface of the plunger 12g is reduced to a constricted state. Once the exterior surface of the plunger 12g is in a constricted state, the plunger rod 214, as e.g. a component of a prefilled syringe, is ready to be actuated to dispense the contents of the syringe.

Figure 24:
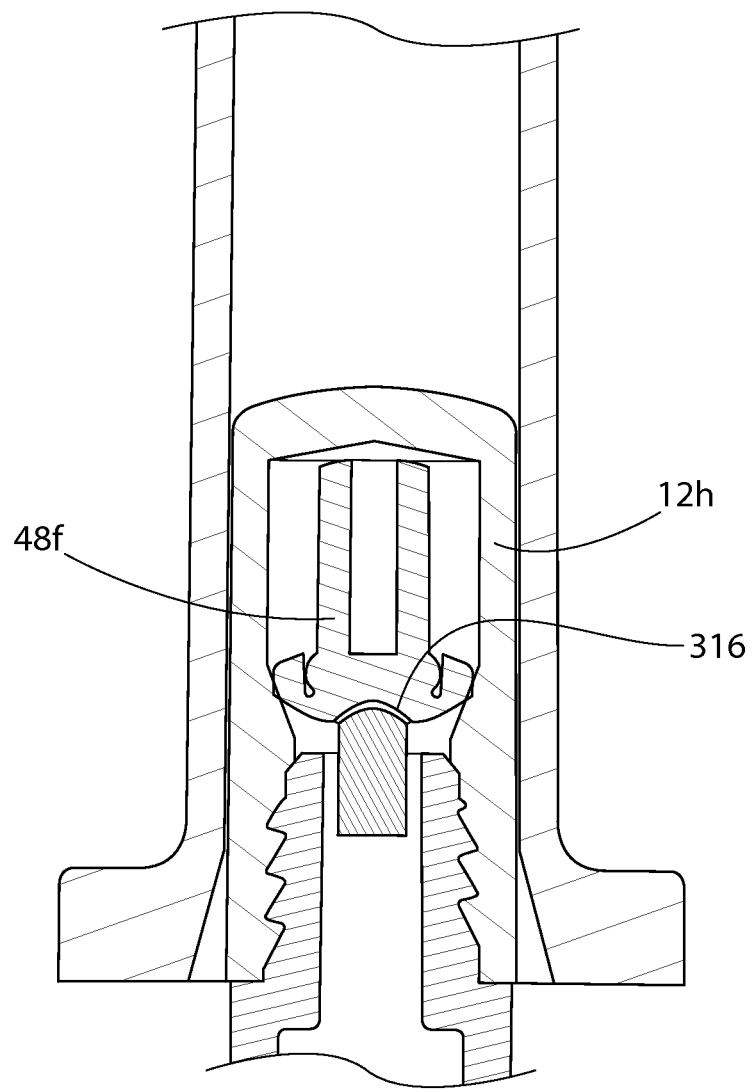
FIG. 24 illustrates an isolated sectional view of an alternative plunger disposed within a syringe.

Referring to FIG. 24, there is shown a convertible plunger 12h in an expanded or storage state, disposed within a syringe barrel. The plunger 12h includes an internal portion having a cavity 48f charged with gas, e.g., nitrogen, carbon dioxide, air or butane, for example. The gas pressure within the cavity 48f should be above atmospheric pressure, so as to maintain at least a portion of the external surface of the plunger in an initial expanded state. The cavity 48f may include a valve 316 which maintains the gas pressure within the cavity 48f, but is operable to be triggered to release the pressure. The valve may be triggered, for example, by actuating the interior shaft 16 of the plunger rod, e.g., substantially as discussed above with respect to the assembly shown in FIG. 2. When the valve is released, the gas pressure within the cavity 48f is reduced, e.g., to atmospheric pressure. In this way, the plunger 12h effectively deflates (however insubstantially) thus reducing the profile of the exterior surface from the expanded state to a constricted state. Once the exterior surface of the plunger 12h is in a constricted state, the plunger rod 14, as e.g. a component of a prefilled syringe, is ready to be actuated to dispense the contents of the syringe.

Figure 25:
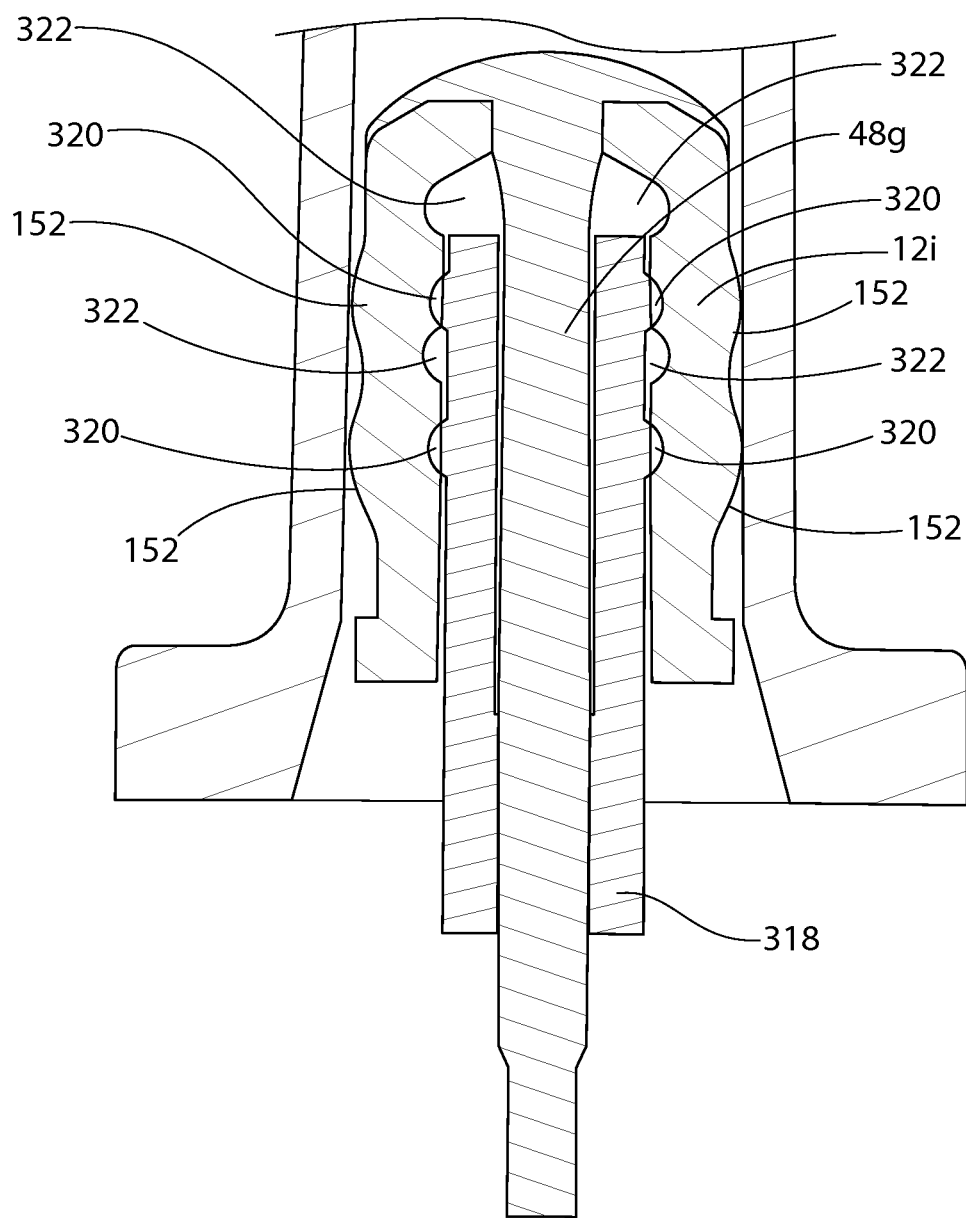
FIG. 25 illustrates an isolated sectional view of an alternative plunger disposed within a syringe.

Referring to FIG. 25, there is shown a convertible plunger 12i disposed within a syringe barrel. The plunger 12i includes an internal portion having an axial cavity 48g with annular grooves 322 axially spaced apart from one another. The plunger 12i is a component of an assembly having a sliding shaft 318 that is displaceable along its axis. The sliding shaft 318 includes annular rings 320 axially spaced apart from one another. The rings 320 are adapted to mate with the grooves 322. In a first position, shown in FIG. 25, the rings 320 do not occupy the grooves 322, but instead press against the interior surface of the cavity, providing outward radial pressure that maintains adjacent ribs 152 of the plunger 12i in an expanded state. When the sliding shaft 318 is displaced further into the plunger 12i, the rings 320 mate with respective grooves 322 in a second position. In this second position, the outward radial pressure behind the ribs 152 is reduced, thus reducing the exterior surface of the plunger 12g to a constricted state. Once the exterior surface of the plunger 12i is in a constricted state, the plunger rod 14, as e.g. a component of a prefilled syringe, is ready to be actuated to dispense the contents of the syringe.

Film Coatings and Molded Caps

In another aspect, the invention is directed to novel film coatings applied to plungers, e.g., any of the plungers described herein whether convertible or not. It should be understood that films and film coatings, as shown in drawing figures (FIGS. 8-12, 26 and 26A), are depicted as having exaggerated thicknesses, for purposes of clarity only. The films and film coatings in reality would optionally be much thinner (e.g., under 100 micrometers) than as depicted in the relevant figures.

Figure 8:
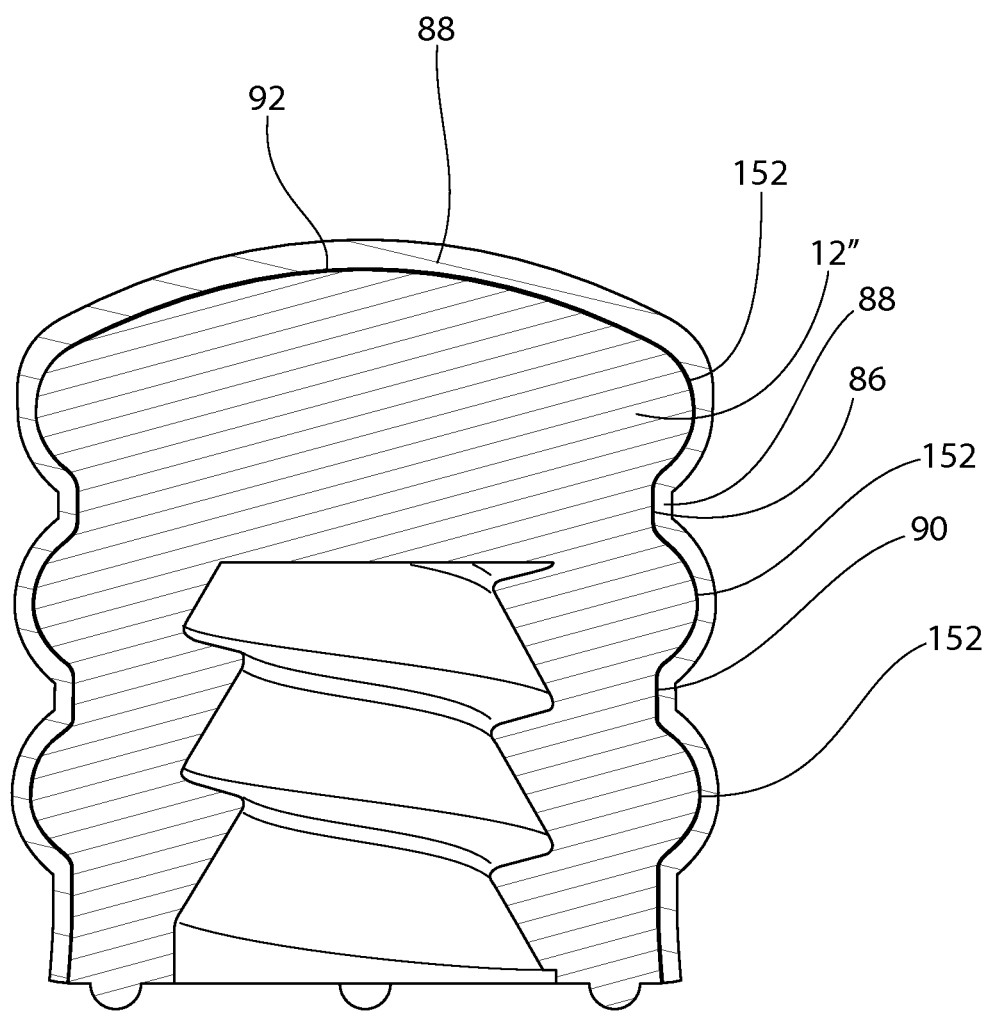
FIG. 8 illustrates an axial sectional view of a plunger having a film coating according to an illustrated embodiment.
Figure 9:
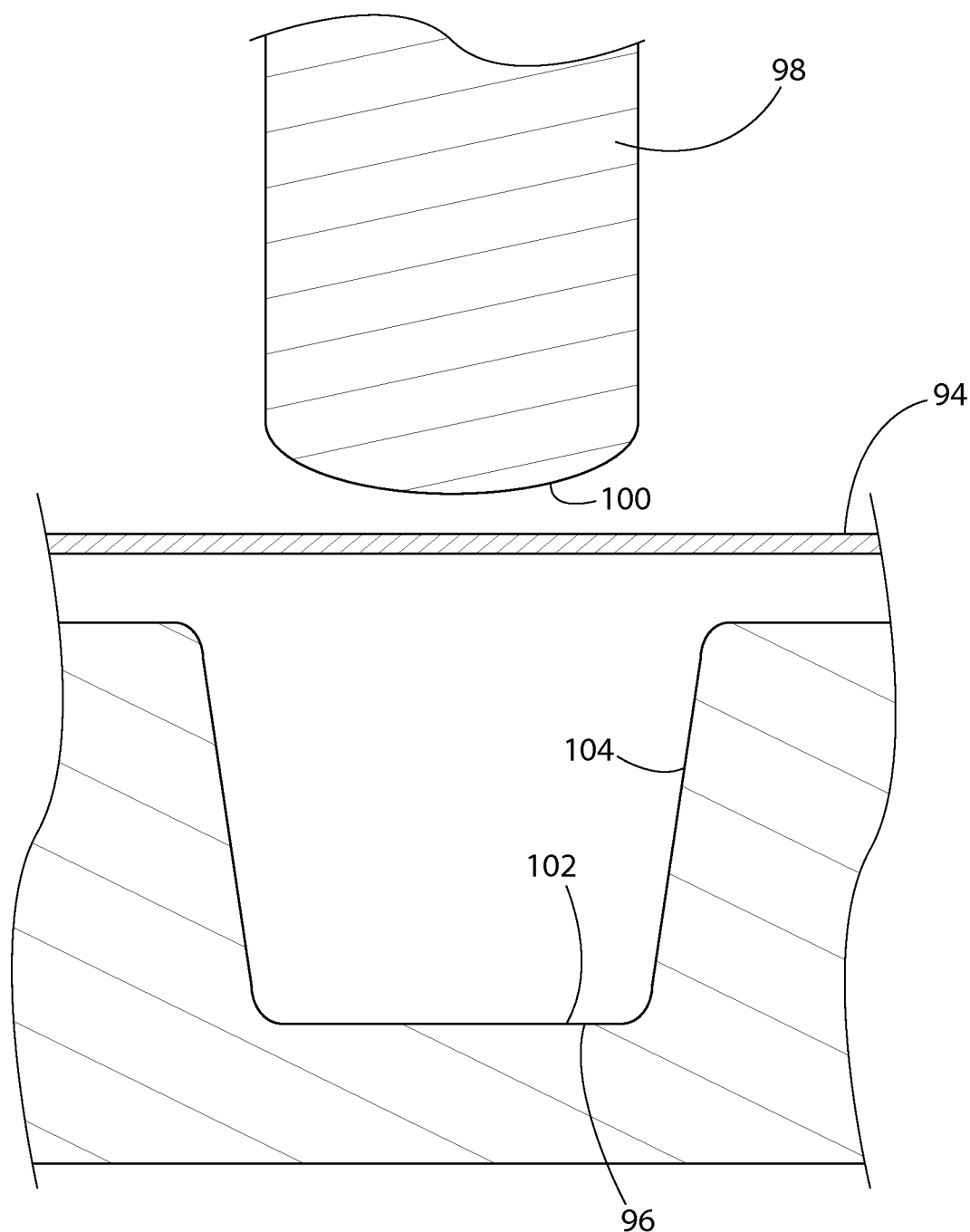
FIG. 9 illustrates a schematic axial sectional view of a forming die and forming plug used to transform a portion of a film into a coating preform for a film coating.
Figure 10:
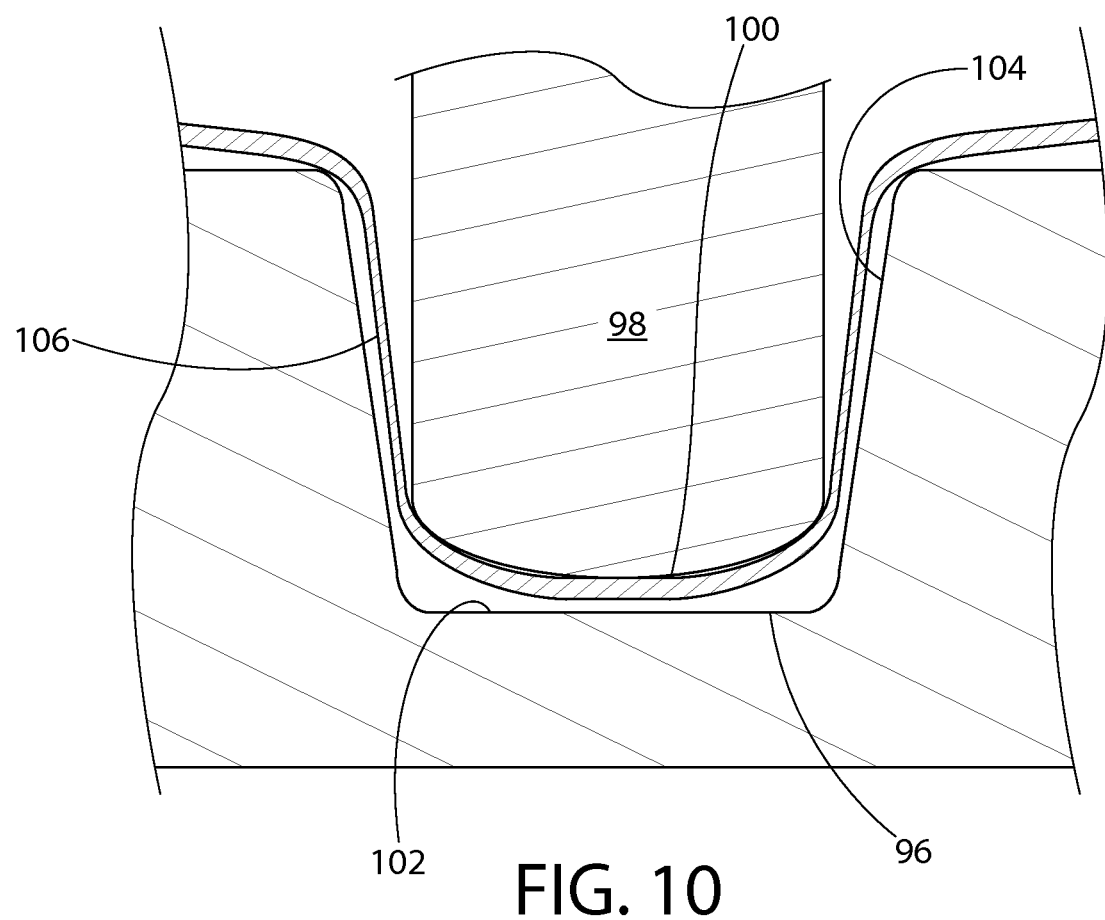
FIG. 10 illustrates the coating preform of the film coating formed by the forming die and forming plug of FIG. 9.

For example, FIG. 8 illustrates a cross sectional view of a film coated plunger, and more specifically, a plunger 12" having at least one rib 152, and more specifically three ribs 152, as well as a film coating 88 on an exterior surface 86 of the plunger 12". According to certain embodiments, the sidewall 90 of the plunger 12" may be coated in a material that minimizes friction between the plunger 12" and the sidewall 58 of the barrel 56 as the plunger 12" is displaced in the barrel 56 during dispensing of the injection product. Additionally, according to certain embodiments, the nose cone 92 of the plunger 12" may be coated in a material that isolates the plunger 12", and more specifically the material of the plunger 12" and any contaminants thereon, from the injection product contained in product containing area 59 of the barrel 56. Additionally, according to certain embodiments, the film coating 88 may have different thicknesses at different portions of the exterior surface 86 of the plunger 12", such as, for example, the nose cone 92 having a layer of the film coating 88 that is thicker than the layer of the film coating 88 along the sidewall 90. For example, according to certain embodiments the film coating 88 about the nose cone 92 may have a thickness of approximately 50 micrometer (μm), while the thickness of the film coating 88 along the sidewall may be approximately 25-35 micrometer (μm). Such differences in coating thicknesses may limit interference the film coating 88 may provide to the ability of the plunger 12" to assert a compressive force against the sidewall 58 of the barrel 56 while also providing a sufficiently thick barrier between the material of the plunger 12" and the injection product stored in the product containing area 59. Additionally, according to other embodiments, the film coating 88 may be applied to the nose cone 92 but not the sidewall 90, or vice versa.

A variety of different materials may be employed for the film coating 88 (or cap), such as, for example, an inert fluoropolymer, including, fluorinated ethylene propylene (FEP), ethylene tetrafluoroethylene (ETFE), polytetrafluoroethylene (PTFE), ethylene perfluoroethylenepropylene (EFEP), ethylene chlorotrifluoroethylene (ECTFE), Polychlorotrifluoroethene (PCTFE), perfluoroalkoxy (PFA), among other coatings. Optionally, CPT fluoropolymer may be used. CPT is a modified perfluoroalkoxy (PFA) commercially available from Daikin America, Inc. and generally comprises the addition of PCTFE side chains to a PFA main chain during polymerization, thereby increasing gas and/or liquid barrier properties of standard PFA. Optionally, a perfluoropolyether oil, such as DEMNUM which is commercially available from Daikin America, Inc., may be mixed with resin and extruded into a film, mold or cap. Additionally, according to certain embodiments, the material used for the film coating 88 may not be an expanded fluoropolymer. Further, according to certain embodiments, additives may be added to the material for the film coating 88, such as additives that may improve the adhesion of the film coating 88 to the plunger 12" and/or decrease the friction between the plunger 12" and the sidewall 58 of the barrel. Additionally, according to certain embodiments, an adhesion promoting coating or process may be employed, such as, for example, a corona treatment.

For some applications, it may be desirable to coextrude different materials to form the film. For example, coextruded film combinations may include a cyclic olefin copolymer (COC) with Aclar, Polyethylene (PE) with Aclar and FEP with PE, among other combinations.

For example, according to certain embodiments, a lubricity additive, such as a poly(tetrafluoroethylene) (PTFE) or Teflon® powder may be utilized with a thermoformed film to improve the lubricity of the film coating 88. For example, according to certain embodiments, the additive, such as the PTFE, may be applied and/or pressed into the film that is going to be used for the film coating 88 of the plunger 12". According to certain embodiments, an additive such as PTFE may only be applied to the side of the film for which the additive will have an application, such the side of the film that will be in contact with the sidewall if the additive is to reduce friction between the plunger 12" and the sidewall 58 of the barrel 56, or a side of the film that will assist in adhering the film to the plunger 12". Further, according to certain embodiments, the additive may be added to the film before the film is produce in the film form that is applied to the plunger 12".

The film coating 88 may be applied to the plunger 12", or a portion of the plunger 12", in a variety of different manners. For example, referencing FIG. 9, the film coating 88 may, prior to being applied to the plunger 12", be in the form of a film 94 (with or without the above discussed additives), such as a film of a thermoformed FEP or other thermoformable fluoropolymer, that is placed over one or more forming dies 96. As shown, heat may be applied to at least a portion of the film 94 to assist in molding the film 94 into the desired shape of the forming die 96. However, in the present example, the sidewall 90 of the plunger 12" may be coated with a thinner layer of film coating 88 than the layer covering the nose cone 92. This differential thickness is obtainable in part because of the different degree of drawing of the film 94 between the sidewall 90 and the nose cone 92. Optionally, however, this differential thickness can be increased by providing that at least the portion of the forming plug 98 that is to contact the film 94, such as, for example a base wall 100, may be relatively cool. According to certain embodiments, the temperature of the cooled forming plug 98 and/or base wall 100 of the forming plug 98 may depend on the material of the film 94. For example, according to certain embodiments, the cooled portion of the forming plug 98 may have a temperature that is cooled to approximately 25-50 degrees Celsius lower than the melt temperature of the film 94. By maintaining the forming plug 98 at a relatively lower, or cool, temperature, the stretching of the film 94 that may occur as the forming plug 98 presses a portion of the film 94 into the forming die 96 may occur to a greater extent at the portion of the film 94 that will eventually be along the sidewall 90 of the plunger 12". Moreover, with respect to the forming die 96, as shown for example in FIG. 10, by maintaining the forming plug 98 at a relatively low or cool temperature, the forming die and plug 96, 98 may be used to form a coating preform 106 of the film coating 88 in which the portion of the film 94 that was pressed into a bottom portion 102 of the forming die 96 remains thicker in relation to the portion of the film 94 that is along the sidewall 104 of the forming die 96.

According to certain embodiments, multiple positions of the forming plug 98 and forming die 96 are arranged based on mold cavitation. Thus, a plurality of coating preforms 106 of the coatings 88 may be maintained on a single piece, or web, of film 94. Thus, each coating preform 106 of the film coating 88 on the film 94 may be maintained in position on the film 94. The coating preforms 106 the may be transported together on the film 94 through the entire process by indexing at each step. However, according to other embodiments, rather than transporting the coating preforms 106 together via the coating preforms 106 being connected to the film 94, the coating preforms 106 may be removed from the film prior to other operations, such as, for example, prior to the coating preform 106 being placed into a mold cavity 108, as discussed below.

Optionally, a fluoropolymer cap may be formed and inserted into the mold after the film material has been inserted into the mold and before the plunger material is injected into the mold. Thus, in the final product, the plunger may comprise a plunger material, a fluoropolymer cap disposed on the tip of the plunger material and a film covering the cap and the plunger material. The cap may be made from fluoropolymers such as, for example, high density polyethylene (HDPE), low density polyethylene (LDPE), or PTFE, among others.

Optionally, PTFE powder may be embedded on the surface of the plunger material. This may be achieved, for example, by coating the mold cavity with PTFE powder and injecting the plunger material into the mold to form the plunger. The PTFE would provide lubricity needed for inserting and operating the plunger in a cartridge or syringe barrel.

Alternatively, a high durometer, lubricious TPE material may be used as the plunger material and have no film disposed thereon.

Figure 11:
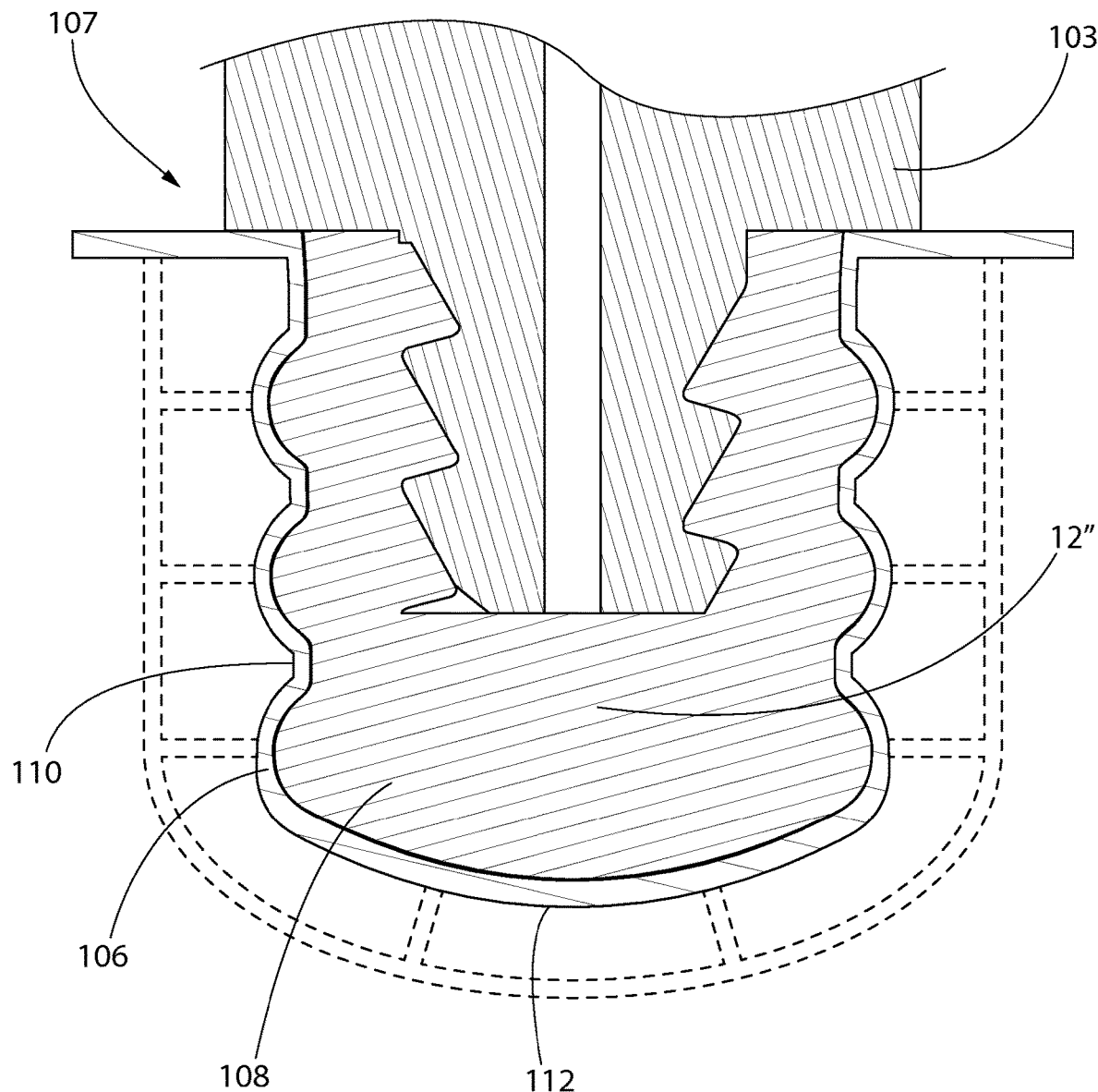
FIG. 11 illustrates the coating preform subjected to a vacuum in a mold cavity and in which a material for a plunger has been injected into the mold cavity and is against the coating preform.

FIG. 11 illustrates a coating preform 106 formed from the film 104 after the coating preform 106 has been loaded into a mold cavity 108 of a mold 107 and a vacuum has been applied to pull the coating preform 106 against the sidewall 110 and bottom wall 112 of the mold cavity 108. Thus, according to certain embodiments, the shape of the film coating 88 may have a contour that matches the desired outer shape of the plunger 12". With the mold 107 closed, a material for the plunger 12", such as, for example, thermoset rubber (e.g., butyl rubber) or a thermoplastic elastomer (TPE) may be injected into the mold cavity 108 via an injection molding process so that plunger is molded against and/or to the coating preform 106 and a mold core 103. The mold 107 may then be opened and the mold core 103 removed. The molded plunger 12" with the film coating 88 (which may be still attached to the film 94) may then be removed from the mold 107.

Figure 12:
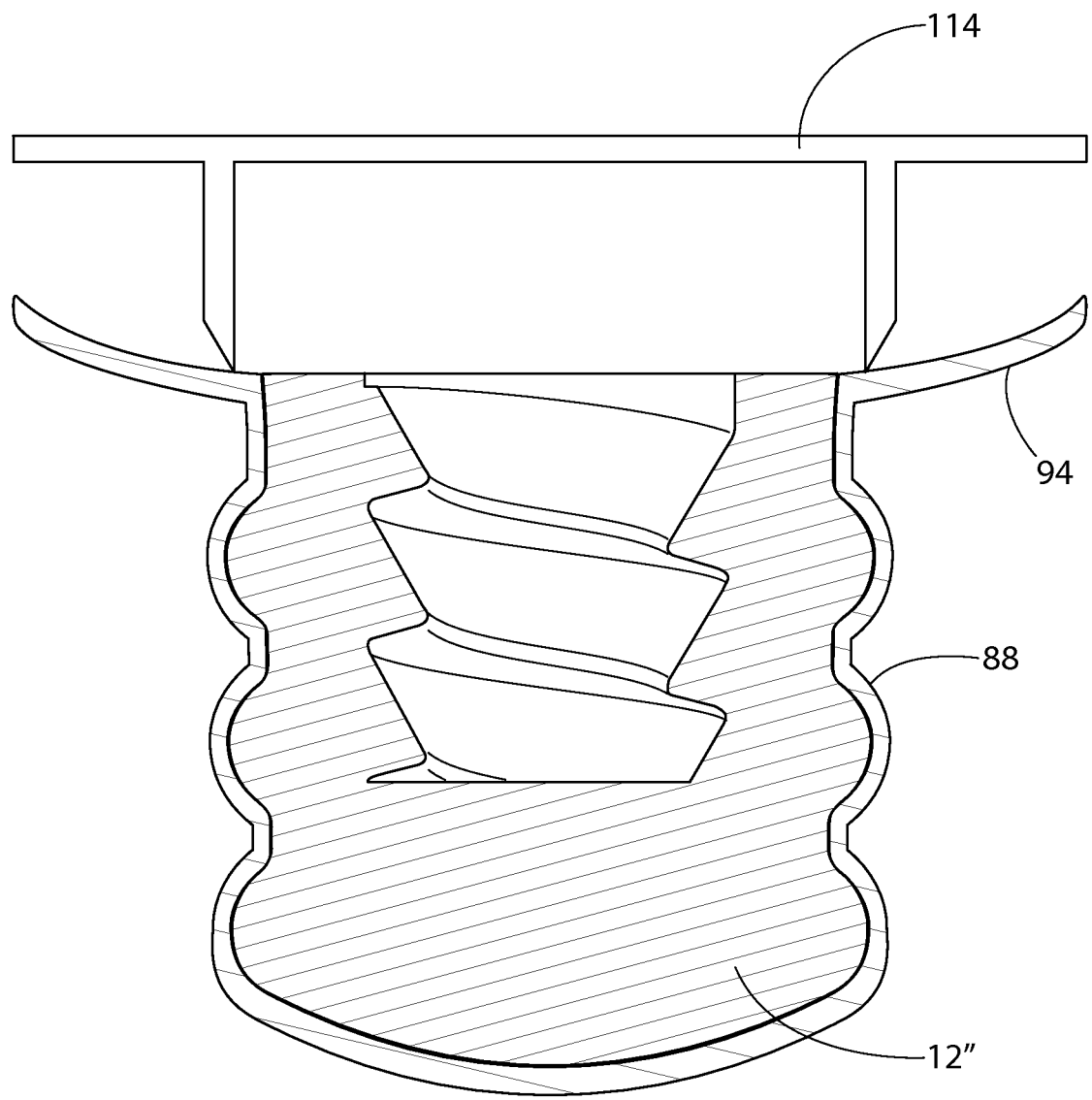
FIG. 12 illustrates a cross sectional view of a formed plunger and film coating prior to a trim tool cutting or trimming the coating from a film.

FIG. 12 illustrates the formed plunger 12" and film coating 88 prior a trim tool 114 cutting or trimming the film coating 88 away from the remainder of the film 94. While the trim tool 114 is illustrated as being a mechanical cutting device, a variety of different cutting devices may be employed, such as, for example, a laser, among other cutters. Additionally, the timing that at least the coating preform 106 and/or film coating 88 is trimmed from the film 94 may vary. For example, according to certain embodiments, the coating preform 106 and/or film coating 88 may remain connected to the film 94 so that the coating preform 106 and/or film coating 88 may be used to convey a plurality of coating preforms 106 and/or film coatings 88 during the manufacturing process (without or without the plunger 12"). According to such an embodiment, the coating preform(s) 106 and/or film coating(s) 88 may remain attached to the film 94 up until the time that coating preform(s) 106 and/or film coating(s) 88 are trimmed from the film 94.

The material used for the film coating 88 may provide the compliance needed for the sealing function of the barrel 56, as previously discussed. Further, by being able to use certain materials for the film coating 88, such as, for example, a fluoropolymer film, a broader selection of materials for use in forming the plunger 12" may be available, as the film coating 88 applied to the nose cone 92 will provide a barrier between the material of the plunger 12" and the injection product contained in the barrel 56. Further, according to certain embodiments, the plunger 12" may be configured to limit the degree to which the rib(s) 52 and/or plunger 12" are compressed when the plunger 12" is inserted into the barrel 56. For example, according to certain embodiments, the rib(s) 52 and/or plunger 12" is configured to not be compressed more than 20% of the overall width of the rib 52 and/or plunger 12" when the plunger 12" is being used to form a seal in the barrel 56. Alternative options for compression percentages are provided above.

Figure 26:
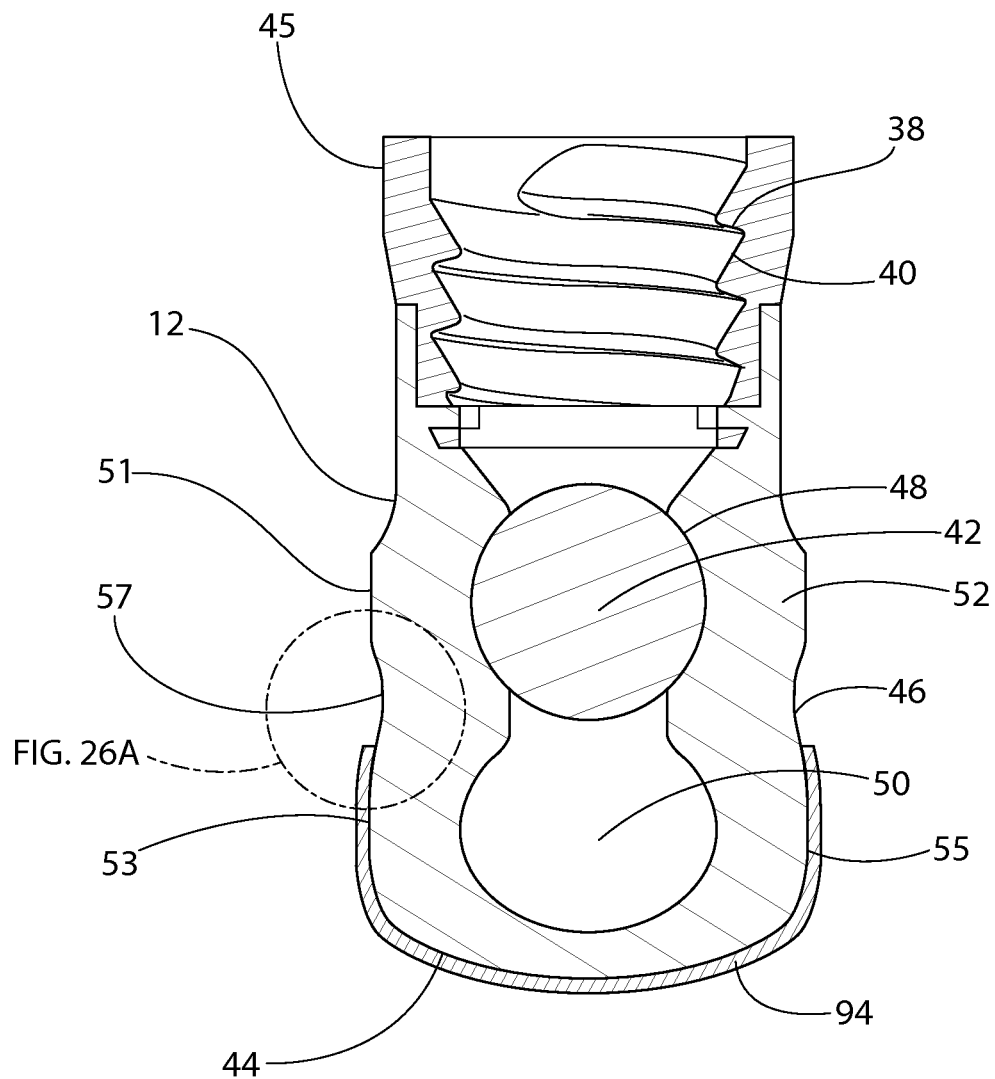
FIG. 26 illustrates an isolated partial sectional view of an exemplary embodiment of a film coated convertible plunger.
Figure 26A:
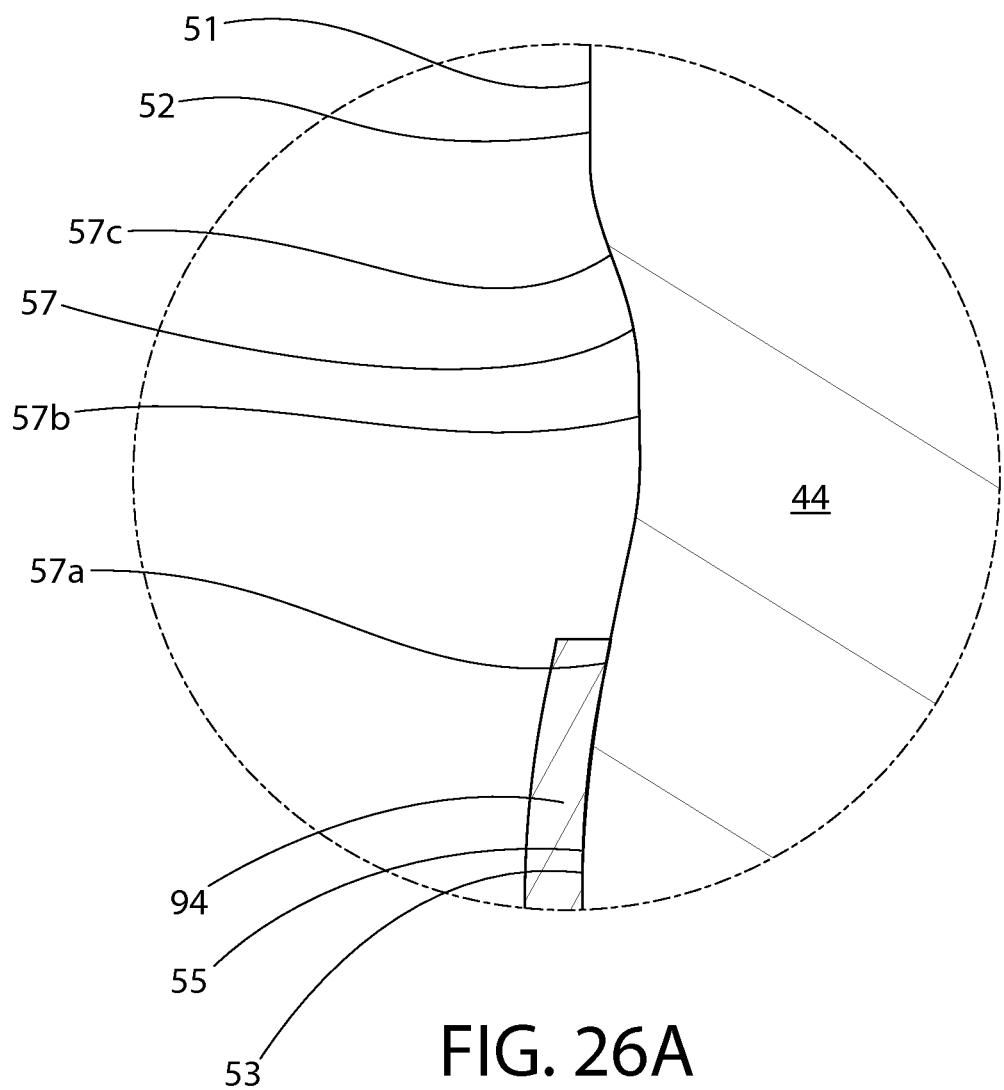
FIG. 26A illustrates an enlarged sectional view of the sidewall of the film coated convertible plunger of FIG. 26.

Referring to FIG. 26, there is shown a film coated plunger 12 according to the present invention. The film coated plunger 12 comprises a plunger sleeve 44 (e.g., same as that of FIG. 3) having a film coating 88 mounted over the nose cone 92 and a portion of the sidewall 90 of the film coated plunger 12. Preferably, as shown, the film coating 88 covers the entire nose cone 92. The film coating 88 also optionally covers the rib 55 of the liquid sealing section 53 and optionally a small section of the valley 57 adjacent to the rib 55. Optionally, as shown in FIG. 26A, the valley 57 comprises a descending slope 57a extending distally from the liquid sealing section 53, the descending slope 57a leading to a floor 57b, the floor 57b leading to an ascending slope 57c toward the storage sealing section 51. Optionally, the film coating 88 terminates before the storage sealing section 51, optionally before the ascending slope 57c, optionally before the floor 57b. In any event, there is preferably no film coating 88 covering the rib 52 of the storage sealing section 51, since thermoset rubber (if that is the material of the rib 52) is a better oxygen barrier than contemplated film materials. The film coating 88 may be made, e.g., from any materials disclosed herein that are suitable for film coatings, e.g., an inert fluoropolymer, optionally polyethylene or polypropylene.

Optionally, the film coated plunger of FIG. 26 may be part of a plunger assembly 10, 210 described herein and shown in FIG. 2 or 13. Optionally, the film coated plunger of FIG. 26 is any one of the plunger embodiments described herein and shown in FIG. 3, 7, 8, 15, 17, 18, 20, 21, 22, 23, 24 or 25. Optionally, the film coated plunger of FIG. 26 provides a first sealing force against an interior surface of a barrel wall in storage mode and a second sealing force (which is less than the first sealing force) in dispensing mode. Optionally, the first sealing force is provided by a compression material contained within the plunger 12 and aligned, at least in part, with a rib 52 of the storage sealing section 51. The compression material is configured to provide outward radial force. The second sealing force is attainable by displacing and/or modifying the compression material, for example, in the many ways described herein.

The film coating 88 may be mounted to the plunger sleeve 44 in various ways. For example, a flat film piece may be placed onto a first surface of a forming block having a round passage leading to a second surface on another side of the forming block. At least an end portion of the round passage leading to the second surface of the forming block has roughly the same diameter as the plunger. A plunger holder grips a substantial portion of the plunger from the rear thereof (e.g., leaving uncovered that portion of the plunger to be covered with film). The plunger holder may be axially driven through the passage of the forming block, e.g., with a (preferably automated) pushing rod. Optionally, the pushing rod protrudes into the plunger cavity (e.g., 48 and optionally 50 of the plunger 12 of FIG. 26), slightly stretching the plunger. Optionally, prior to axially inserting the plunger and plunger holder through the passage, the plunger is heated e.g., to 100° C. to 200° C., optionally 110° C. to 190° C., optionally 120° C. to 180° C., optionally 130° C. to 170° C., optionally 135° C. to 160° C., optionally 145° C. to 155° C., optionally about 150° C.

After the optional heating step (if taken), the plunger and plunger holder are axially inserted through the passage thereby mounting the film piece to the plunger. Excess sections of the film piece may be trimmed from the plunger. For high volume production, for example, flat, continuous film strips may be preferred to individual film sheets for each plunger. Alternatively, continuous film strips may be perforated or otherwise weakened in circular patterns so as to provide pre-sized circular films for mounting to plungers. Preferably, such pre-sized circular films would be sized so as to leave no excess film to trim once mounted on the plunger. In this way, the plunger holder and plunger may be aligned with the circular patterns in order to punch through them when the plunger is inserted into the passage so as to mount the pre-sized circular films onto the plunger. Optionally, the film may be applied via cold forming (preferred) or thermoforming, wherein the plunger sleeve is itself used in the thermoforming process (e.g., mold rubber plunger sleeve and then thermoform film to rubber).

Figure 27:
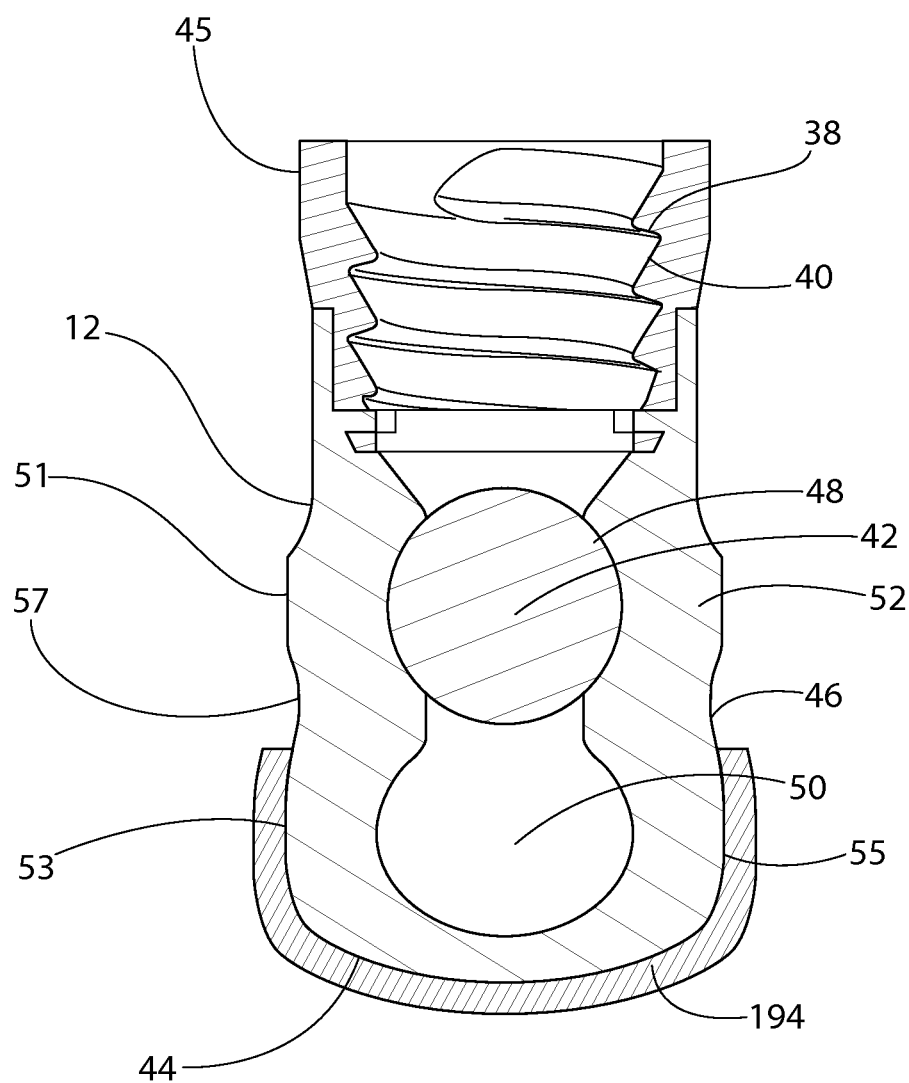
FIG. 27 illustrates an isolated partial sectional view of an exemplary embodiment of a cap covered convertible plunger.

Referring to FIG. 27, there is shown the plunger sleeve 44 of FIG. 3 having a cap 194 mounted over the nose cone 92 and a portion of the sidewall 90 of the plunger 12. Preferably, as shown, the cap 194 covers the entire nose cone 92. The cap 194 also covers the rib 55 of the liquid sealing section 53 and a small section of the valley 57 adjacent to the rib 55. Preferably, the cap 194 does not cover the rib 52 of the storage sealing section 51. Optionally, the cap 194 terminates in the same places in the valley 57 as described above vis-à-vis the film coating 88 as shown in FIG. 26A. The cap 194 may be made from fluoropolymers such as, for example, high density polyethylene (HDPE), low density polyethylene (LDPE), or PTFE, among others. While it is contemplated that the cap 194 may have a thickness greater than that of the film 94 discussed above, it should be understood that the thickness of the cap 194 as shown in FIG. 27 is not to scale, but is exaggerated for purposes of clarity.

The cap 194 is preferably an injection molded part that is made in a two shot injection mold process with the sleeve 44. In other words, optionally, a cap material (e.g. polymer) is injection molded and subsequently the sleeve material (e.g. rubber) is injection molded into the same mold cavity as the cap material in a two shot process. Optionally, in molding, the cap 194 and sleeve 44 mate together through a mechanical fit such as an interference fit. Advantageously, the cap can be made from either thermoplastic or thermoset materials. In addition, a molded cap is an easier component to manage in manufacturing than a comparatively thinner film.

The use of the fluoropolymer powders may be used in combination with non-fluoropolymer films—like polyethylene or polypropylene films that are more adhesion compatible with the thermoplastic elastomer/rubber plunger materials. The challenge with fluoropolymer films—like FEP is that they may not perfectly adhere to the plunger and can wrinkle when interested into the syringe barrel.

A potential solution to the problems of film adhesion and wrinkling contemplated by the inventors is to make the plunger from a liquid silicone rubber, preferably a fluoro liquid silicone rubber. Fluoro liquid silicone rubbers are injection moldable materials that possess good compression set properties, e.g., for long term storage in pre-filled cartridges or syringes, similar to butyl rubber. In addition, they adhere well to fluoropolymers. As such, according to one aspect of the invention, a fluoro liquid silicone rubber plunger (optionally incorporating features of any plunger embodiments disclosed herein) is provided, having a fluoropolymer film disposed thereon. The fluoro liquid silicone rubber plunger provides enhanced bonding with the fluoropolymer film, and thus resists wrinkling of the film. This enhanced bonding and wrinkle resistance would render the plunger more robust for handling and insertion into a syringe or cartridge. An additional potential advantage is that fluoro liquid silicone rubber may be injection molded to achieve better dimensional tolerances than traditional compression molded plungers, such as those made from butyl rubber.

In another embodiment, a fluoro liquid silicone rubber plunger is provided which does not include a film disposed thereon. It is contemplated that for some applications, a plunger comprising fluoro liquid silicone rubber will itself (without a film) have adequate compression set properties and would be sufficiently lubricious for insertion and handling in a cartridge or syringe barrel.

Examples of potentially suitable fluoro liquid silicone rubber materials for use in plungers according to an aspect of the present invention include, among others, SILASTIC® marketed by Dow Corning Corporation and ELASTOSIL® FLR marketed by Wacker Chemie AG.

It is contemplated that fluoro liquid silicone polymer plungers may have comparable or superior properties, in several respects (e.g., in terms of compression setting, film adhesion, plunger force, and plunger extractables), compared to standard, e.g., butyl rubber plungers.

It is contemplated that any of the convertible plungers described in this specification and shown in the drawing figures may optionally include film coatings or molded caps as described herein.

It is further contemplated that any of the plungers described herein, whether or not they include a film coating, may be made from one or more materials including, but not limited to, a thermoset rubber (e.g., butyl rubber), a thermoplastic elastomer (TPE), liquid silicone rubber and fluoro liquid silicone rubber. It is further contemplated that any plunger embodiments that are described herein without a film may include a film and that any plunger embodiments that are described herein with a film may be used without a film, depending on design requirements and/or functional needs.

Plunger Testing Methods and Standards

Testing of compression setting properties of the plunger may be conducted using methods known in the art, for example, ASTM D395.

Testing of adhesive properties or bonding strength between the film and the plunger may be conducted using methods known in the art, for example, according to ASTM D1995-92(2011) or D1876-08.

Plunger sliding force is the force required to maintain movement of a plunger in a syringe or cartridge barrel, for example during aspiration or dispense. It can advantageously be determined using, e.g., the ISO 7886-1:1993 test known in the art, or to the currently pending published test method to be incorporated into ISO 11040-4. Plunger breakout force, which may be tested using the same method as that for testing plunger sliding force, is the force required to start a stationary plunger moving within a syringe or cartridge barrel. Machinery useful in testing plunger sliding and breakout force is, e.g., an Instron machine using a 50 N transducer.

Testing for extractables, i.e., amount of material that migrates from the plunger into the liquid within the syringe or cartridge, may be conducted using methods set forth in Ph. Eur. 2.9.17 Test for Extractable Volume of Parenteral Preparations, for example.

Testing of container closure integrity (CCI) may be done using a vacuum decay leak detection method, wherein a vacuum his maintained inside of a test volume and pressure rise is measured over time. A large enough pressure rise is an indication that there is flow into the system, which is evidence of a leak. Optionally, the vacuum decay test is implemented over two separate cycles. The first cycle is dedicated to detecting large leaks over a very short duration. A relatively weak vacuum is pulled for the first cycle because if a gross leak is detected, a large pressure differential is not necessary to detect a large pressure rise. Use of a first cycle as described helps to shorten total test time if a gross leak exists. If no leak is detected in the first cycle, a second cycle is run, which complies with ASTM F2338-09 Standard Test Method for Nondestructive Detection of Leaks in Packages by Vacuum Decay Method. The second cycle starts out with a system evaluation to lower the signal to noise ratio in the pressure rise measurements. A relatively strong vacuum is pulled for a long period of time in the second cycle to increase the chance of detecting a pressure rise in the system.

Syringe Embodiments and PECVD Coatings

In another aspect, the present invention includes use of any embodiments (or combination of embodiments) of plungers according to the invention in syringes having a PECVD coating or PECVD coating set. The syringes may be made from, e.g., glass or plastic. Optionally, the syringe barrel according to any embodiment is made from an injection moldable thermoplastic material that appears clear and glass-like in final form, e.g., a cyclic olefin polymer (COP), cyclic olefin copolymer (COC) or polycarbonate. Such materials may be manufactured, e.g., by injection molding, to very tight and precise tolerances (generally much tighter than achievable with glass). This is a benefit when trying to balance the competing considerations of seal tightness and low plunger force in plunger design.

This section of the disclosure focuses primarily on pre-filled syringes as a preferred implementation of optional aspects of the invention. Again, however, it should be understood that the present invention may include any parenteral container that utilizes a plunger, such as syringes, cartridges, auto-injectors, pre-filled syringes, pre-filled cartridges or vials.

For some applications, it may be desired to provide one or more coatings or layers to the interior wall of a parenteral container to modify the properties of that container. For example, one or more coatings or layers may be added to a parenteral container, e.g., to improve the barrier properties of the container and prevent interaction between the container wall (or an underlying coating) and drug product held within the container.

For example, as shown in FIG. 4A, which is a first alternative embodiment of an enlarged sectional view of the syringe barrel 54 of FIG. 4, the sidewall 58 of the syringe barrel 54 may include a coating set 400 comprising one or more coatings or layers. The barrel 54 may include at least one tie coating or layer 402, at least one barrier coating or layer 404, and at least one organo-siloxane coating or layer 406. The organo-siloxane coating or layer 406 preferably has pH protective properties. This embodiment of the coating set 400 is referred to herein as a "trilayer coating set" in which the the barrier coating or layer 404 of $SiO_x$ is protected against contents having a pH otherwise high enough to remove it by being sandwiched between the pH protective organo-siloxane coating or layer 406 and the tie coating or layer 402. The contemplated thicknesses of the respective layers in nm (preferred ranges in parentheses) are given in the following Trilayer Thickness Table:

| Trilayer Thickness Table | | |
|---|---|---|
| Adhesion | Barrier | Protection |
| 5-100 | 20-200 | 50-500 |
| (5-20) | (20-30) | (100-200) |

Properties and compositions of each of the coatings that make up the trilayer coating set are now described.

The tie coating or layer 402 has at least two functions. One function of the tie coating or layer 402 is to improve adhesion of a barrier coating or layer 404 to a substrate (e.g., the sidewall 58 of the barrel 54), in particular a thermoplastic substrate, although a tie layer can be used to improve adhesion to a glass substrate or to another coating or layer. For example, a tie coating or layer, also referred to as an adhesion layer or coating can be applied to the substrate and the barrier layer can be applied to the adhesion layer to improve adhesion of the barrier layer or coating to the substrate.

Another function of the tie coating or layer 402 has been discovered: a tie coating or layer 402 applied under a barrier coating or layer 404 can improve the function of a pH protective organo-siloxane coating or layer 406 applied over the barrier coating or layer 404.

The tie coating or layer 402 can be composed of, comprise, or consist essentially of $SiO_xC_y$, in which x is between 0.5 and 2.4 and y is between 0.6 and 3. Alternatively, the atomic ratio can be expressed as the formula $Si_wO_xC_y$. The atomic ratios of Si, O, and C in the tie coating or layer 289 are, as several options:

Si 100:O 50-150:C 90-200 (i.e. w=1, x=0.5 to 1.5, y=0.9 to 2);

Si 100:O 70-130:C 90-200 (i.e. w=1, x=0.7 to 1.3, y=0.9 to 2)

Si 100:O 80-120:C 90-150 (i.e. w=1, x=0.8 to 1.2, y=0.9 to 1.5)

Si 100:O 90-120:C 90-140 (i.e. w=1, x=0.9 to 1.2, y=0.9 to 1.4), or

Si 100:O 92-107:C 116-133 (i.e. w=1, x=0.92 to 1.07, y=1.16 to 1.33).

The atomic ratio can be determined by XPS. Taking into account the H atoms, which are not measured by XPS, the tie coating or layer 402 may thus in one aspect have the formula $Si_wO_xC_yH_z$ (or its equivalent $S_iO_xC_y$), for example where w is 1, x is from about 0.5 to about 2.4, y is from about 0.6 to about 3, and z is from about 2 to about 9. Typically, a tie coating or layer 402 would hence contain 36% to 41% carbon normalized to 100% carbon plus oxygen plus silicon.

The barrier coating or layer for any embodiment defined in this specification (unless otherwise specified in a particular instance) is a coating or layer, optionally applied by PECVD as indicated in U.S. Pat. No. 7,985,188. The barrier coating preferably is characterized as a "$SiO_x$" coating, and contains silicon, oxygen, and optionally other elements, in which x, the ratio of oxygen to silicon atoms, is from about 1.5 to about 2.9. The thickness of the $SiO_x$ or other barrier coating or layer can be measured, for example, by transmission electron microscopy (TEM), and its composition can be measured by X-ray photoelectron spectroscopy (XPS). The barrier layer is effective to prevent oxygen, carbon dioxide, or other gases from entering the container and/or to prevent leaching of the pharmaceutical material into or through the container wall.

Referring again to FIG. 4A, the barrier coating or layer 404 of $SiO_x$, in which x is between 1.5 and 2.9, is applied by plasma enhanced chemical vapor deposition (PECVD) directly or indirectly to the thermoplastic sidewall wall 58 of the barrel 54 (in this example, a tie coating or layer 402 is interposed between them) so that in the filled syringe barrel 54, the barrier coating or layer 404 is located between the inner or interior surface of the sidewall 55 of the barrel 54 and the injectable medicine contained within the barrel 54.

Certain barrier coatings or layers 404 such as SiOx as defined here have been found to have the characteristic of being subject to being measurably diminished in barrier improvement factor in less than six months as a result of attack by certain relatively high pH contents of the coated vessel as described elsewhere in this specification, particularly where the barrier coating or layer directly contacts the contents. This issue can be addressed using an organo-siloxane coating or layer as discussed in this specification.

Preferred methods of applying the barrier layer and tie layer to the inner surface of the barrel 54 is by plasma enhanced chemical vapor deposition (PECVD), such as described in, e.g., U.S. Pat. App. Pub. No. 20130291632, which is incorporated by reference herein in its entirety.

The Applicant has found that barrier layers or coatings of $SiO_x$ are eroded or dissolved by some fluids, for example aqueous compositions having a pH above about 5. Since coatings applied by chemical vapor deposition can be very thin—tens to hundreds of nanometers thick—even a relatively slow rate of erosion can remove or reduce the effectiveness of the barrier layer in less time than the desired shelf life of a product package. This is particularly a problem for fluid pharmaceutical compositions, since many of them have a pH of roughly 7, or more broadly in the range of 5 to 9, similar to the pH of blood and other human or animal fluids. The higher the pH of the pharmaceutical preparation, the more quickly it erodes or dissolves the $SiO_x$ coating. Optionally, this problem can be addressed by protecting the barrier coating or layer 404, or other pH sensitive material, with a pH protective organo-siloxane coating or layer 406.

Optionally, the pH protective organo-siloxane coating or layer 406 can be composed of, comprise, or consist essentially of $Si_wO_xC_yH_z$ (or its equivalent $SiO_xC_y$) or $Si_wN_xC_yH_z$ or its equivalent $SiN_xC_y$). The atomic ratio of Si:O:C or Si:N:C can be determined by XPS (X-ray photoelectron spectroscopy). Taking into account the H atoms, the pH protective coating or layer may thus in one aspect have the formula $Si_wO_xC_yH_z$, or its equivalent $SiO_xC_y$, for example where w is 1, x is from about 0.5 to about 2.4, y is from about 0.6 to about 3, and z is from about 2 to about 9.

Typically, expressed as the formula $Si_wO_xC_y$, the atomic ratios of Si, O, and C are, as several options:
Si 100:O 50-150:C 90-200 (i.e. w=1, x=0.5 to 1.5, y=0.9 to 2);
Si 100:O 70-130:C 90-200 (i.e. w=1, x=0.7 to 1.3, y=0.9 to 2)
Si 100:O 80-120:C 90-150 (i.e. w=1, x=0.8 to 1.2, y=0.9 to 1.5)
Si 100:O 90-120:C 90-140 (i.e. w=1, x=0.9 to 1.2, y=0.9 to 1.4)
Si 100:O 92-107:C 116-133 (i.e. w=1, x=0.92 to 1.07, y=1.16 to 1.33), or
Si 100:O 80-130:C 90-150.

Alternatively, the organo-siloxane coating or layer can have atomic concentrations normalized to 100% carbon, oxygen, and silicon, as determined by X-ray photoelectron spectroscopy (XPS) of less than 50% carbon and more than 25% silicon. Alternatively, the atomic concentrations are from 25 to 45% carbon, 25 to 65% silicon, and 10 to 35% oxygen. Alternatively, the atomic concentrations are from 30 to 40% carbon, 32 to 52% silicon, and 20 to 27% oxygen. Alternatively, the atomic concentrations are from 33 to 37% carbon, 37 to 47% silicon, and 22 to 26% oxygen.

Optionally, the atomic concentration of carbon in the pH protective coating or layer 406, normalized to 100% of carbon, oxygen, and silicon, as determined by X-ray photoelectron spectroscopy (XPS), can be greater than the atomic concentration of carbon in the atomic formula for the organosilicon precursor. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the pH protective coating or layer 406 can be increased in comparison to the organosilicon precursor, and/or the atomic ratio of oxygen to silicon can be decreased in comparison to the organosilicon precursor.

An exemplary empirical composition for a pH protective coating according to the present invention is $SiO_{1.3}Co_{0.8}H_{3.6}$.

Optionally in any embodiment, the pH protective coating or layer 406 comprises, consists essentially of, or consists of PECVD applied silicon carbide.

Optionally in any embodiment, the pH protective coating or layer 406 is applied by employing a precursor comprising, consisting essentially of, or consisting of a silane. Optionally in any embodiment, the silane precursor comprises, consists essentially of, or consists of any one or more of an acyclic or cyclic silane, optionally comprising, consisting essentially of, or consisting of any one or more of silane, trimethylsilane, tetramethylsilane, Si2-Si4 silanes, triethyl silane, tetraethyl silane, tetrapropylsilane, tetrabutylsilane, or octamethylcyclotetrasilane, or tetramethylcyclotetrasilane.

Optionally in any embodiment, the pH protective coating or layer 406 comprises, consists essentially of, or consists of PECVD applied amorphous or diamond-like carbon. Optionally in any embodiment, the amorphous or diamond-like carbon is applied using a hydrocarbon precursor. Optionally in any embodiment, the hydrocarbon precursor comprises, consists essentially of, or consists of a linear, branched, or cyclic alkane, alkene, alkadiene, or alkyne that is saturated or unsaturated, for example acetylene, methane, ethane, ethylene, propane, propylene, n-butane, i-butane, butane, propyne, butyne, cyclopropane, cyclobutane, cyclohexane, cyclohexene, cyclopentadiene, or a combination of two or more of these. Optionally in any embodiment, the amorphous or diamond-like carbon coating has a hydrogen atomic percent of from 0.1% to 40%, alternatively from 0.5% to 10%, alternatively from 1% to 2%, alternatively from 1.1 to 1.8%.

Optionally in any embodiment, the pH protective coating or layer 406 comprises, consists essentially of, or consists of PECVD applied SiNb. Optionally in any embodiment, the PECVD applied SiNb is applied using a silane and a nitrogen-containing compound as precursors. Optionally in any embodiment, the silane is an acyclic or cyclic silane, optionally comprising, consisting essentially of, or consisting of silane, trimethylsilane, tetramethylsilane, Si2-Si4 silanes, triethylsilane, tetraethylsilane, tetrapropylsilane, tetrabutylsilane, octamethylcyclotetrasilane, or a combination of two or more of these. Optionally in any embodiment, the nitrogen-containing compound comprises, consists essentially of, or consists of any one or more of: nitrogen gas, nitrous oxide, ammonia or a silazane. Optionally in any embodiment, the silazane comprises, consists essentially of, or consists of a linear silazane, for example hexamethylene disilazane (HMDZ), a monocyclic silazane, a polycyclic silazane, a polysilsesquiazane, or a combination of two or more of these.

Optionally in any embodiment, the PECVD for the pH protective coating or layer 406 is carried out in the substantial absence or complete absence of an oxidizing gas. Optionally in any embodiment, the PECVD for the pH protective coating or layer 406 is carried out in the substantial absence or complete absence of a carrier gas.

Optionally an FTIR absorbance spectrum of the pH protective coating or layer 406 SiOxCyHz has a ratio greater than 0.75 between the maximum amplitude of the Si—O—Si symmetrical stretch peak normally located between about 1000 and 1040 cm−1, and the maximum amplitude of the Si—O—Si asymmetric stretch peak normally located between about 1060 and about 1100 cm−1. Alternatively in any embodiment, this ratio can be at least 0.8, or at least 0.9, or at least 1.0, or at least 1.1, or at least 1.2. Alternatively in any embodiment, this ratio can be at most 1.7, or at most 1.6, or at most 1.5, or at most 1.4, or at most 1.3. Any minimum ratio stated here can be combined with any maximum ratio stated here, as an alternative embodiment.

Optionally, in any embodiment the pH protective coating or layer 406, in the absence of the medicament, has a non-oily appearance. This appearance has been observed in some instances to distinguish an effective pH protective coating or layer 406 from a lubricity layer (e.g., as described in U.S. Pat. No. 7,985,188), which in some instances has been observed to have an oily (i.e. shiny) appearance.

The pH protective coating or layer 406 optionally can be applied by plasma enhanced chemical vapor deposition (PECVD) of a precursor feed comprising an acyclic siloxane, a monocyclic siloxane, a polycyclic siloxane, a polysilsesquioxane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors. Some particular, non-limiting precursors contemplated for such use include octamethylcyclotetrasiloxane (OMCTS).

Optionally, an FTIR absorbance spectrum of the pH protective coating or layer 406 of composition SiOxCyHz has a ratio greater than 0.75 between the maximum amplitude of the Si—O—Si symmetrical stretch peak between about 1000 and 1040 cm−1, and the maximum amplitude of the Si—O—Si asymmetric stretch peak between about 1060 and about 1100 cm−1.

Other precursors and methods can be used to apply the pH protective coating or layer 406 or passivating treatment. For example, hexamethylene disilazane (HMDZ) can be used as the precursor. HMDZ has the advantage of containing no oxygen in its molecular structure. This passivation treatment is contemplated to be a surface treatment of the SiOx barrier layer with HMDZ. To slow down and/or eliminate the decomposition of the silicon dioxide coatings at silanol bonding sites, the coating must be passivated. It is contemplated that passivation of the surface with HMDZ (and optionally application of a few mono layers of the HMDZ-derived coating) will result in a toughening of the surface against dissolution, resulting in reduced decomposition. It is contemplated that HMDZ will react with the —OH sites that are present in the silicon dioxide coating, resulting in the evolution of NH3 and bonding of S—(CH3)3 to the silicon (it is contemplated that hydrogen atoms will be evolved and bond with nitrogen from the HMDZ to produce NH3).

Another way of applying the pH protective coating or layer 406 is to apply as the pH protective coating or layer 406 an amorphous carbon or fluorocarbon coating, or a combination of the two.

Amorphous carbon coatings can be formed by PECVD using a saturated hydrocarbon, (e.g. methane or propane) or an unsaturated hydrocarbon (e.g. ethylene, acetylene) as a precursor for plasma polymerization. Fluorocarbon coatings can be derived from fluorocarbons (for example, hexafluoroethylene or tetrafluoroethylene). Either type of coating, or a combination of both, can be deposited by vacuum PECVD or atmospheric pressure PECVD. It is contemplated that that an amorphous carbon and/or fluorocarbon coating will provide better passivation of an SiOx barrier layer than a siloxane coating since an amorphous carbon and/or fluorocarbon coating will not contain silanol bonds.

It is further contemplated that fluorosilicon precursors can be used to provide a pH protective coating or layer 406 over a SiOx barrier layer. This can be carried out by using as a precursor a fluorinated silane precursor such as hexafluorosilane and a PECVD process. The resulting coating would also be expected to be a non-wetting coating.

Yet another coating modality contemplated for protecting or passivating a SiOx barrier layer is coating the barrier layer using a polyamidoamine epichlorohydrin resin. For example, the barrier coated part can be dip coated in a fluid polyamidoamine epichlorohydrin resin melt, solution or dispersion and cured by autoclaving or other heating at a temperature between 60 and 100° C. It is contemplated that a coating of polyamidoamine epichlorohydrin resin can be preferentially used in aqueous environments between pH 5-8, as such resins are known to provide high wet strength in paper in that pH range. Wet strength is the ability to maintain mechanical strength of paper subjected to complete water soaking for extended periods of time, so it is contemplated that a coating of polyamidoamine epichlorohydrin resin on a SiOx barrier layer will have similar resistance to dissolution in aqueous media. It is also contemplated that, because polyamidoamine epichlorohydrin resin imparts a lubricity improvement to paper, it will also provide lubricity in the form of a coating on a thermoplastic surface made of, for example, COC or COP.

Even another approach for protecting a SiOx layer is to apply as a pH protective coating or layer 406 a liquid-applied coating of a polyfluoroalkyl ether, followed by atmospheric plasma curing the pH protective coating or layer 406. For example, it is contemplated that the process practiced under the trademark TriboGlide® can be used to provide a pH protective coating or layer 406 that is also provides lubricity.

Thus, a pH protective coating for a thermoplastic syringe wall according to an aspect of the invention may comprise, consist essentially of, or consist of any one of the following: plasma enhanced chemical vapor deposition (PECVD) applied silicon carbide having the formula SiOxCyHz, in which x is from 0 to 0.5, alternatively from 0 to 0.49, alternatively from 0 to 0.25 as measured by X ray photoelectron spectroscopy (XPS), y is from about 0.5 to about 1.5, alternatively from about 0.8 to about 1.2, alternatively about 1, as measured by XPS, and z is from 0 to 2 as measured by Rutherford Backscattering Spectrometry (RBS), alternatively by Hydrogen Forward Scattering Spectrometry (HFS); or PECVD applied amorphous or diamond-like carbon, CHz, in which z is from 0 to 0.7, alternatively from 0.005 to 0.1, alternatively from 0.01 to 0.02; or PECVD applied SiNb, in which b is from about 0.5 to about 2.1, alternatively from about 0.9 to about 1.6, alternatively from about 1.2 to about 1.4, as measured by XPS.

pH Protective Organo-Siloxane Coating—Not as Part of Coating Set

Figure 4B:
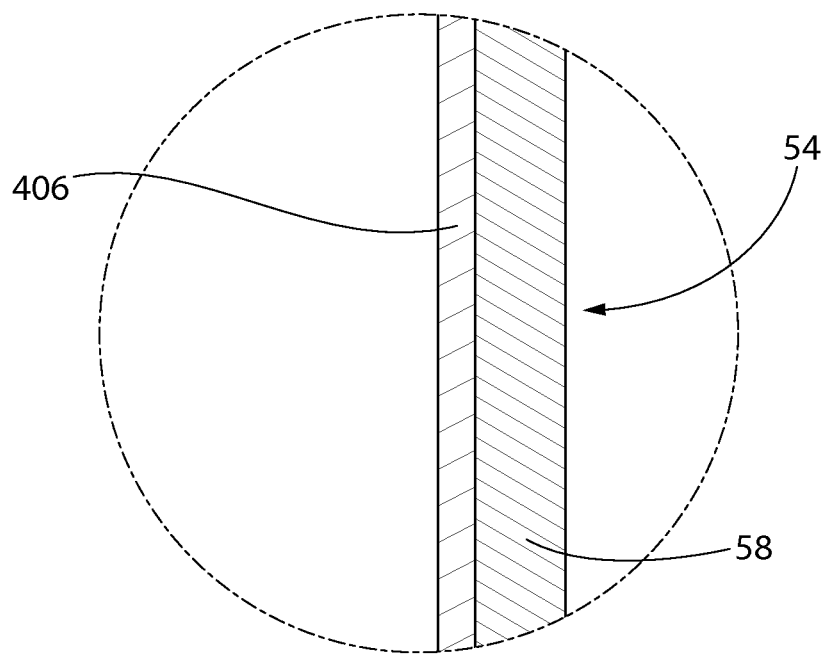
FIG. 4B an enlarged sectional view of a second alternative embodiment of the inner surface of the syringe of FIG. 4, comprising an organo-siloxane coating disposed thereon.

Referring now to FIG. 4B, there is shown a second alternative embodiment of an enlarged sectional view of the syringe barrel 54 of FIG. 4. As shown in FIG. 4B, the syringe barrel 54 may include a organo-siloxane coating or layer 406 disposed directly on the wall 58 of the syringe barrel 54, rather than, e.g., as a top layer of a coating set. Optionally, the organo-siloxane coating or layer 406 has pH protective properties. Thus an aspect of the invention involves use of a organo-siloxane coating or layer as a plunger-contacting surface, whether the organo-siloxane coating or layer is the top-most layer of a coating set or is by itself disposed directly onto the barrel wall.

PECVD Apparatus

PECVD apparatus suitable for applying any of the PECVD coatings or layers described in this specification, including the tie coating or layer 402, the barrier coating or layer 404 or the organo-siloxane coating or layer 406, is shown and described in U.S. Pat. No. 7,985,188 and U.S. Pat. App. Pub. No. 20130291632. This apparatus optionally includes a vessel holder, an inner electrode, an outer electrode, and a power supply. A vessel seated on the vessel holder defines a plasma reaction chamber, optionally serving as its own vacuum chamber. Optionally, a source of vacuum, a reactant gas source, a gas feed or a combination of two or more of these can be supplied. Optionally, a gas drain, not necessarily including a source of vacuum, is provided to transfer gas to or from the interior of a vessel seated on the port to define a closed chamber.

pH Protective Organo-Siloxane Coatings Having Lubricious Properties

It is contemplated that syringes having a plunger-contacting inner surface comprising an organo-siloxane coating, without a separate discrete lubricity coating or substantially without the presence of a flowable lubricant, may still provide adequate lubricity for plunger advancement. As used herein, "substantially without the presence of a flowable lubricant," means that a flowable lubricant (e.g., PDMS) is not provided to a syringe barrel in amounts that would contribute to the lubricity of the plunger-syringe system. Since it is sometimes the practice to use a flowable lubricant when handling plungers prior to assembling them into syringes, "substantially without the presence of a flowable lubricant" in some cases may contemplate the presence of trace amounts of such lubricant as a result of such handling practices.

Accordingly, in one aspect, the invention is directed to an organo-siloxane coating on the inner surface of a parenteral container which provides lubricious properties conducive to acceptable plunger operation. The organo-siloxane coating may, for example, be any embodiment of the pH protective coating discussed above. The organo-siloxane coating may be applied directly to the interior wall of the container or as a top layer on a multi-layer coating set, e.g., the trilayer coating set discussed above. Preferably, this embodiment would obviate the need for a discrete lubricity coating, e.g., as described in U.S. Pat. No. 7,985,188 or a flowable lubricant, e.g., silicone oil.

The organo-siloxane coating can optionally provide multiple functions: (1) a pH resistant layer that protects an underlying layer or underlying polymer substrate from drug products having a pH from 4-10, optionally from 5-9; (2) a drug contact surface that minimizes aggregation, extractables and leaching; (3) in the case of a protein-based drug, reduced protein binding on the container surface; and (4) a lubricating layer, e.g., to facilitate plunger advancement when dispensing contents of a syringe.

Use of an organo-siloxane coating on a polymer-based container as the contact surface for a plunger provides distinct advantages. Plastic syringes and cartridges may be injection molded to tighter tolerances than their glass counterparts. It is contemplated that the dimensional precision achievable through injection molding allows optimization of the inside diameter of a syringe to provide sufficient compression to the plunger for CCI on the one hand, while not over-compressing the plunger so as to provide desired plunger force upon administration of the drug product. Optimally, this would eliminate or dramatically reduce the need for lubricating the syringe or cartridge with a flowable lubricant or a discrete lubricity coating, thus reducing manufacturing complexity and avoiding problems associated with silicone oil.

The invention will be illustrated in more detail with reference to the following Examples, but it should be understood that the present invention is not deemed to be limited thereto.

EXAMPLES

Example 1—Plunger Force

Three convertible plunger samples (Samples A (500), B (502) and C (504)), similar to the embodiment of the film coated convertible plunger of FIG. 26, were subjected to plunger force testing. The samples used 3.45 mm diameter spherical inserts. The desired outcome was a glide force of under 15 N, preferably under 10 N, even more preferably at or under 5 N. The samples were tested in a syringe having a plunger contacting surface comprising a pH protective coating made from a TMDSO precursor as part of a trilayer coating set, e.g., as shown in FIG. 4A and as described herein. The sample plunger sleeves were made from butyl rubber and the film was made from 25 micron thick CHEM-FILM® DF1100 PTFE. The syringe barrels were 6.35 mm in diameter.

Figure 28:
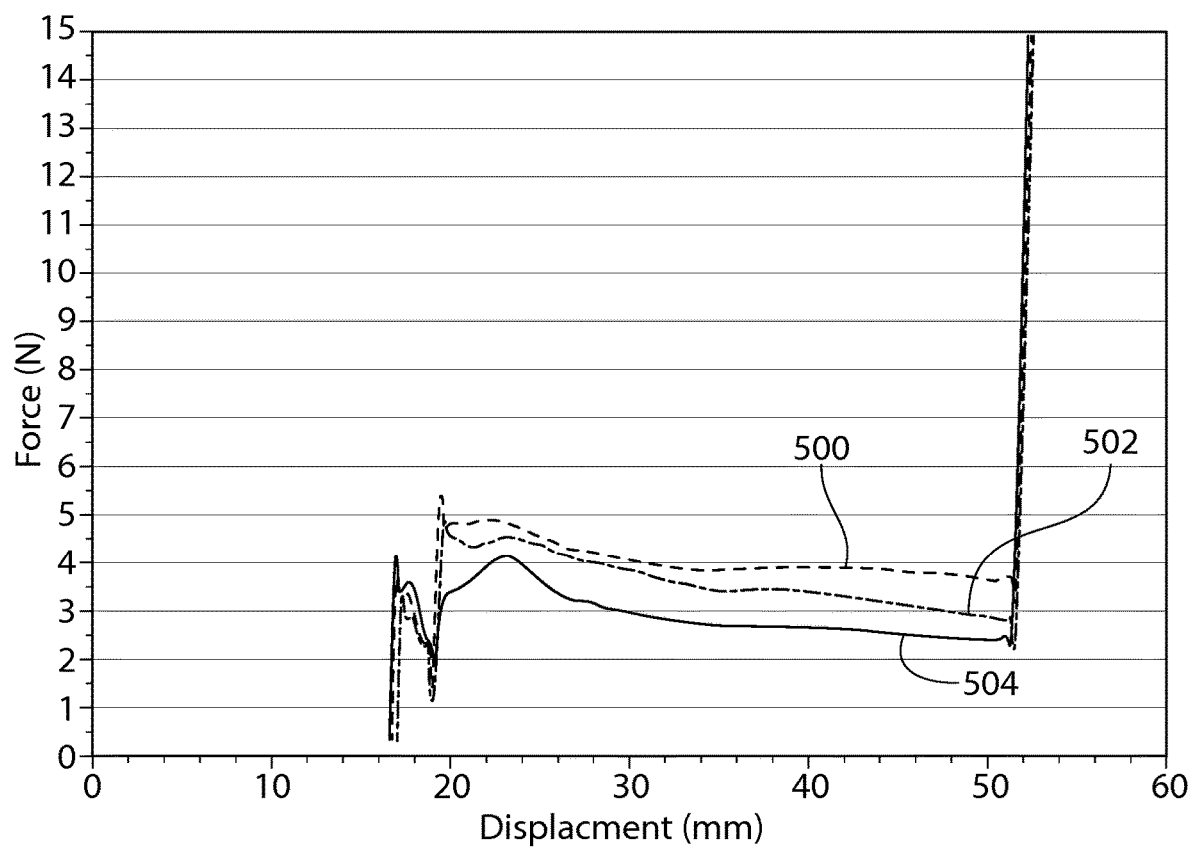
FIG. 28 is a chart illustrating break loose force and glide force measured from plunger test samples similar to the embodiment of the film coated convertible plunger of FIG. 26.

As shown in the chart in FIG. 28, break loose force for the three samples was between about 3.5N-5.5N. The glide force was relatively constant and consistent for each sample and was between about 2.5N and about 5 N. The test is thus regarded as a success in terms of achieving desired plunger force and consistency in the force profile of each sample (i.e., no drastic changes in glide force for a given sample).

Example 2—CCI

A CCI test method (vacuum decay test) is described above. Using this test, and referring to the chart in FIG. 29, three sets of plungers (Sets A, B and C) were used, all in a 6.35 mm diameter syringe. Set A 510 included plungers without any inserts, and consequently with no compression between the plunger storage sealing section and the syringe barrel. Set B 512 included plungers with 3.45 mm diameter spherical inserts, which caused slightly less than 3% compression of the plunger diameters on their respective storage sealing sections. Set C 514 included plungers with 3.58 mm spherical inserts, which caused about 4.8% compression of the plunger diameters on their respective storage sealing sections. For purposes of maintaining adequate CCI for prefilled syringes, a pressure drop of about 20 Pa or less is acceptable.

Figure 29:
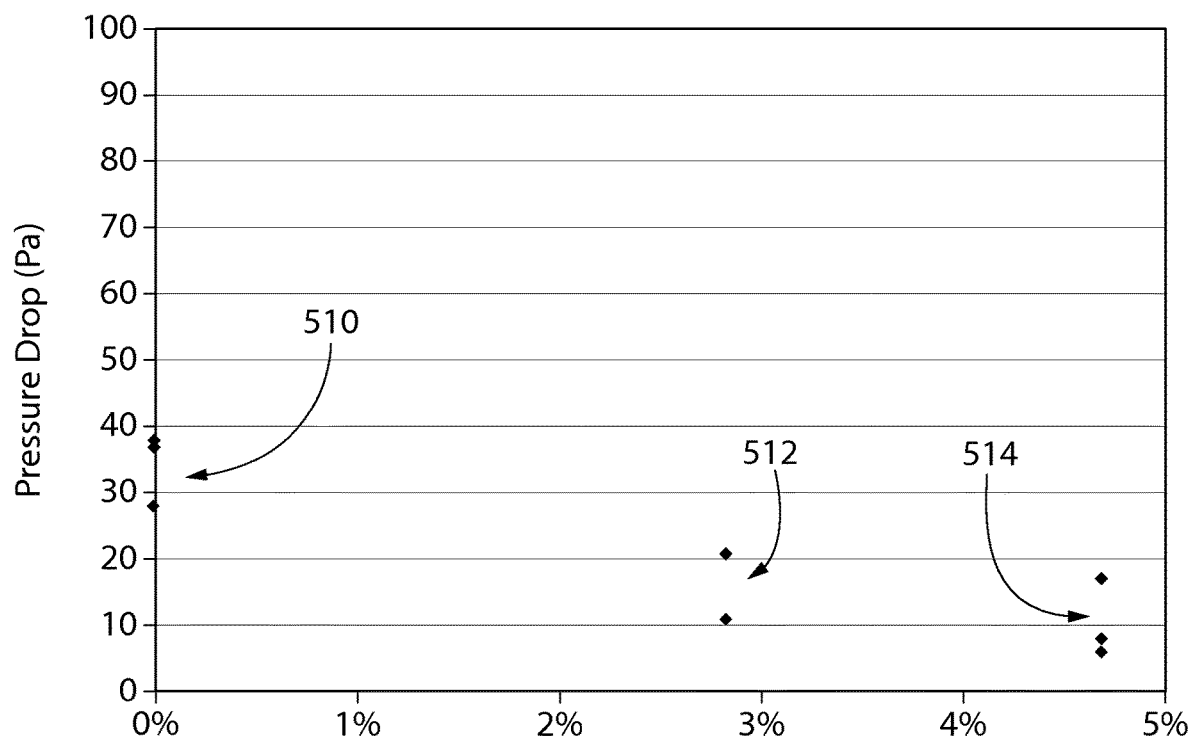
FIG. 29 is a chart illustrating the effect of plunger compression on pressure drop for purposes of testing CCI.

The chart in FIG. 29 shows the pressure drop for plunger Sets A, B and C subjected to the vacuum decay test. Set A 510 showed a pressure drop of well over 20 Pa, while Set B 512 and Set C 512 had pressure drops of around 20 Pa or less, which are positive results. This test shows that the spherical inserts (similar to the insert 42 of FIGS. 3 and 26) provide compression in the storage sealing section 51 of the plunger 12, resulting in acceptable CCI. By contrast, Set A 510, which had no inserts, did not provide adequate CCI.

Example 3—Comparative Plunger Forces Using Four Syringe Barrel Embodiments

This example describes plunger force testing of several convertible plunger samples, similar to the embodiment of the film coated convertible plunger of FIG. 26. The samples used 3.45 mm diameter spherical inserts. Results of this testing are shown in FIG. 30.

Four or five plunger samples were tested in each of the following four different syringe barrels: (a) a COP syringe barrel having an inner wall without flowable lubricant disposed between the plunger and the inner wall (the "bare COP syringe," the force testing results of which are identified by reference numeral 516); (b) a COP syringe barrel with a trilayer coating set applied to the inner wall thereof without flowable lubricant disposed between the plunger and the trilayer coating set (the "trilayer syringe," the force testing results of which are identified by reference numeral 518); (c) a glass syringe barrel without any flowable lubricant disposed between the plunger and the inner wall of the barrel (the "bare glass syringe," the force testing results of which are identified by reference numeral 520); and (d) a glass syringe barrel with a flowable lubricant (PDMS) disposed between the plunger and the inner wall of the barrel (the "glass syringe with PDMS," the force testing results of which are identified by reference numeral 522).

Figure 30:
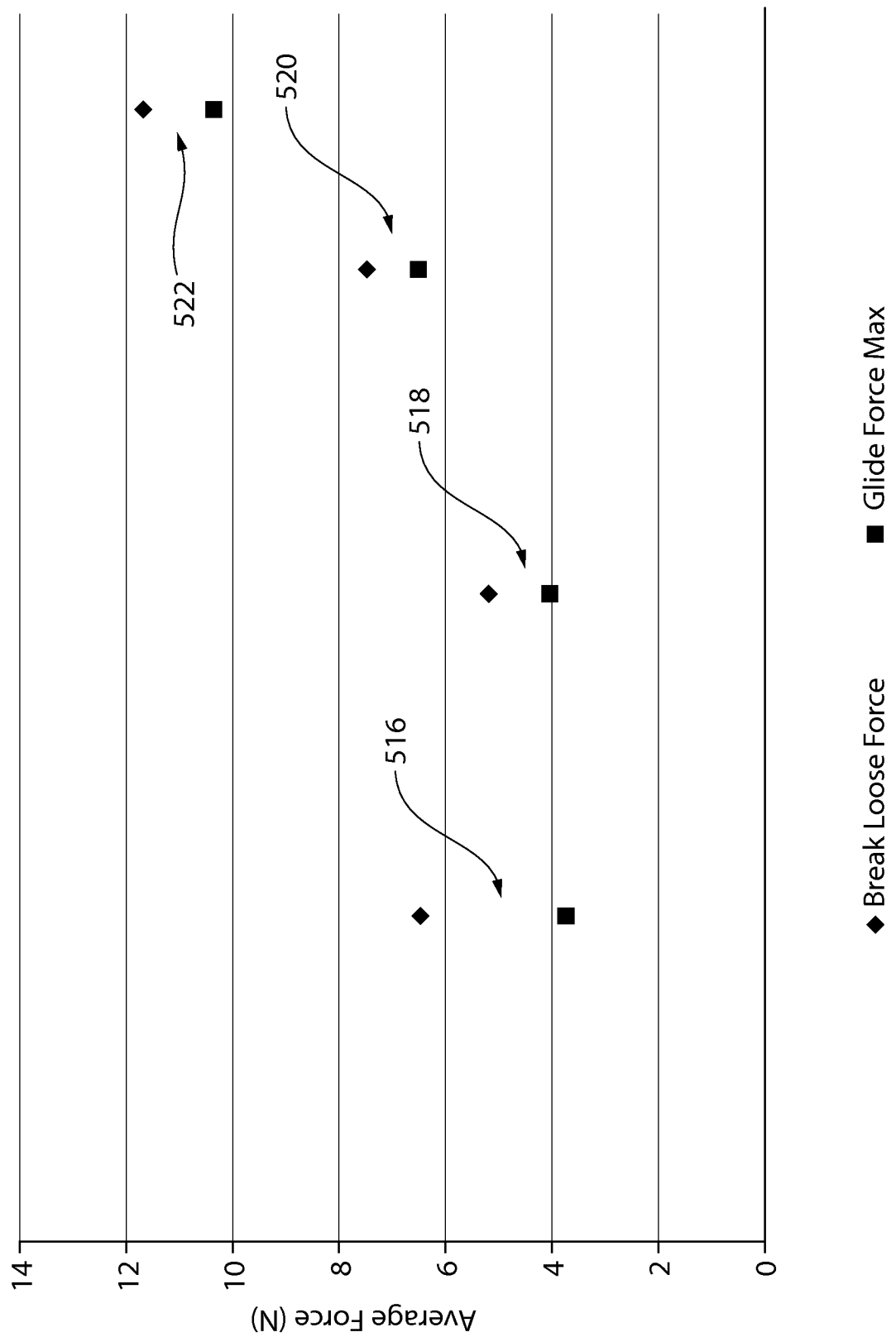
FIG. 30 is a chart illustrating break loose force and glide force measured from plunger test samples similar to the embodiment of the film coated convertible plunger of FIG. 26 on four different syringe embodiments.

The break loose forces and maximum glide forces depicted in FIG. 30 for a given syringe represent averages of results from testing four of five plunger samples with each syringe. The average break loose forces were as follows: (a) between 6 and 7 N for the bare COP syringe 516; (b) slightly above 5 N for the trilayer syringe 518; (c) between 7 and 8 N for the bare glass syringe 520; and (d) between 11 and 12 N for the glass syringe with PDMS 522. The average maximum glide forces were as follows: (a) slightly below 4 N for the bare COP syringe 516; (b) 4 N for the trilayer syringe 518; (c) between 6 and 7 N for the bare glass syringe 520; and (d) between 10 and 11 N for the glass syringe with PDMS 522.

Notably, the trilayer syringe 518 cumulative force results were optimal in that unlike the other syringes, both the break loose force and maximum glide force averages were about 5 N or under (which is a preferred plunger force). In addition, the differential between break loose force and maximum glide force for the trilayer syringe 518 was only about 1 N, which is significantly less than the approximately 2.5N differential between break loose force and maximum glide force for the bare COP syringe 516. Accordingly, a trilayer syringe with a plunger according to the present invention provides benefits associated with the trilayer syringe itself (e.g., pH protection, tight syringe tolerances, barrier properties) as well as a flowable lubricant free (or substantially flowable lubricant free) plunger system that provides both CCI and desired plunger forces in use.

While the invention has been described in detail and with reference to specific examples thereof, it will be apparent to one skilled in the art that various changes and modifications can be made therein without departing from the spirit and scope thereof.

What is claimed is:

1. A prefilled syringe comprising a barrel having an inner wall and a drug product contained within a product containing area, the prefilled syringe further comprising: a three-position plunger disposed in its entirety within the barrel, the three-position plunger having a generally cylindrical exterior surface, the three-position plunger comprising: a sleeve having an opening at a distal end thereof, a nose cone and a sidewall including a storage sealing section that comprises at least one rib and a liquid sealing section disposed between the nose cone and the storage sealing section, the sleeve further comprising a pre-load cavity proximal to and in communication with the opening, a first cavity proximal to and in communication with the pre-load cavity, and a second cavity proximal to and in communication with the first cavity, the at least one rib being generally aligned with the first cavity the three-position plunger further comprising an insert that is pre-inserted into the pre-load cavity in a pre-load mode in which compressive force or radial pressure that the three-position plunger exerts against the inner wall is unaffected by disposal of the insert in the pre-load cavity, the insert being configured to be displaced from the pre-load cavity to the first cavity and from the first cavity to the second cavity, the insert being configured to compress the at least one rib outwardly when the insert is positioned in the first cavity, the storage sealing section being generally aligned with the first cavity and maintaining an expanded state by the insert being disposed within the first cavity, the insert applying outward radial pressure against an interior surface of the three-position plunger at a location radially inward of the storage sealing section, the expanded state providing a compressive force of the storage sealing section against the inner wall, the three-position plunger being reducible to a constricted state, wherein the compressive force against the inner wall is reduced or removed entirely by effectuating axial displacement of the insert from the first cavity to the second cavity upon application of force onto the three-position plunger in a direction toward the drug product, wherein the three-position plunger in the constricted state provides less compressive force against the sidewall than when in the expanded state, such that force needed to axially displace the three-position plunger in the constricted state is less than would be required to axially displace the three-position plunger in the expanded state, and wherein the liquid sealing section provides a liquid tight seal against the inner wall both when the three-position plunger is in the expanded state and when the three-position plunger is in the constricted state.

2. The prefilled syringe of claim 1, wherein the three-position plunger further includes a connector body operably connected to the sleeve, wherein a portion of the connector body is positioned within the sleeve and is configured to provide support for compression of the sleeve against an inner surface of the inner wall of the barrel.

3. The prefilled syringe of claim 2, wherein the three-position plunger further includes a plunger rod having a shaft configured to displace the insert from the first cavity to the second cavity when the shaft is displaced from a first position to a second position, wherein the plunger rod is operably connected to the connector body.

4. The prefilled syringe of claim 1, wherein the three-position plunger further includes a film coating or molded cap on at least a portion of the sleeve, wherein the film coating or molded cap has a lubricity that is greater than a lubricity of a material of a sidewall of the plunger.

5. The prefilled syringe of claim 1, wherein the syringe is made from an injection moldable thermoplastic material and comprises an organo-siloxane coating or layer, as a plunger-contacting surface, substantially without presence of a flowable lubricant.

6. The prefilled syringe of claim 5, wherein the organo-siloxane coating or layer is a pH protective coating, as a top layer of a trilayer coating set.

7. The prefilled syringe of claim 1, the sleeve having an external profile that is unaffected by disposal of the insert in the pre-load cavity.

8. The prefilled syringe of claim 1, wherein a narrowing transition region separates each cavity from an adjacent cavity so as to make each cavity a physically distinct compartment.

9. The prefilled syringe of claim 8, the sleeve having an external profile that is unaffected by disposal of the insert in the pre-load cavity.

* * * * *